US008759342B2

(12) United States Patent
Shyamali et al.

(10) Patent No.: US 8,759,342 B2
(45) Date of Patent: Jun. 24, 2014

(54) BENZO[1,4]OXAZIN-3-ONE, BENZO[1,4]THIAZIN-3-ONE AND QUINOLIN-2-ONE UROTENSIN II RECEPTOR ANTAGONISTS

(75) Inventors: Ghosh Shyamali, Norristown, PA (US); William A Kinney, Newtown, PA (US); Edward C Lawson, Pipersville, PA (US); Diane K Luci, Horsham, PA (US); Bruce E Maryanoff, Forest Grove, PA (US); Francois Maria Sommen, Wortel (BE)

(73) Assignee: Janssen Pharmaceutica NV, Beerse (BE)

( * ) Notice: Subject to any disclaimer, the term of this patent is extended or adjusted under 35 U.S.C. 154(b) by 818 days.

(21) Appl. No.: 11/881,268

(22) Filed: Jul. 26, 2007

(65) Prior Publication Data

US 2008/0039454 A1 Feb. 14, 2008

Related U.S. Application Data

(60) Provisional application No. 60/834,720, filed on Jul. 31, 2006.

(51) Int. Cl.
*A61K 31/535* (2006.01)
*C07D 265/36* (2006.01)

(52) U.S. Cl.
USPC ........................................ 514/230.5; 544/105

(58) Field of Classification Search
None
See application file for complete search history.

(56) References Cited

U.S. PATENT DOCUMENTS

| | | | |
|---|---|---|---|
| 3,629,266 A * | 12/1971 | Havera et al. | 546/158 |
| 6,011,050 A | 1/2000 | Muller et al. | |
| 6,544,992 B1 | 4/2003 | Dhanak et al. | |
| 6,583,144 B2 | 6/2003 | Ohkura et al. | |
| 6,884,887 B1 | 4/2005 | Riermeier et al. | |
| 6,911,464 B2 | 6/2005 | Man et al. | |
| 7,043,052 B2 | 5/2006 | Rhoads et al. | |
| 7,056,942 B2 * | 6/2006 | Hildesheim et al. | 514/411 |
| 7,307,075 B2 | 12/2007 | Skjaerbaek et al. | |
| 7,790,715 B2 | 9/2010 | Herold et al. | |
| 7,915,260 B2 | 3/2011 | Rhoads et al. | |
| 7,968,570 B2 | 6/2011 | Clayton et al. | |
| 8,008,299 B2 | 8/2011 | Kinney et al. | |
| 8,193,191 B2 | 6/2012 | Maryanoff et al. | |
| 2001/0049371 A1 | 12/2001 | Muller et al. | |
| 2003/0232822 A1 | 12/2003 | Bang-Andersen et al. | |
| 2004/0229871 A1 | 11/2004 | Cesure et al. | |
| 2004/0259873 A1 | 12/2004 | Man et al. | |
| 2004/0267051 A1 | 12/2004 | Boerner et al. | |
| 2005/0143393 A1 | 6/2005 | Dean et al. | |
| 2005/0203090 A1 | 9/2005 | Man et al. | |
| 2005/0239867 A1 | 10/2005 | Zeldis | |
| 2005/0282819 A1 | 12/2005 | Graham | |
| 2007/0027163 A1 | 2/2007 | Bissantz et al. | |
| 2008/0039454 A1 | 2/2008 | Ghosh et al. | |
| 2010/0029616 A1 | 2/2010 | Kinney et al. | |

FOREIGN PATENT DOCUMENTS

| | | |
|---|---|---|
| DE | 2009685 | 9/1970 |
| JP | 7242662 A | 9/1995 |
| WO | 98/52919 | 11/1998 |
| WO | 01/05741 | 1/2001 |
| WO | 02/47687 | 6/2002 |
| WO | 03/014061 | 2/2003 |
| WO | 03/091248 | 11/2003 |
| WO | WO 03/091248 A1 | 11/2003 |
| WO | 03/104216 | 12/2003 |
| WO | 2004/024702 | 3/2004 |
| WO | 2004/078114 | 9/2004 |
| WO | 2004/080422 | 9/2004 |
| WO | 2004/080423 | 9/2004 |
| WO | 2005/034873 | 4/2005 |
| WO | WO 2005/034873 A2 | 4/2005 |
| WO | WO 2005/061457 A1 | 7/2005 |
| WO | 2005/072226 | 8/2005 |
| WO | WO 2005/072226 A2 | 8/2005 |
| WO | 2006/020879 | 2/2006 |
| WO | 2007/008541 | 1/2007 |
| WO | 2007/081995 | 7/2007 |
| WO | 2008/153902 | 12/2008 |

OTHER PUBLICATIONS

Jantzen. Modern Pharmaceutics, 1996, p. 596.*
A. Marchese, M. et. al., Genomics 1995, 29, 335-344.
D. Pearson, et. al., Proc. Natl. Acad. Sci. USA 1980, 77 5021-5024.
H. K. Hall, Jr. J. Am. Chem. Soc., 1957, 79, 5444-5447.
J. E. Gartlon, Eur. J. of Pharmacol, 2004, 493, 95-98.
J. Gartlon, et. al., Psychopharmacology 2001, 15, 426-433.
J. M. Conlon, et. al., J. Exp. Zool. 1996, 275, 226-238.
J. Qi, et. al, "Characterization of Functional Urotensin II Receptors" Peptides 2005, 26, 683-690.
K. Ong, et. al., Peptides, 2006, 27(7), 1659-1667.
K. Totsune, et. al., Clin. Sc. 2003, 104, 1-5.
K. Totsune, et.al., Lancet 2001, 358, 810-811.
M. Clozel, et. al, J. Pharmacol. Exp. Ther. 2006, 316 (3), 1115-1121.
M. Lim, et. al., Circulation 2004, 109, 1212-1214.
M. Tal et. al., Biochm Biophys. Res. Commun. 1995, 209, 752-759.
N. Bousette, et. al. Journal of Molecular and Cellular Cardiology 2006, In Press.
N. Bousette, et. al., Atherosclerosis 2004, 176, 117-123.
P.R. Eastwood, Tetrahedron, Lett., 2000, 41, 3705.
R.A. Silvestre, et. al., Horm. Metab. Res. 2001, 33, 379-381.

(Continued)

*Primary Examiner* — Noble Jarrell
(74) *Attorney, Agent, or Firm* — Yuriy P. Stercho

(57) ABSTRACT

The invention is directed to benzo[1,4]oxazin-3-one, benzo[1,4]thiazin-3-one and quinolin-2-one Urotensin II receptor antagonists useful in treating or ameliorating a Urotensin-II mediated disorder. More specifically, the present invention relates to certain novel benzo[1,4]oxazin-3-one, benzo[1,4]thiazin-3-one and quinolin-2-one compounds and methods for preparing compounds, compositions, intermediates and derivatives thereof. Pharmaceutical compositions and methods for treating or ameliorating a Urotensin-II mediated disorder using compounds of the invention are also described.

32 Claims, No Drawings

(56) References Cited

OTHER PUBLICATIONS

R.S. Ames, Et. al., Nature (London) 1999, 401, 282-286.
S. A. Douglas, et. al., Trends Cardiovasc, Med. 2000, 10, 229-237.
S. Ghosh, et. al. "Convenient Preparation of Aryl-Substitute Nortopanes by Suzuki-Miyaura Methodology" Canadian Journal of Chemistry 2006. 84, 555-560.
Synthetic Communications 23 (6) 789-795, 1993 A.E. Moormann.
T. Watanabe, et. al., Circulation 2001, 104, 16-18.
W. A. Kinney, et. al., "Structure-Function Analysis of Urotensin II and its Use in the Construction of a Ligand-Receptor Working Model" Angewandte. Chem., Intl. Ed 2002, 41,2940-2944.
W. K. Lee, J. Org. Chem. 1993, 58, 1109-1117.
Y. Matsumoto, Neuroscience Letters 2004, 358, 99-102.
Y. Zou, et. al. FEBS Letters 2001, 508, 57-60.
EP Search Report 07836257.1-1211/2049120, dated Aug. 4, 2011.
Jian, et al., "Non-Peptidic Urotensin-II Receptor Modulators", Expert Opinion on Therapeutic Patents, Apr. 2006, pp. 467-479, vol. 16, No. 4.
Vippagunta, et al., "Crystalline Solids" Advanced Drug Delivery Reviews, 2001, pp. 3-26, vol. 48.
Metabolite, The Columbia Encyclopedia, http://www.encyclopedia.com/doc/1E1-metabolit.html, assessed Nov. 8, 2007, Sixth Edition.
Banker and Rhodes, Modern Pharmaceutics, Third Edition, p. 596, 1996.
PCT/US07/16806, dated Dec. 2007.
EP Search Report, PCT/US2007000644, dated Jul. 6, 2010.
ISR, PCTUS07/00644, dated Sep. 12, 2007.
ISR, PCT/US08/07076, dated Aug. 20, 2008.
EP Search Report, 09 791 047.5-2101, dated May 27, 2011.
ISR, PCT/US2009/052403, dated, Nov. 31, 2009.
JP Rejection, appl. 2009-522801, dated Oct. 11, 2012.
Mertens, Journal of Medicinal Chemistry, 1993, 36(17), pp. 2526-2535.
Bohn, et al., "Urotensin II Evokes Potent Vasoconstriction in Humans in Vivo," BR. J. Pharmacol., 2002, pp. 25-27, vol. 135.
Gillaspy, et al., "A Simple Method for the Formation of Cycolpropylamines: The first Sysnthesis of Tricyclopropylamine," Tetrahedron Letters, 1995, pp. 7399-7402, vol. 36.
EP Office Action 07836257.1-1211, dated Jun. 25, 2012.
EP Office Action 07836257.1-1451, dated Jun. 20, 2013.

* cited by examiner

BENZO[1,4]OXAZIN-3-ONE, BENZO[1,4]THIAZIN-3-ONE AND QUINOLIN-2-ONE UROTENSIN II RECEPTOR ANTAGONISTS

CROSS REFERENCE TO RELATED APPLICATIONS

This present application claims benefit of U.S. Provisional Patent Application Ser. No. 60/834,720 filed Jul. 31, 2006, which is incorporated herein by reference in its entirety and for all purposes.

FIELD OF THE INVENTION

The present invention relates to certain novel compounds, methods for preparing compounds, compositions, intermediates and derivatives thereof and methods for treating or ameliorating a Urotensin-II mediated disorder. More particularly, the compounds of the present invention are Urotensin-II receptor antagonists useful for treating or ameliorating Urotensin-II mediated disorders.

BACKGROUND OF THE INVENTION

Urotensin-II (U-II) is a cysteine-linked cyclic peptide, which exerts potent effects on the cardiovascular, renal, pancreatic, and central nervous systems. Originally, this substance was isolated from the urophysis (a caudal neurosecretory organ) of the goby fish (*Gillichthys mirabilis*) as a 12-mer, AGTAD-cyclo(CFWKYC)-V (D. Pearson. J. E. Shively, B. R. Clark, I. I. Geschwind, M. Barkley, R. S, Nishioka, H. A. Bern, *Proc. Nat. Acad. Sci. USA* 1980, 77, 5021-5024), but it has now been identified in all classes of vertebrates. The composition of U-II ranges from 11 amino acids in humans to 14 amino acids in mice, always with a conserved cysteine-linked macrocycle, CFWKYC. Recently, the U-II receptor was identified (R. S. Ames, H. M. Sarau, J. K. Chambers, R. N. Willette, N. V. Aiyar, A. M. Romanic, C. S. Louden, J. J. Foley, C. F. Sauermelch, R. W. Coatney, Z. Ao, J. Disa, S. D. Holmes, J. M. Stadel, J. D. Martin, W.-S. Liu, G. I. Glover, S. Wilson, D. E. McNulty, C. E. Ellis, N. A. Elshourbagy, U. Shabon, J. J. Trill, D. W. P. Hay, E. H. Ohlstein, D. J. Bergsma, S. A. Douglas, *Nature (London)* 1999, 401, 282-286) as a G-protein-coupled receptor (GPCR) previously known as the GPR14 orphan receptor, (M. Tal, D. A. Ammar, M. Karpuj, V. Krizhanovsky, M. Naim, D. A. Thompson, *Biochem. Biophys. Res. Commun.* 1995, 209, 752-759; and A. Marchese, M. Heiber, T. Nguyen, H. H. Q. Heng, V. R. Saldivia, R. Cheng, P. M. Murphy, L.-C. Tsui, X. Shi, P. Gregor, S. R. George, B. F. O'Dowd, J. M. Docherty, *Genomics* 1995, 29, 335-344) which is expressed predominantly in cardiovascular tissues.

Goby U-II possesses powerful vasoconstrictor activity in fish, mammals, and humans (J. M. Conlon, K. Yano, D. Waugh, N. Hazon, *J. Exp. Zool.* 1996, 275, 226-238; F. Böhm, J. Pernow, *Br. J. Pharmacol.* 2002, 135, 25-27). Moreover, it appears to be the most potent vasoconstrictor known, (S. A. Douglas, E. H. Ohlstein, *Trends Cardiovasc. Med.* 2000, 10, 229-237) causing concentration-dependent contraction of isolated arterial rings of rats and humans with an $EC_{50}$ value of less than 1 nM, which is ca. ten times more potent than endothelin-1. Recently, Kikkawa, H. and Kushida, H. in International Publication WO 2005/072226 disclosed the use of Urotensin-II antagonists for the prevention and/or treatment of inflammatory bowel diseases including, but not limited to, Crohn's disease, ulcerative colitis, and inflammatory colitis caused by bacteria, ischemia, radiation, drugs, or chemical substances.

Relative to the role of U-II in chronic vascular disease, this peptide was reported to induce hypertrophy in cardiomyocytes (Y. Zou, R. Nagai, T. Yamazaki, *FEBS Letters* 2001, 508, 57-60) and the proliferation of smooth muscle cells (T. Watanabe, R. Pakala, T. Katagiri, C. R. Benedict, *Circulation* 2001, 104, 16-18), which suggests an involvement in heart failure and atherosclerosis. In addition, U-II has been shown to increase peripheral vascular tone, a characteristic of chronic heart failure (M. Lim, S. Honisett, C. D. Sparkes, P. Komesaroff, A. Kompa, H. Krum, *Circulation* 2004, 109, 1212-1214). Recent results have shown increased U-II receptor levels observed in the atherosclerotic lesions of the human aorta (N. Bousette, L. Patel, S. A. Douglas, E. H. Ohlstein, A. Giaid, *Atherosclerosis* 2004, 176, 117-123).

Relative to healthy individuals, the expression of U-II-like immunoreactivity was 2-fold higher in the plasma of patients with renal dysfunction who were not on dialysis, and 3-fold higher in those on haemodialysis (K. Totsune, K. Takahashi, Z. Arihara, M. Sone, F. Satoh, S. Ito, Y. Kimura, H. Sasano, O. Murakami, *Lancet* 2001, 358, 810-811). Recently, Kinoshita, M. and Kushida, H. in International Publication WO 2005/034873 disclosed the use of Urotensin-II antagonists for reducing nephrotoxicity and diarrhea caused by anti-neoplastic agents.

U-II has been described as a potential mediator in diabetes. For instance, U-II was shown to inhibit the release of insulin in the perfused rat pancreas in response to increasing glucose levels (R. A. Silvestre, J. Rodríguez-Gallardo, E. M. Egido, J. Marco, *Horm. Metab. Res.* 2001, 33, 379-381). Elevated U-II levels were seen in patients with diabetis mellitus (K. Totsune, K. Takahashi, Z. Arihara, M. Sone, S. Ito, O. Murakami, *Clin. Sci.* 2003, 104, 1-5) even without renal failure. Haplotypes in the urotensin II gene and urotensin II receptor gene are reported to be associated with insulin resistance and impaired glucose tolerance (K. Ong, L. Wong, Y. Man, R. Leung, Y. Song, K. Lam, B. Cheung, *Peptides,* 2006, 27(7), 1659-1667).

A U-II antagonist may be useful for the treatment of pain, neurological and psychiatric conditions, migraine, neuromuscular deficit, anxiety disorders and cardiovascular disorders. ICV (intracerebroventricular) administration of U-II increases rearing, grooming, and motor activity suggesting a CNS stimulatory activity (J. Gartlon, F. Parker, D. C. Harrison, S. A. Douglas, T. E. Ashmeade, G. J. Riley, Z. A. Hughes, S. G. Taylor, R. P. Munton, J. J. Hagan, J. A. Hunter, D. N. C. Jones, *Psychopharmacology* 2001, 155, 426-433). U-II increases Fos expression in the cingulate cortex and periaqueductal grey brain regions important in cognitive, emotional, and motor responses; the perceptions of pain; and panic responses (J. E. Gartlon, T. Ashmeade, M. Duxon, J. J. Hagan, D. N. C. Jones, *Eur. J. of Pharmacol.* 2004, 493, 95-98). U-II induces anxiogenic-like responses in rodents in the elevated plus maze and hole-board tests (Y. Matsumoto, M. Abe, T. Watanabe, Y. Adachi, T. Yano, H. Takahashi, T. Sugo, M. Mori, C. Kitada, T. Kurokawa, M. Fujino, *Neuroscience Letters* 2004, 358, 99-102).

Application JP 07242662 (also referred to as JP1995242662) describes substituted 4H-benzo[1,4]oxazin-3-ones as phospholipase A2 and interleukin 1 inhibitors.

PCT Application WO 03/091248 describes 7-fluoro-6-{1-[2-(7-fluoro-2-methyl-quinolin-5-yloxy)-ethyl]-piperidin-4-ylmethyl}-4H-benzo[1,4]oxazin-3-one as a $5-HT_{1A}$ receptor inhibitor.

PCT Application WO 05/061457 describes substituted benzo[1,4]oxazines as renin inhibitors.

Accordingly, it is an object of the present invention to provide compounds that are Urotensin-II antagonists useful for treating Urotensin-II mediated disorders.

It is another object of the invention to provide a process for preparing compounds, compositions, intermediates and derivatives thereof.

It is a further object of the invention to provide methods for treating Urotensin-II mediated cardiovascular, renal, pancreatic and central nervous system disorders including, but not limited to, chronic vascular disease, vascular hypertension, heart failure, atherosclerosis, inflammatory bowel disease, Crohn's disease, ulcerative colitis, inflammatory colitis (caused by bacteria, ischemia, radiation, drugs or chemical substances), renal dysfunction, renal failure, renal failure caused by drug induced toxicity, nephrotoxicity and diarrhea caused by anti-neoplastic agents, nephrotoxicity caused by radiocontrast agents and aminoglycosides, post-myocardial infarction, pulmonary hypertension, pulmonary fibrosis, insulin resistance and impaired glucose tolerance, diabetes, diabetic complications, diabetic nephropathy, pain, Alzheimer's disease, convulsions, depression, migraine, psychosis, anxiety, neuromuscular deficit and stroke.

SUMMARY OF THE INVENTION

The present invention is directed to a compound of Formula (I):

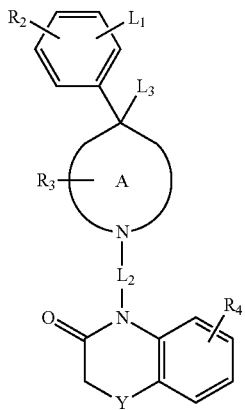

and forms thereof, wherein Ring A, Y, $L_1$, $L_2$, $L_3$, $R_2$, $R_3$ and $R_4$ are as defined herein.

Illustrative of the invention is a pharmaceutical composition comprising a pharmaceutically acceptable carrier and a compound of Formula (I). Illustrative of the invention is a process for making a pharmaceutical composition comprising mixing a compound of Formula (I) and a pharmaceutically acceptable carrier.

The present invention is further directed to methods for treating or ameliorating a Urotensin II-mediated disorder. In particular, the method of the present invention is directed to treating or ameliorating a Urotensin II-mediated disorder including, but not limited to, chronic vascular disease, vascular hypertension, heart failure, atherosclerosis, inflammatory bowel disease, Crohn's disease, ulcerative colitis, inflammatory colitis, renal dysfunction, renal failure, renal failure caused by drug induced toxicity, nephrotoxicity and diarrhea caused by anti-neoplastic agents, nephrotoxicity caused by radiocontrast agents and aminoglycosides, post-myocardial infarction, pulmonary hypertension, pulmonary fibrosis, insulin resistance and impaired glucose tolerance, diabetes, diabetic complications, diabetic nephropathy, pain, Alzheimer's disease, convulsions, depression, migraine, psychosis, anxiety, neuromuscular deficit and stroke.

The present invention is also directed to methods for producing the instant compounds and pharmaceutical compositions and medicaments thereof.

DETAILED DESCRIPTION OF THE INVENTION

The present invention is directed a compound of Formula (I):

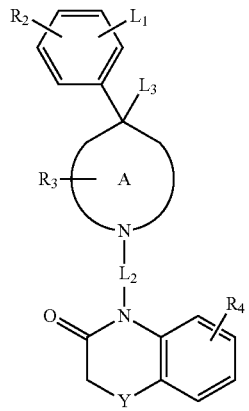

and forms thereof, wherein

Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —NH$R_6$, wherein $C_{1-8}$alkoxy is optionally substituted with one, two or three substituents each selected from the group consisting of $C_{1-8}$alkoxy, halogen, hydroxy and —NH$R_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-18}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

An example of the present invention includes a compound of Formula (I) and forms thereof, wherein Ring A is piperidinyl.

An example of the present invention includes a compound of Formula (I) and forms thereof, wherein Ring A is 8-aza-bicyclo[3.2.1]oct-2-enyl.

An example of the present invention includes a compound of Formula (I) and forms thereof, wherein Ring A is 8-aza-bicyclo[3.2.1]octyl.

An example of the present invention includes a compound of Formula (I) and forms thereof, wherein Ring A is 1,2,3,6-tetrahydro-pyridinyl.

An example of the present invention includes a compound of Formula (I) and forms thereof, wherein Ring A is substituted with one or two $C_{1-4}$alkyl.

An example of the present invention includes a compound of Formula (I) and forms thereof, wherein Y is $CH_2$.

An example of the present invention includes a compound of Formula (I) and forms thereof, wherein Y is O.

An example of the present invention includes a compound of Formula (I) and forms thereof, wherein Y is S.

An example of the present invention includes a compound of Formula (I) and forms thereof, wherein $R_1$ is selected from the group consisting of $C_{1-8}$alkyl, $C_{1-8}$alkoxy, aryl-$C_{1-8}$alkyl, $C_{3-14}$cycloalkyl, $C_{3-4}$cycloalkyl-$C_{1-8}$alkyl, heterocyclyl, heterocyclyl-$C_{1-8}$alkyl and heteroaryl-$C_{1-8}$alkyl, wherein $C_{1-8}$alkyl is optionally substituted with a substituent selected from the group consisting of $C_{1-8}$alkoxy, hydroxy and —NHR$_6$, wherein $C_{1-8}$alkoxy is optionally substituted with —NHR$_6$, wherein each instance of aryl is optionally substituted with one, two or three substituents each selected from the group consisting of $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl.

An example of the present invention includes a compound of Formula (I) and forms thereof, wherein $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —NHR$_6$, wherein $C_{1-8}$alkoxy is optionally substituted with —NHR$_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl.

An example of the present invention includes a compound of Formula (I) and forms thereof, wherein $R_2$ is one substituent selected from the group consisting of hydrogen, $C_{1-8}$alkyl, $C_{1-8}$alkoxy and halogen.

An example of the present invention includes a compound of Formula (I) and forms thereof, wherein $R_3$ is one or two substituents each selected from the group consisting of hydrogen and $C_{1-4}$alkyl.

An example of the present invention includes a compound of Formula (I) and forms thereof, wherein $R_4$ is one substituent selected from the group consisting of hydrogen, $C_{1-8}$alkyl and halogen.

An example of the present invention includes a compound of Formula (I) and forms thereof, wherein $R_5$ is hydrogen.

An example of the present invention includes a compound of Formula (I) and forms thereof, wherein $R_5$ is $C_{1-4}$alkyl.

An example of the present invention includes a compound of Formula (I) and forms thereof, wherein $R_6$ is selected from the group consisting of $C_{1-8}$alkyl-carbonyl, $C_{1-8}$alkoxy-carbonyl, $C_{1-8}$alkyl-N($R_5$)-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl.

An example of the present invention includes a compound of Formula (I) and forms thereof, wherein $R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl.

An example of the present invention includes a compound of Formula (I) and forms thereof, wherein $R_7$ is selected from the group consisting of $C_{1-8}$alkyl and aryl-$C_{1-8}$alkyl.

An example of the present invention includes a compound of Formula (I) and forms thereof, wherein $R_7$ is selected from the group consisting of $C_{1-8}$alkyl and phenyl-$C_{1-8}$alkyl.

An example of the present invention includes a compound of Formula (I) and forms thereof, wherein Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl and heteroaryl-$C_{1-8}$alkyl, wherein $C_{1-8}$alkyl is optionally substituted with a substituent selected from the group consisting of $C_{1-8}$alkoxy, hydroxy and —NR$_6$, wherein $C_{1-8}$alkoxy is optionally substituted with —NHR$_6$, wherein each instance of aryl is optionally substituted with one, two or three substituents each selected from the group consisting of $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and $R_7$ is selected from the group consisting of $C_{1-8}$alkyl and aryl-$C_{1-8}$alkyl.

An example of the present invention includes a compound of Formula (I) and forms thereof, wherein Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

The present invention is directed a compound of Formula (Ia):

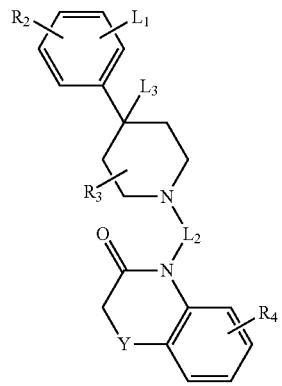

and forms thereof, wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —$NHR_6$, wherein $C_{1-8}$alkoxy is optionally substituted with one, two or three substituents each selected from the group consisting of $C_{1-8}$alkoxy, halogen, hydroxy and —$NHR_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

An example of the present invention includes a compound of Formula (Ia) and forms thereof, wherein Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-18}$alkyl-N($R_5$)-carbonyl or aryl-$C_{1-18}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

The present invention is directed a compound of Formula (Ib):

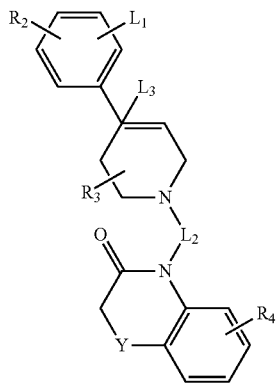

and forms thereof, wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —$NHR_6$, wherein $C_{1-8}$alkoxy is optionally substituted with one, two or three substituents each selected from the group consisting of $C_{1-8}$alkoxy, halogen, hydroxy and —$NHR_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

An example of the present invention includes a compound of Formula (Ib) and forms thereof, wherein Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-18}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

The present invention is directed a compound of Formula (Ic):

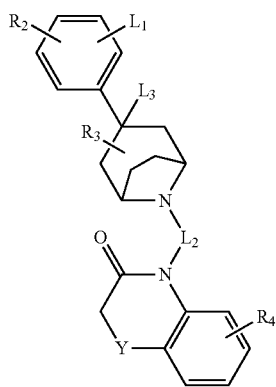

and forms thereof, wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —NH$R_6$, wherein $C_{1-8}$alkoxy is optionally substituted with one, two or three substituents each selected from the group consisting of $C_{1-8}$alkoxy, halogen, hydroxy and —NH$R_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

An example of the present invention includes a compound of Formula (Ic) and forms thereof, wherein Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —NR$_6$, wherein $C_{1-8}$alkoxy is optionally substituted with —NHR$_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

The present invention is directed a compound of Formula (Id):

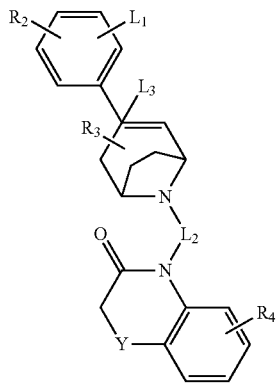

and forms thereof, wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —$NR_6$, wherein $C_{1-8}$alkoxy is optionally substituted with one, two or three substituents each selected from the group consisting of $C_{1-8}$alkoxy, halogen, hydroxy and —$NR_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

An example of the present invention includes a compound of Formula (Id) and forms thereof, wherein Y is selected from the group consisting of $CH_2$, O and S;

$L_1$ is absent or is selected from the group consisting of —C(O)O—$R^1$, —C(O)N($R_5$)—$R_1$ and —NHC(O)—$R^1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

An example of the present invention includes a compound of Formula (I) and forms thereof selected from the group consisting of:

Cpd 1

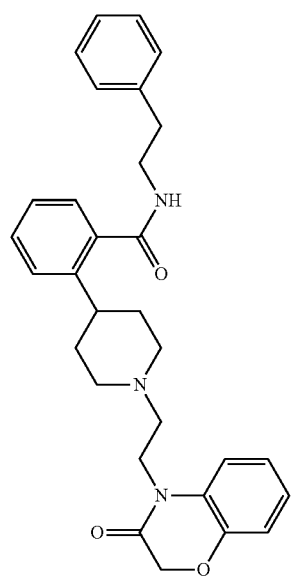

Cpd 2
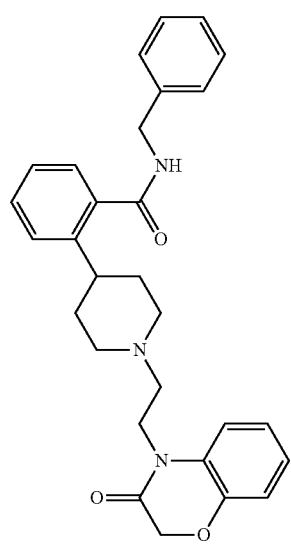
Cpd 3
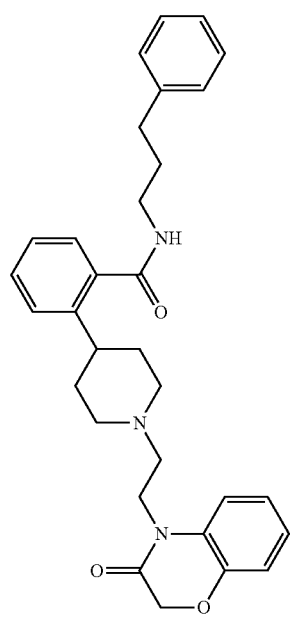
Cpd 4
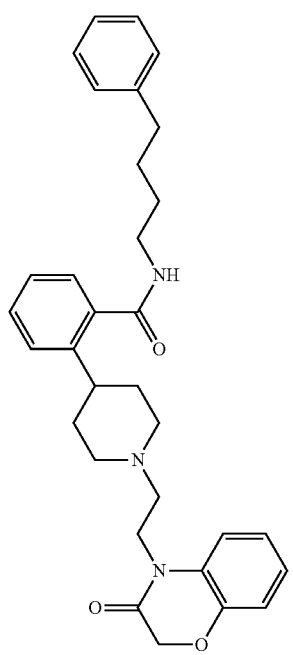
Cpd 5
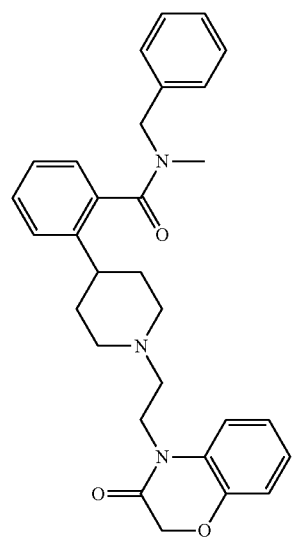

Cpd 6
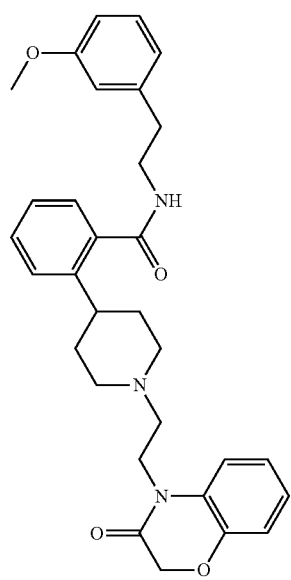
Cpd 8
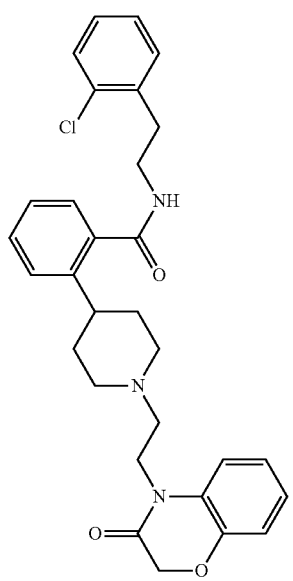
Cpd 7
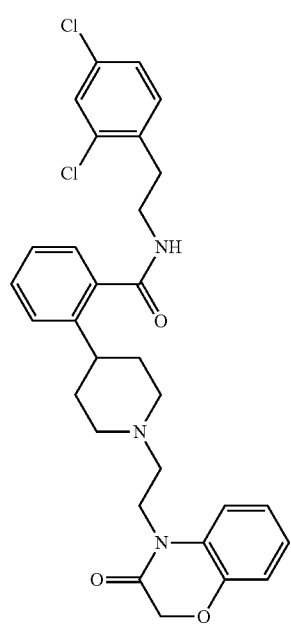
Cpd 9
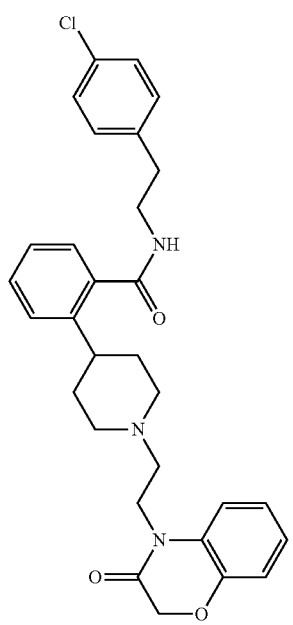

Cpd 10
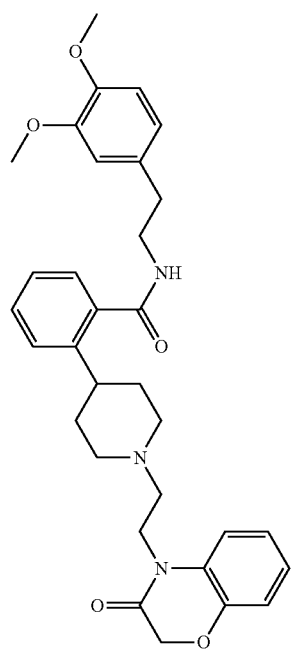
Cpd 11
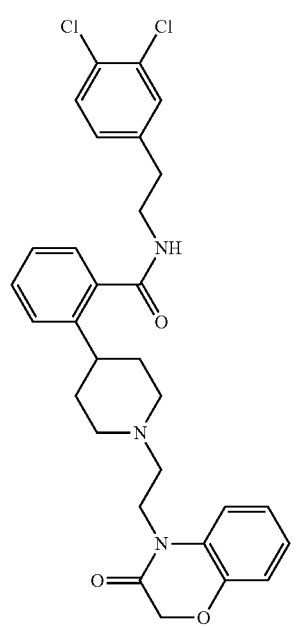
Cpd 12
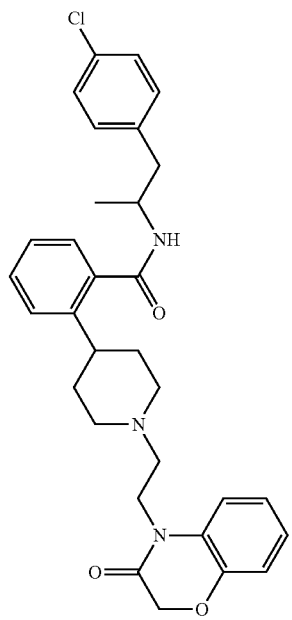
Cpd 13
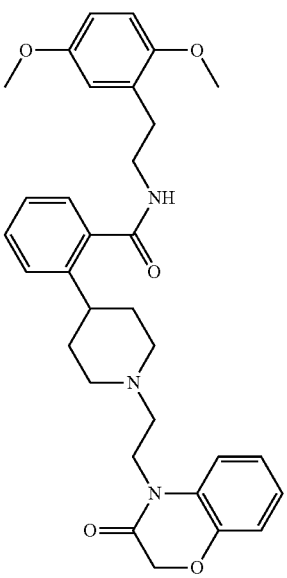

Cpd 14
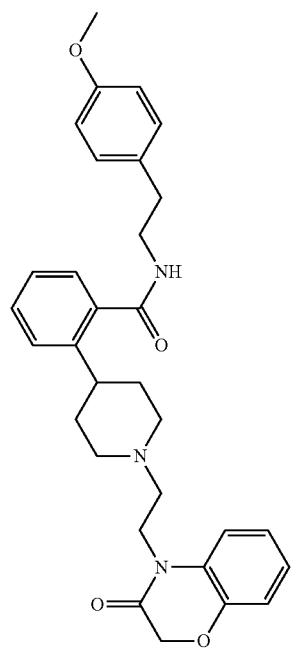
Cpd 15
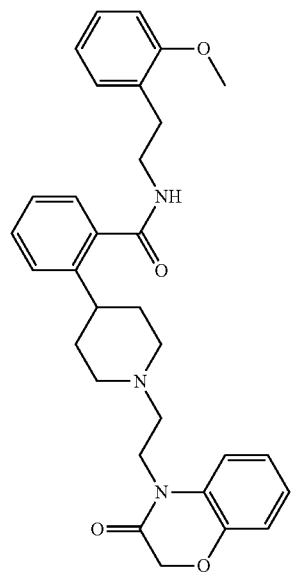
Cpd 16
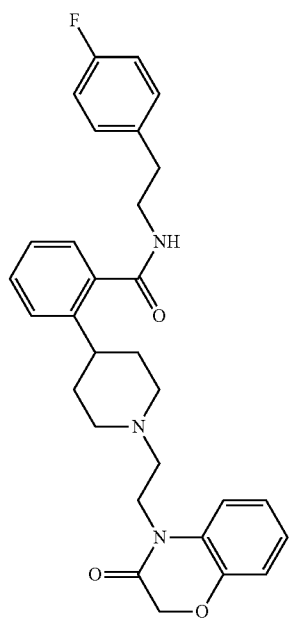
Cpd 17
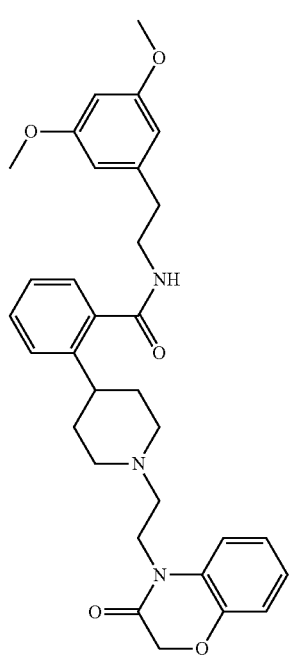

Cpd 18
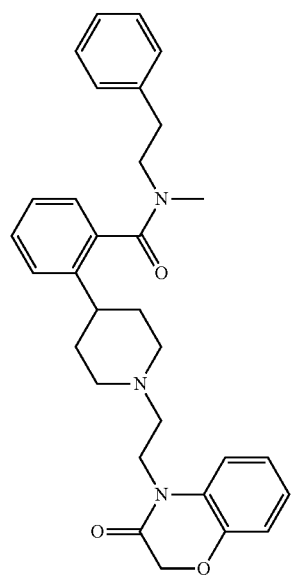
Cpd 19
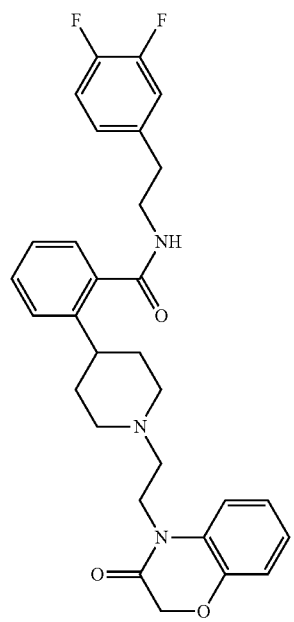
Cpd 20
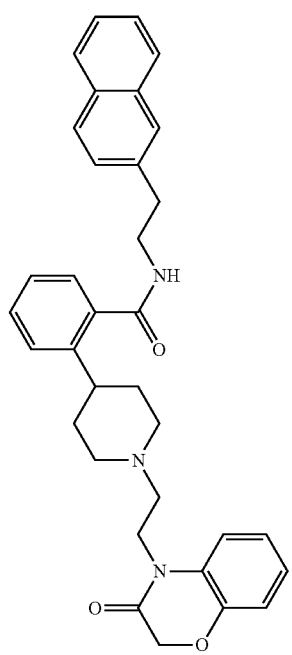
Cpd 21
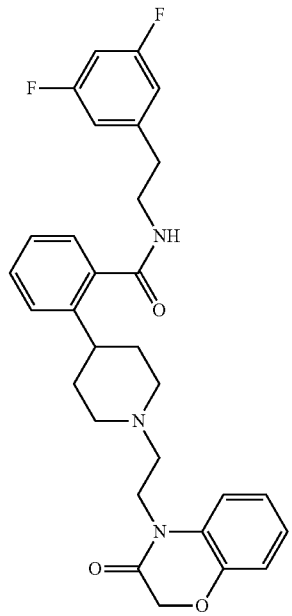

Cpd 22
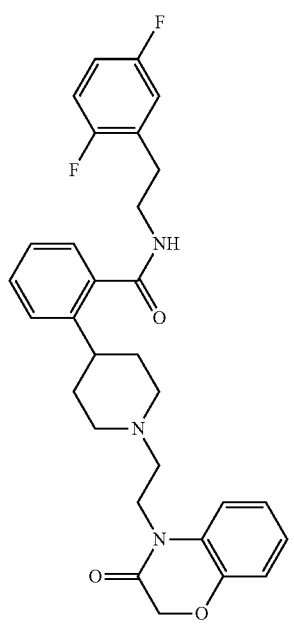
Cpd 24
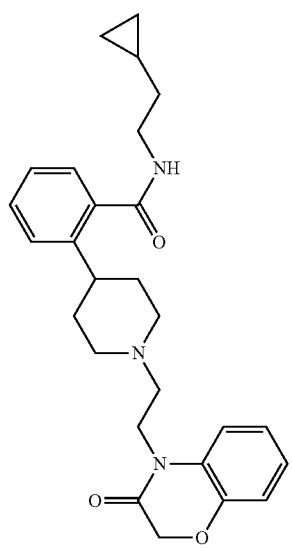
Cpd 23
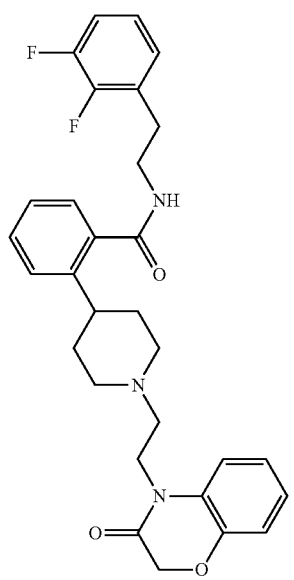
Cpd 25
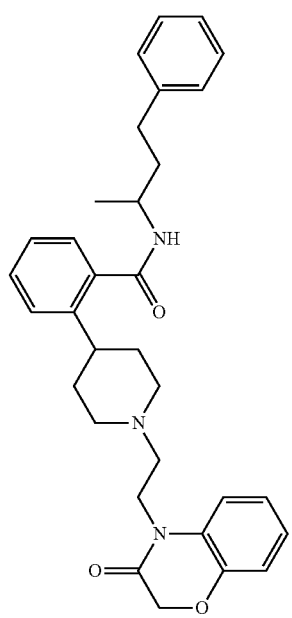

Cpd 26
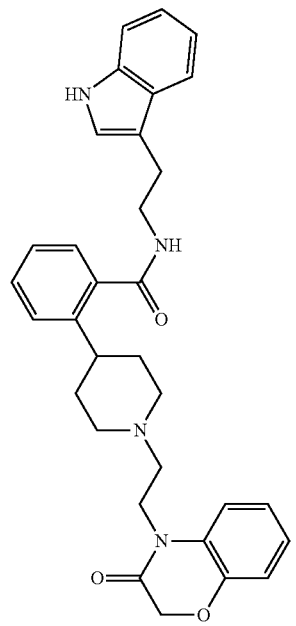
Cpd 27
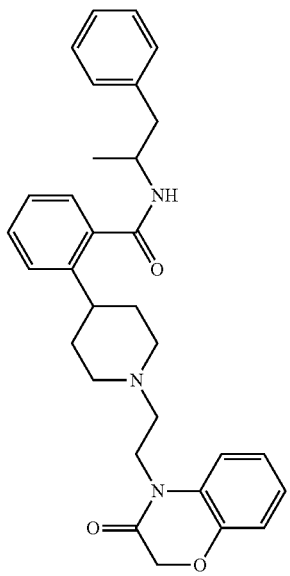
Cpd 28
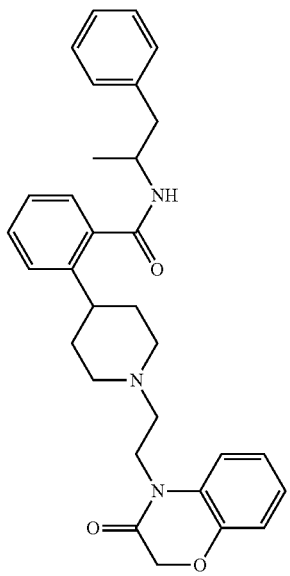
Cpd 29
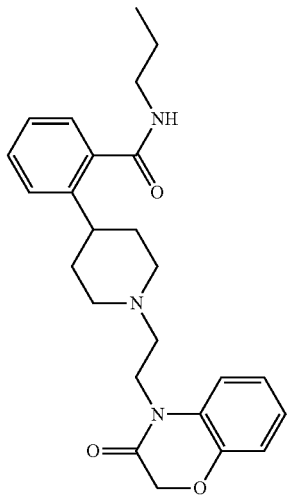
Cpd 30
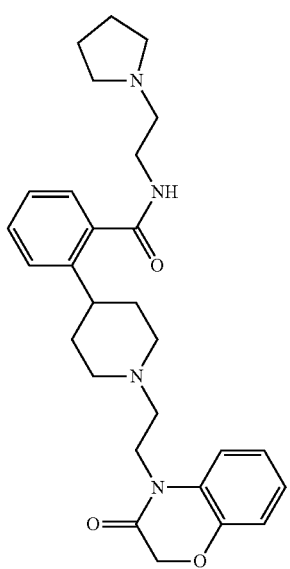

Cpd 31
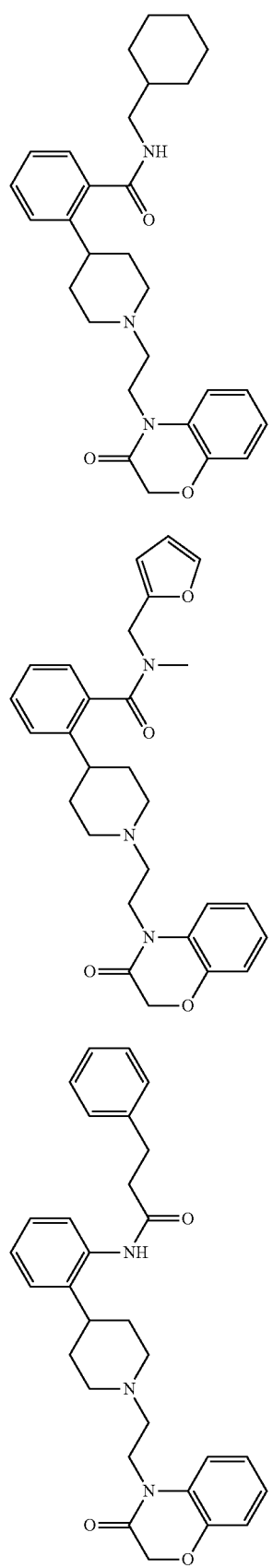
Cpd 32
Cpd 33
Cpd 34
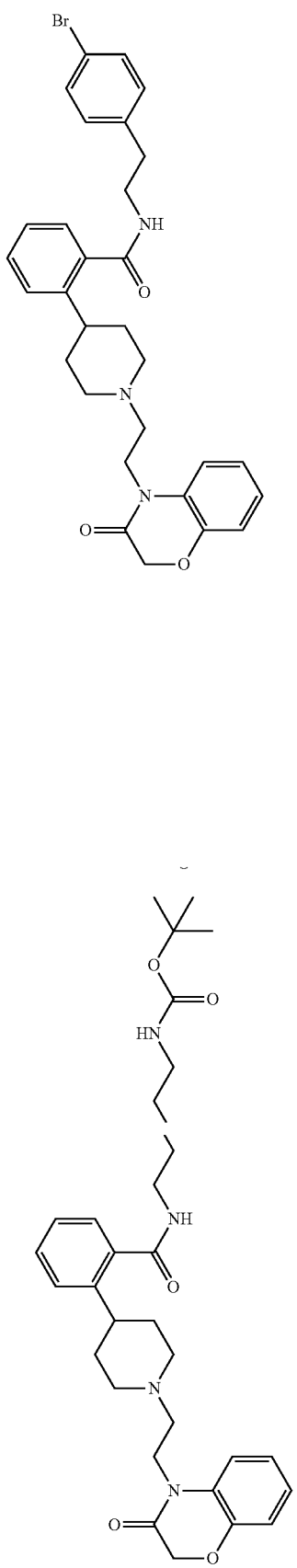
Cpd 35

Cpd 36
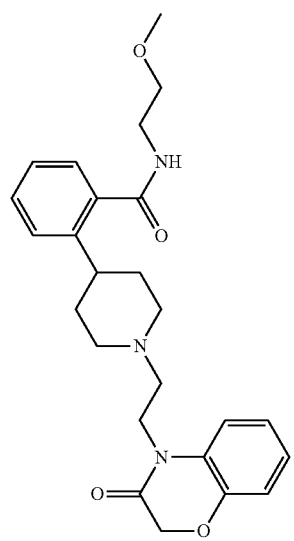
Cpd 37
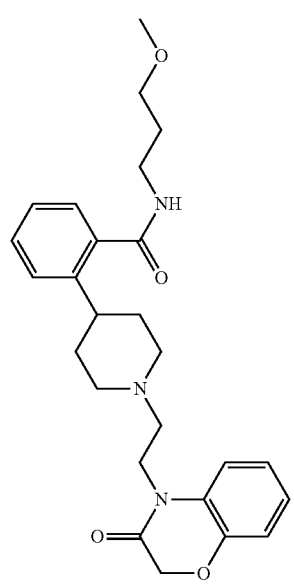
Cpd 38
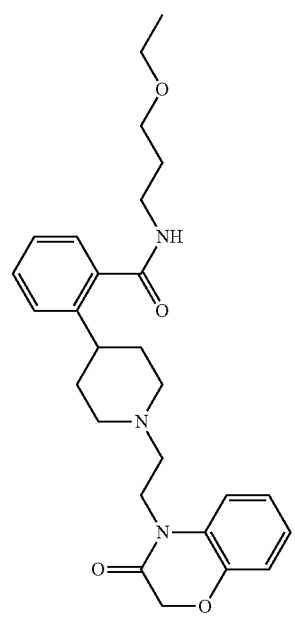
Cpd 39
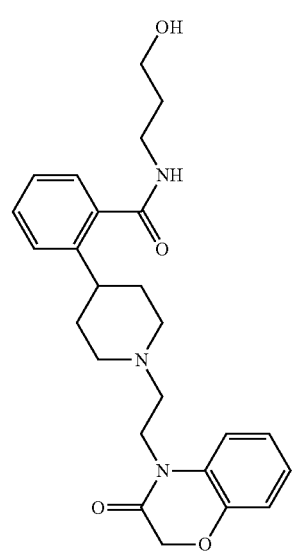

Cpd 40
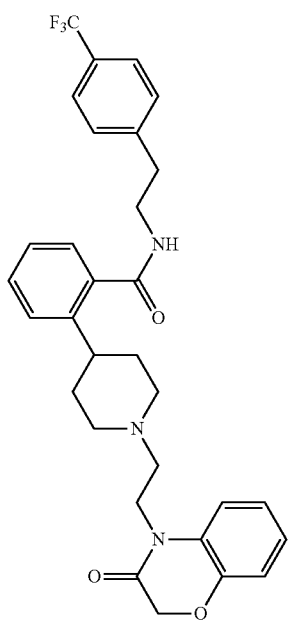
Cpd 41
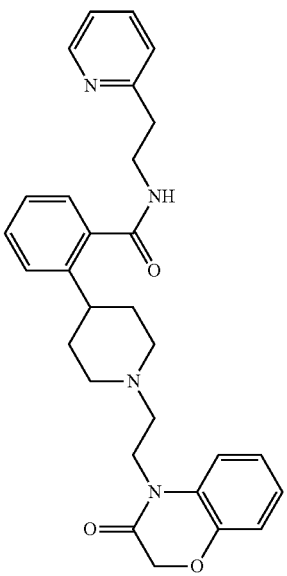
Cpd 42
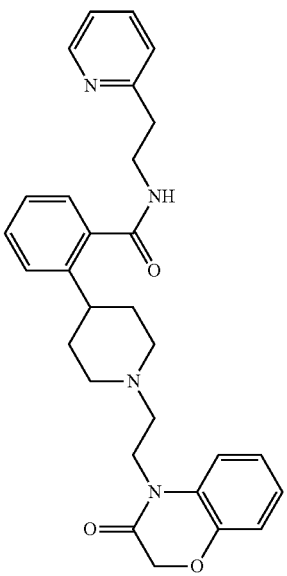
Cpd 43
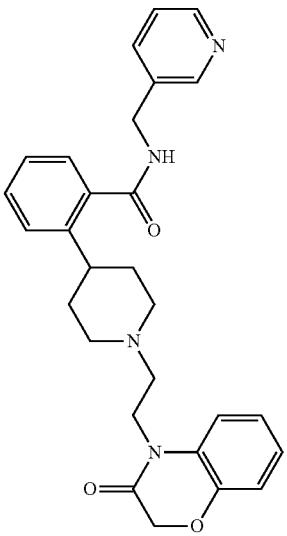
Cpd 44
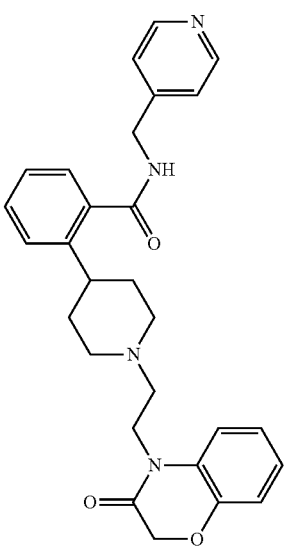

Cpd 45
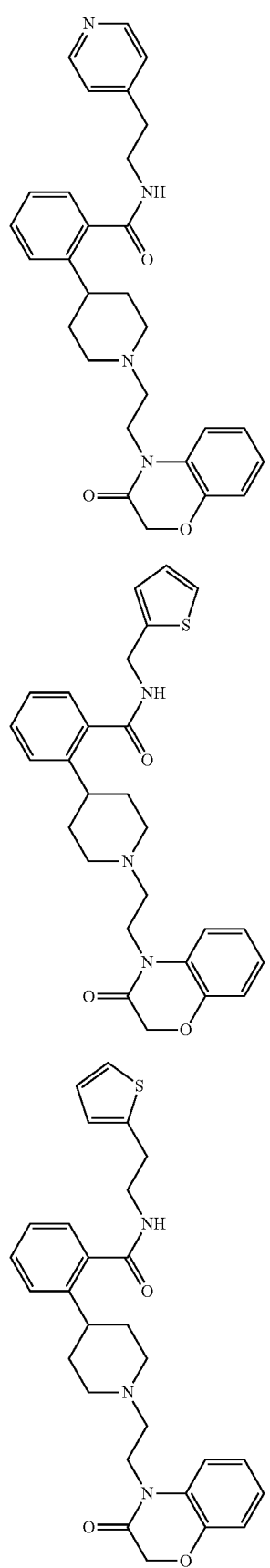
Cpd 46
Cpd 47
Cpd 48
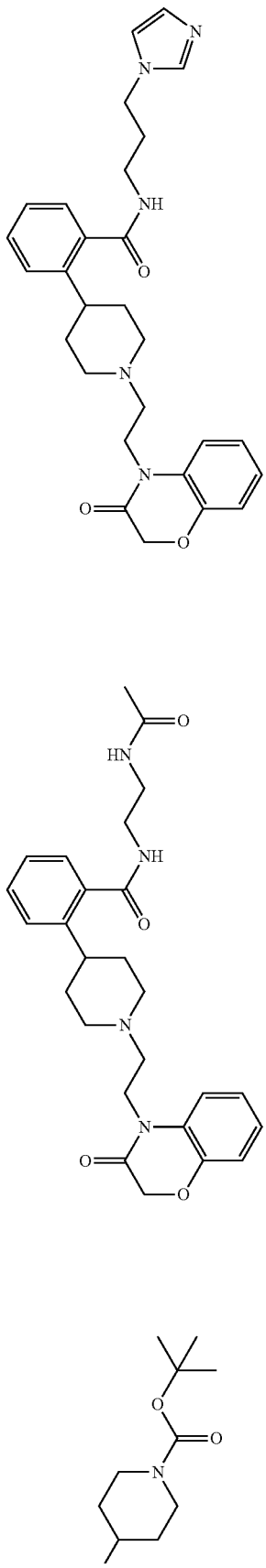
Cpd 49
Cpd 50

-continued
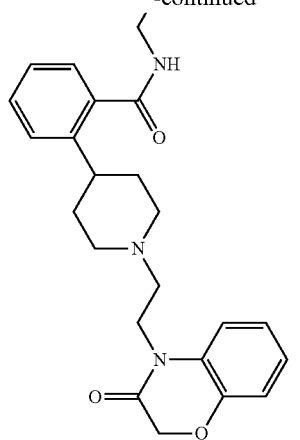
Cpd 51
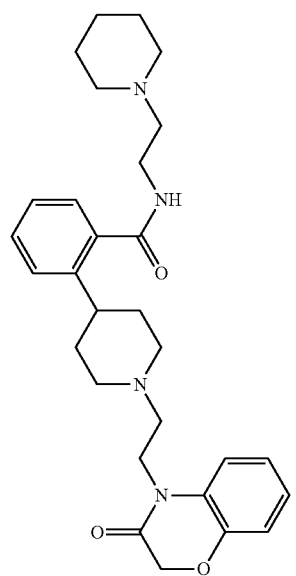
Cpd 52
-continued
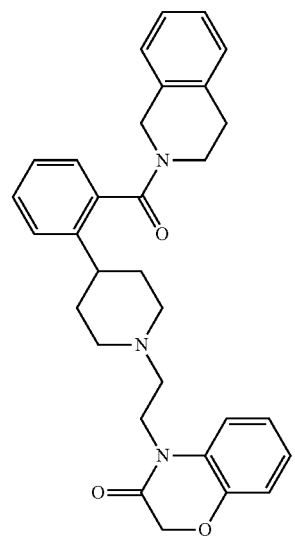
Cpd 53
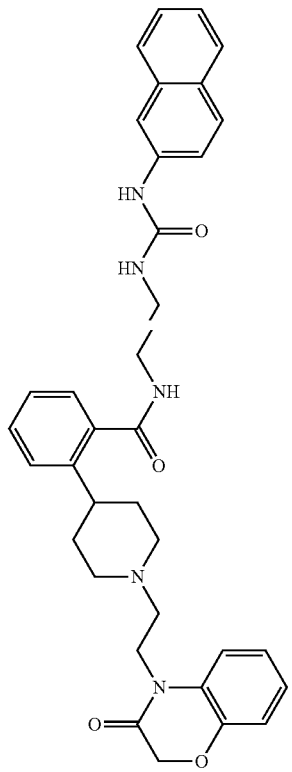
Cpd 54
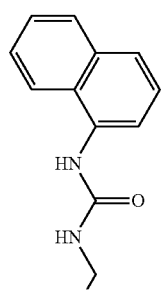
Cpd 55

-continued
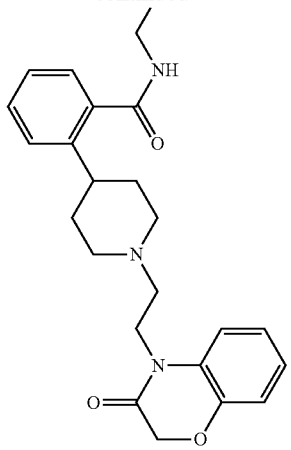
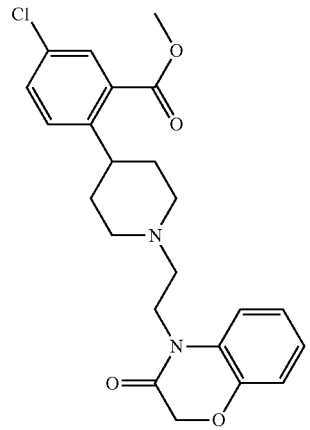
Cpd 56
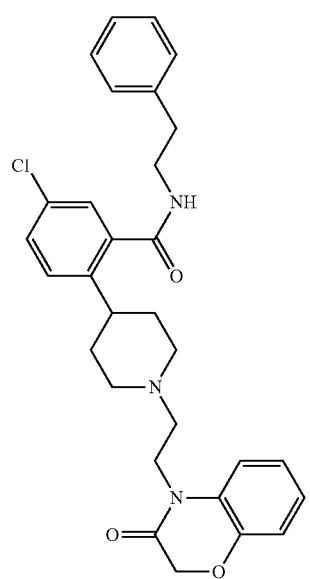
Cpd 57
-continued
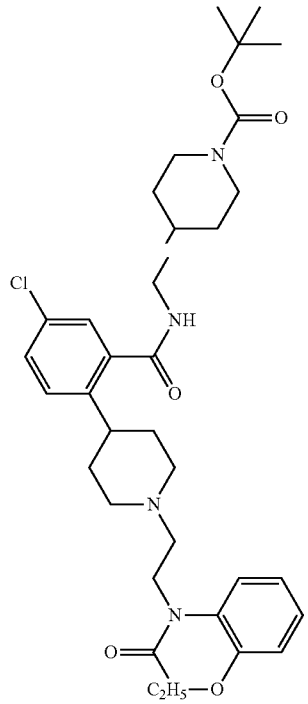
Cpd 58
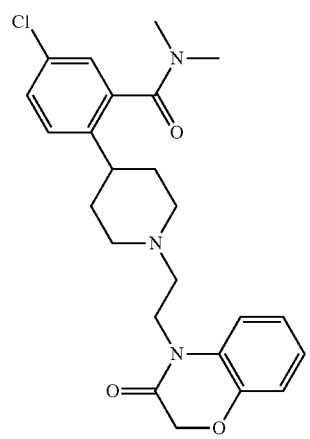
Cpd 59
Cpd 60

-continued
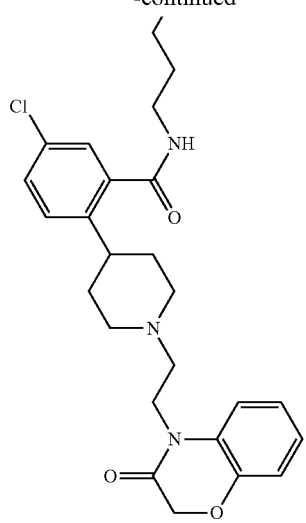
Cpd 61
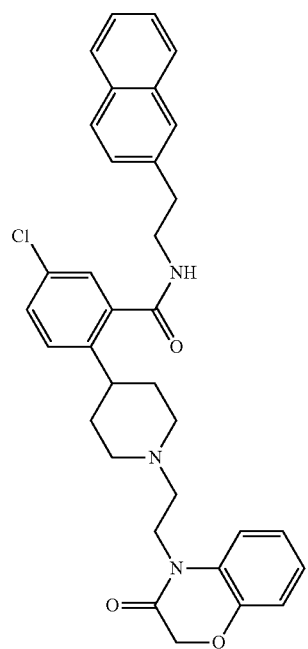
-continued
Cpd 62
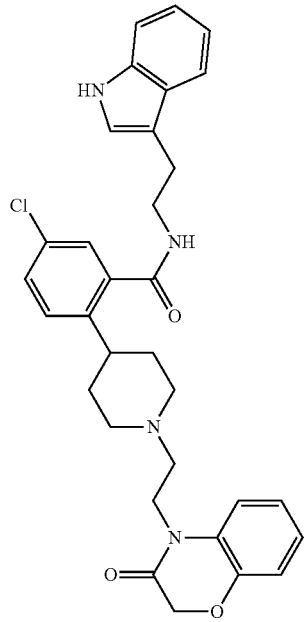
Cpd 63
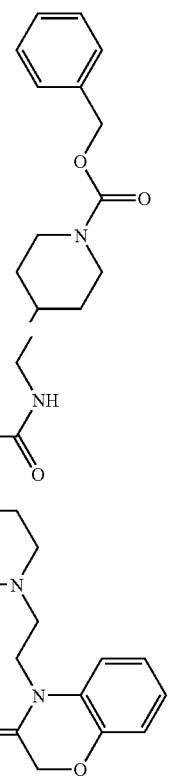
Cpd 64
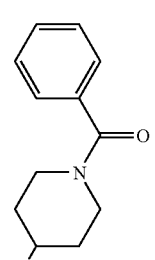

43
-continued
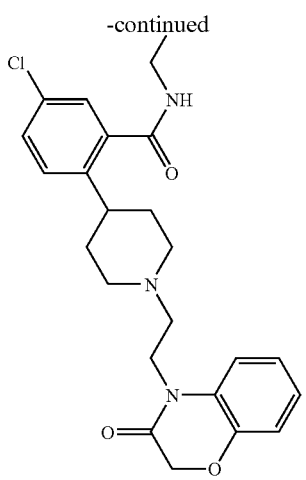
44
-continued
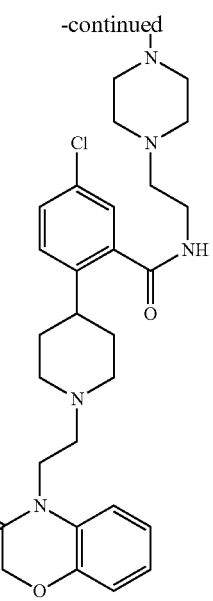
Cpd 65
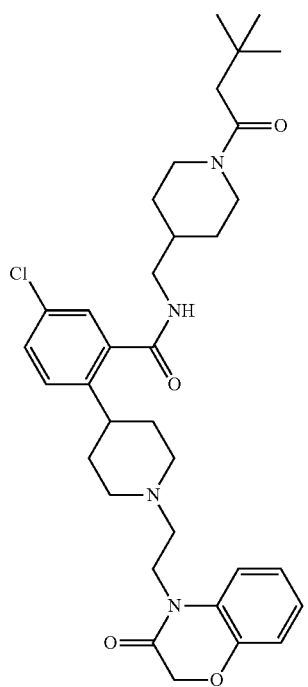
Cpd 67
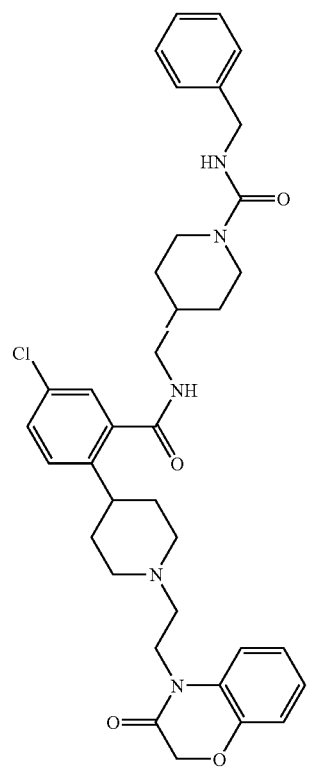
Cpd 66
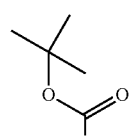
Cpd 68
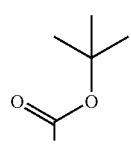

-continued
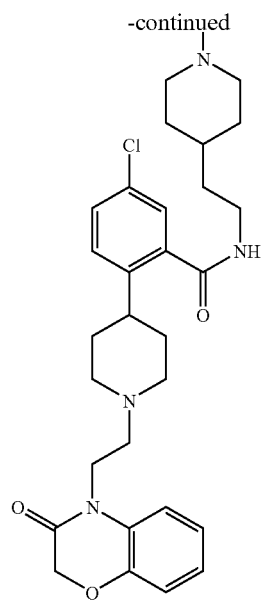
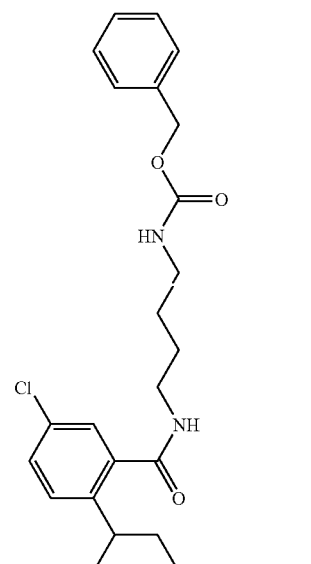
Cpd 70
-continued
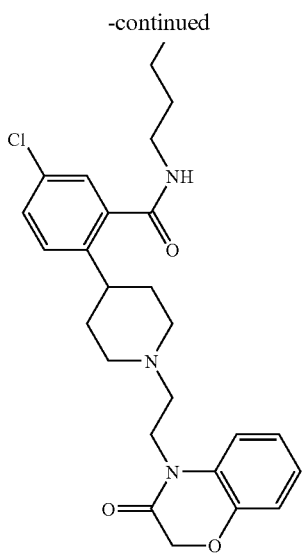
Cpd 71
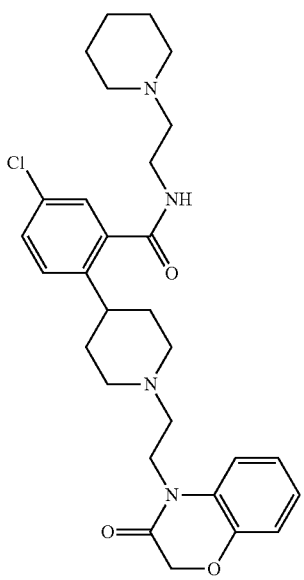
Cpd 72
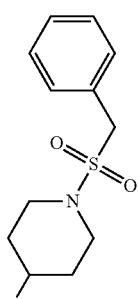

-continued
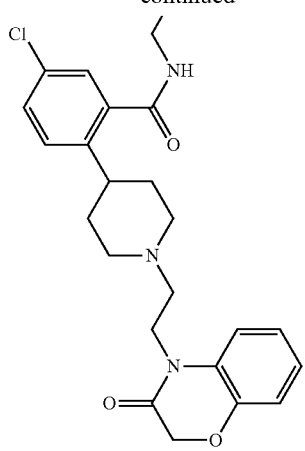
Cpd 73
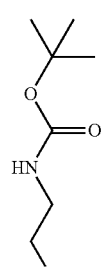
Cpd 74
-continued
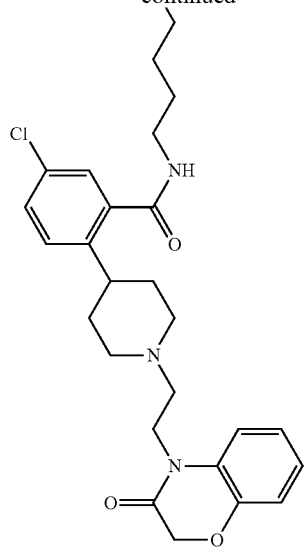
Cpd 75
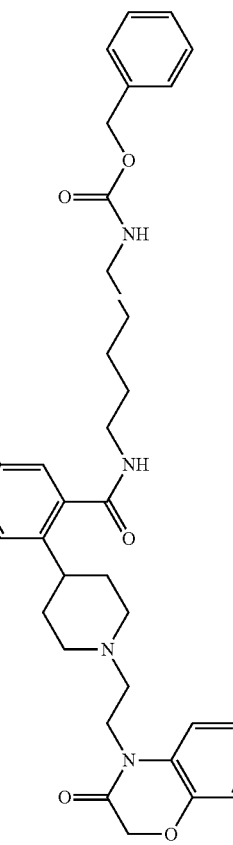
Cpd 76
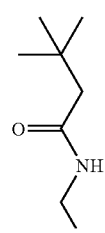

-continued
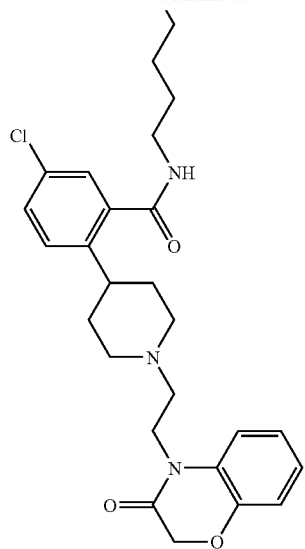
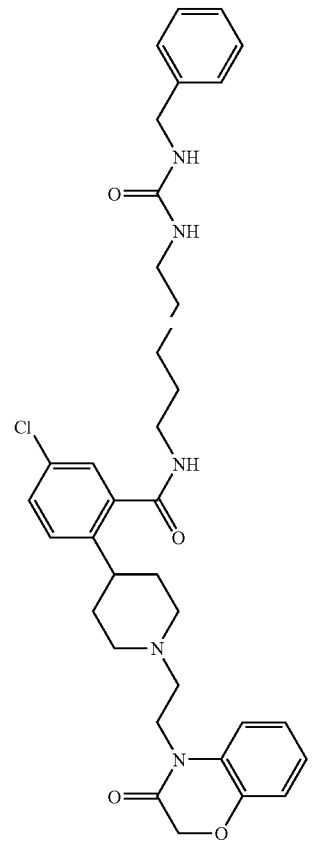
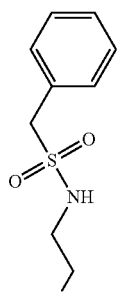
-continued
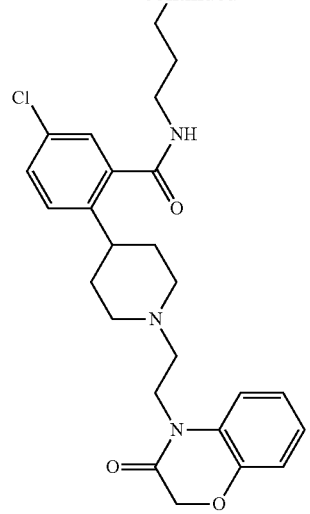
Cpd 77
Cpd 79
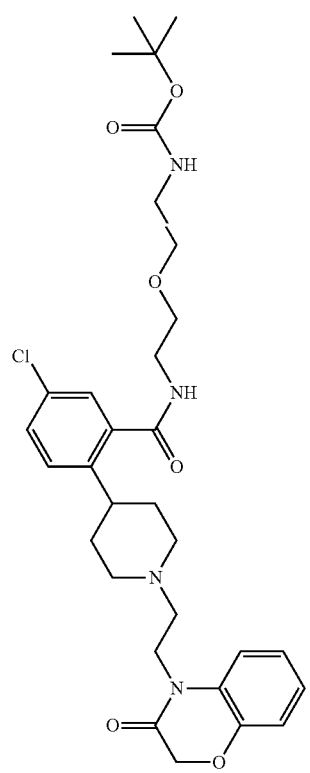
Cpd 78
Cpd 80
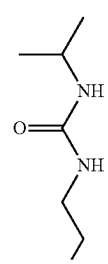

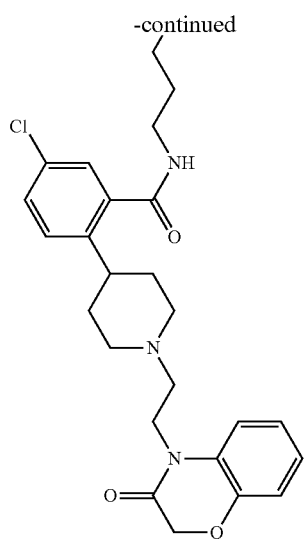
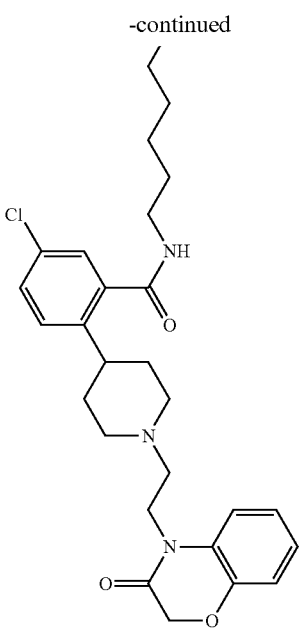
Cpd 81
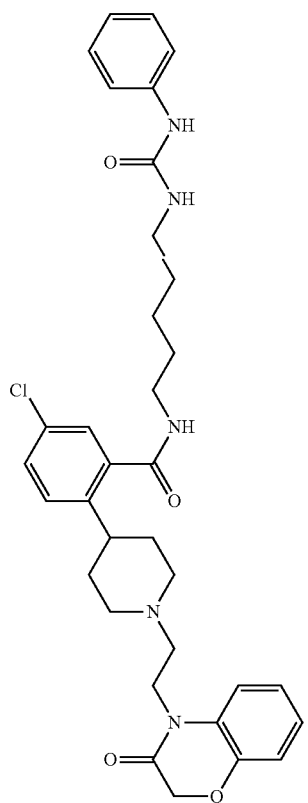
Cpd 83
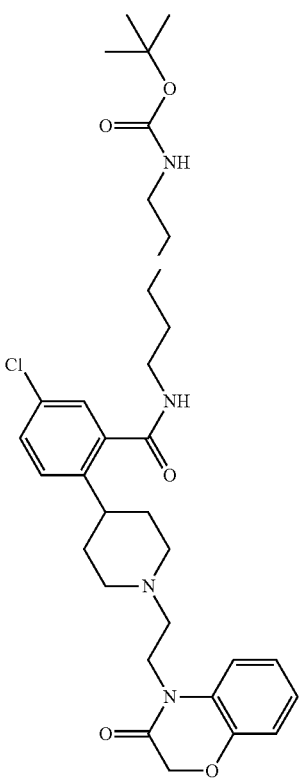
Cpd 82
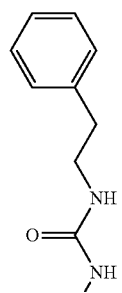
Cpd 84
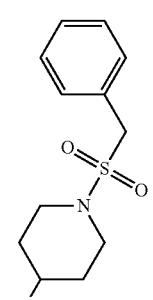

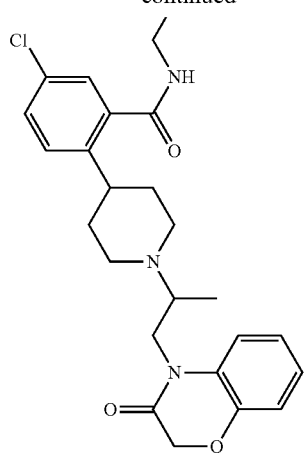
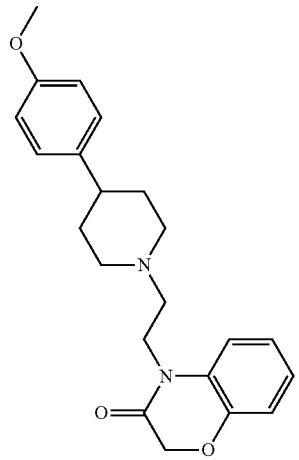
Cpd 87
Cpd 85
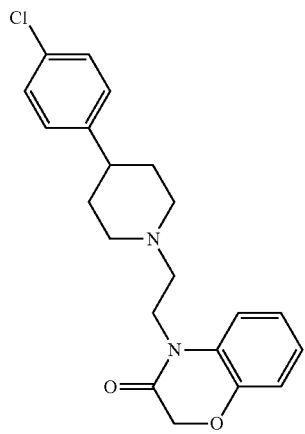
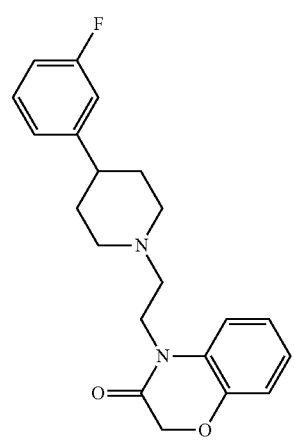
Cpd 88
Cpd 86
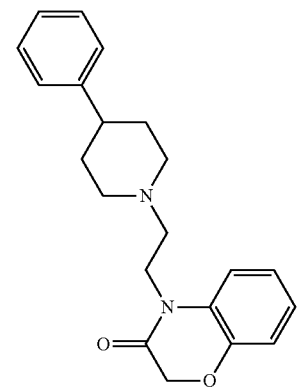
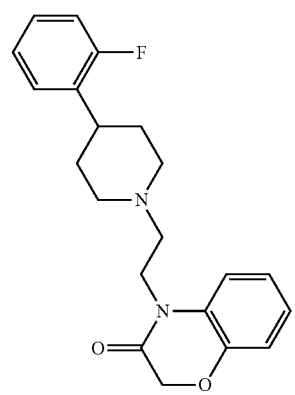
Cpd 89

Cpd 90
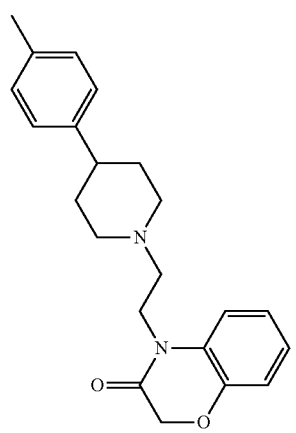
Cpd 93
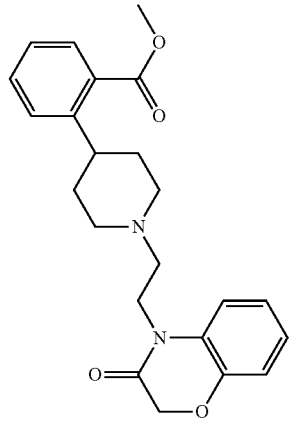
Cpd 91
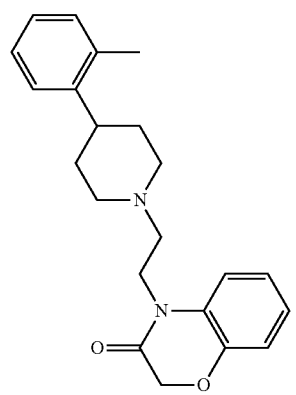
Cpd 94
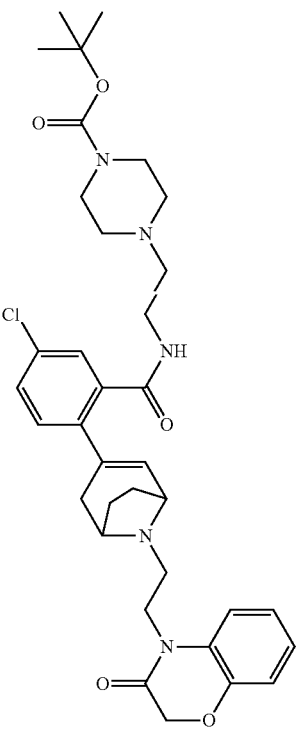
Cpd 92
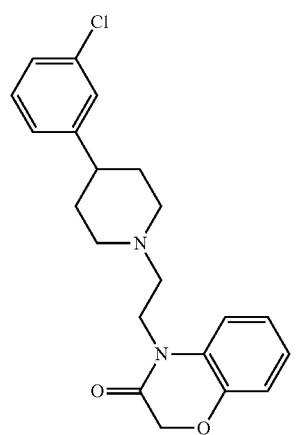
Cpd 95
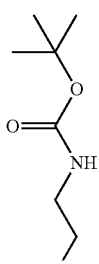

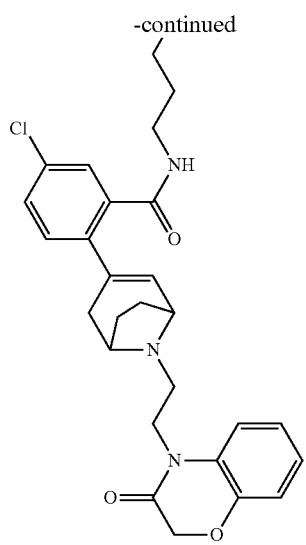
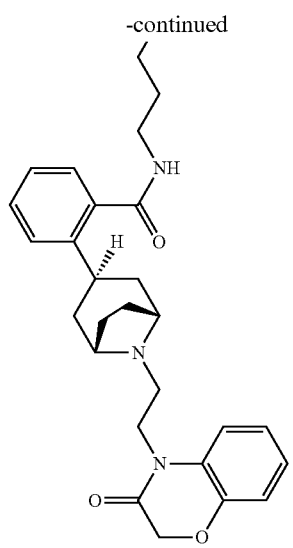
Cpd 96
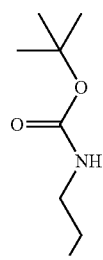
Cpd 98
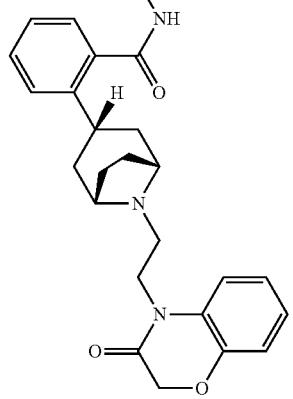
Cpd 97
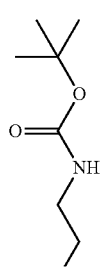
Cpd 99

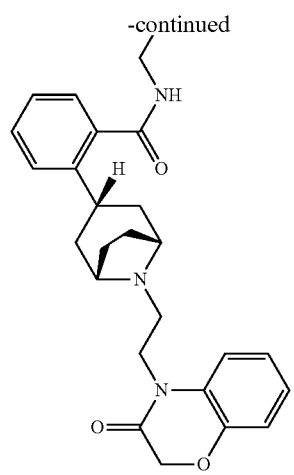
Cpd 100
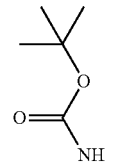
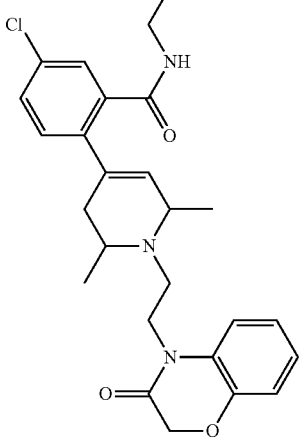
Cpd 102
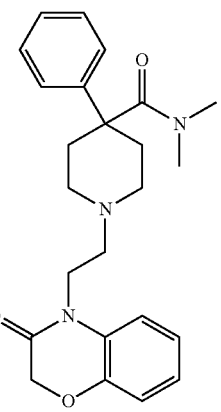
Cpd 103
Cpd 101
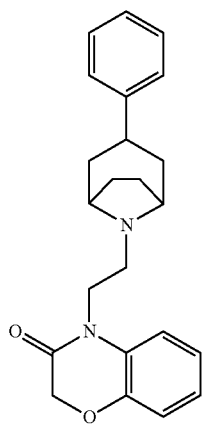
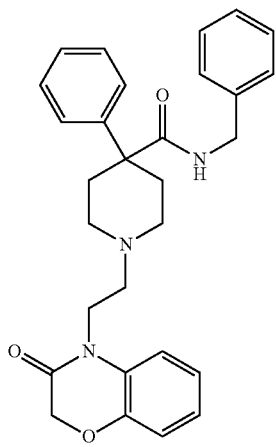
Cpd 104

Cpd 105
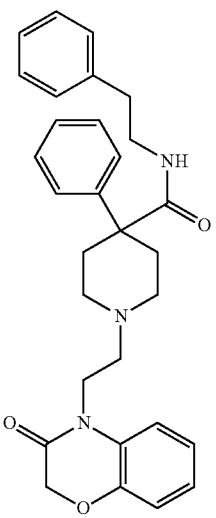
Cpd 106
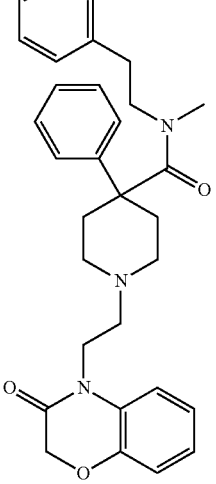
Cpd 107
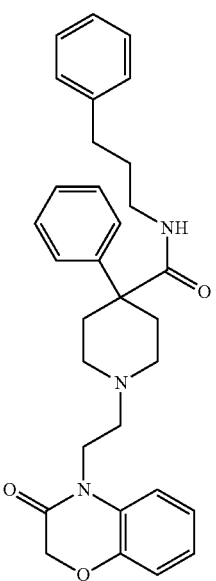
Cpd 108
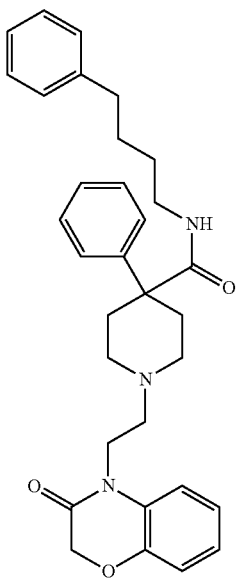
Cpd 109
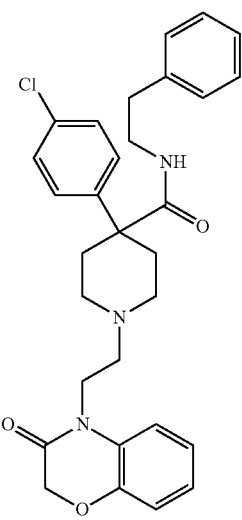
Cpd 110
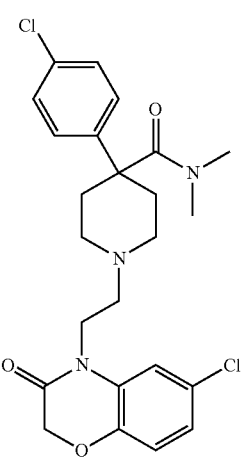

Cpd 111 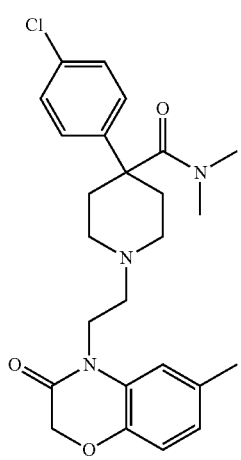

Cpd 112 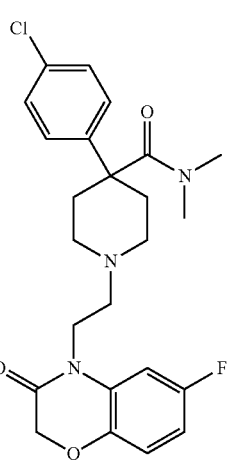

Cpd 113 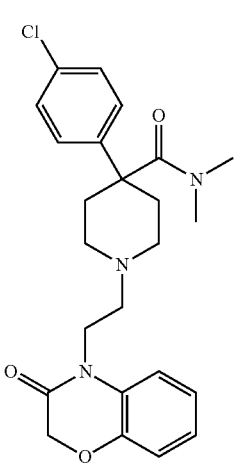

114 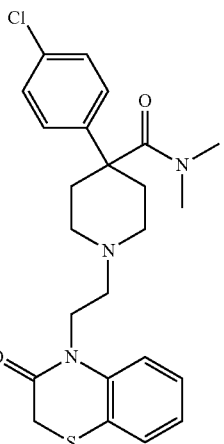

115 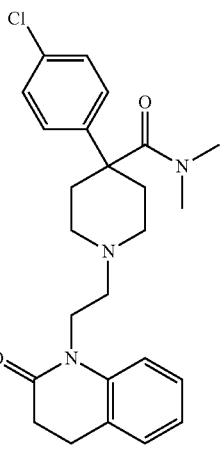

116 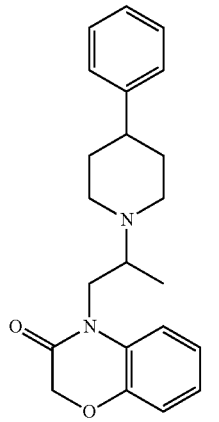

DEFINITIONS

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl" refers to straight and branched carbon chains having 1 to 8 carbon atoms or any number within this range. Therefore, designated numbers of carbon atoms (e.g. $C_{1-8}$) shall refer independently to the number of carbon atoms in the chain. A $C_{1-8}$alkyl chain may be attached to a core molecule and further substituted on any atom when allowed by available valences.

The term "$C_{1-8}$alkoxy" refers to a —O—$C_{1-8}$alkyl substituent group, wherein $C_{1-8}$alkyl is as defined supra. An $C_{1-8}$alkoxy chain may be attached to a core molecule and further substituted on any atom when allowed by available valences.

The term "$C_{3-14}$cycloalkyl" refers to saturated or partially unsaturated, monocyclic or polycyclic hydrocarbon rings of from 3 to 14 carbon atom ring members which may be optionally fused to a benzene ring. The term "$C_{3-14}$cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl or benzofused-$C_{3-12}$cycloalkyl ring system radical and the like, including, but not limited to, cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, adamantyl and the like. Cycloalkyl may be attached to a core molecule and further substituted on any atom when allowed by available valences.

The term "heterocyclyl" refers to a saturated or partially unsaturated, monocyclic or polycyclic ring of 5 to 9 members in which up to 4 members are nitrogen, or in which one or two members are nitrogen and one other member is O or S, or in which one member is O, S, S(O) or S(O)$_2$ and which may be optionally fused to a benzene ring.

Examples of heterocyclyl groups include, and are not limited to, azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, 8-aza-bicyclo[3.2.1]oct-2-enyl, 8-aza-bicyclo[3.2.1]octyl, 1,2,3,6-tetrahydro-pyridinyl and the like.

The term "heterocyclyl" also includes a benzofused-heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like. A heterocyclyl radical may be attached to a core molecule and further substituted on any atom when allowed by available valences.

The term "benzofused-heterocyclyl" means a heterocyclyl ring system radical having a benzene ring fused on the ring system on adjacent carbons. A benzofused-heterocyclyl radical may be attached to a core molecule and further substituted on any atom when allowed by available valences.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring).

Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like.

The term "heteroaryl" also includes a benzofused-heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. A heteroaryl radical may be attached to a core molecule and further substituted on any atom when allowed by available valences.

The term "benzofused-heteroaryl" means a heteroaryl ring system radical having a benzene ring fused on the ring system on adjacent carbons. A benzofused-heteroaryl radical may be attached to a core molecule and further substituted on any atom when allowed by available valences.

The term "aryl-$C_{1-8}$alkyl" means a radical of the formula: —$C_{1-8}$alkyl-aryl (e.g., benzyl, phenethyl). Similarly, the term "aryl-$C_{1-8}$alkoxy" means a radical of the formula: —$C_{1-8}$alkoxy-aryl (e.g., benzyloxy).

The term "$C_{3-14}$cycloalkyl-$C_{1-8}$alkyl" means a radical of the formula: —$C_{1-8}$alkyl-$C_{3-14}$cycloalkyl.

The term "heterocyclyl-$C_{1-8}$alkyl" means a radical of the formula: —$C_{1-8}$alkyl-heterocyclyl.

The term "heteroaryl-$C_{1-8}$alkyl" means a radical of the formula: —$C_{1-8}$alkyl-heteroaryl.

The term "$C_{1-8}$alkyl-carbonyl" means a radical of the formula: —C(O)—$C_{1-8}$alkyl.

The term "$C_{1-8}$alkoxy-carbonyl" means a radical of the formula: —C(O)—$C_{1-8}$alkoxy.

The term "aryl-carbonyl" means a radical of the formula: —C(O)-aryl.

The term "aryl-$C_{1-8}$alkyl-carbonyl" means a radical of the formula: —C(O)—$C_{1-8}$alkyl-aryl.

The term "aryl-$C_{1-8}$alkoxy-carbonyl" means a radical of the formula: —C(O)—$C_{1-8}$alkoxy-aryl.

The term "aryl-$C_{1-8}$alkyl-N($R_5$)-carbonyl" means a radical of the formula: —C(O)—N($R_5$)—$C_{1-8}$alkyl-aryl.

The term "aryl-$C_{1-8}$alkyl-sulfonyl" means a radical of the formula: —SO$_2$—$C_{1-8}$alkyl-aryl.

The term "$C_{1-8}$alkyl-N($R_5$)-carbonyl" means a radical of the formula: —C(O)—N($R_5$)—$C_{1-8}$alkyl.

The term "aryl-N($R_5$)-carbonyl" means a radical of the formula: —C(O)—N($R_5$)-aryl.

The term "halogen" or "halo" means the group chloro, bromo, fluoro or iodo.

The term "halo-$C_{1-8}$alkyl" means a radical of the formula: —$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "substituted" means the independent replacement of one or more hydrogen atoms within a radical with that amount of substituents allowed by available valences.

The term "dependently selected" means that the structure variables are specified in an indicated combination.

In general, IUPAC nomenclature rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, ammonium, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, edisylate, estolate, esylate, fumarate, gluconate, gluceptate, glutamate, glyconate, glycollylarsanilate, hexylresorcinate, hydrabamine, hydrobromide, hydrochloride, hydroxynaphthoate, iodide, isothionate, lactate, lactobionate, laurate, malate, maleate, malonate, mandelate, mesylate, methylbromide, methylnitrate, methylsulfate, mucate, napsylate, nitrate, N-methylglucamine, oleate, pamoate (embonate), palmitate, pantothenate, phosphate/diphosphate, polygalacturonate, saccharinate, salicylate, stearate, sulfate, subacetate, succinate, tannate, tartrate, teoclate, tosylate, trichloroacetate, triethiodide, trifluoroacetate, valerate and the like.

Representative acids and bases which may be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, compounds of the present invention may have one or more crystalline polymorph or amorphous forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Where the processes for the preparation of the compounds according to the invention give rise to mixture of stereoisomers, these isomers may be separated using various well known chromatographic methods such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention is also directed to a method for treating or ameliorating a Urotensin-II mediated disorder.

An example of the method of the present invention is a method for treating or ameliorating a disease or condition in a mammal which disease or condition is affected by antagonism of a Urotensin II receptor, which method comprises administering to the mammal in need of such treatment or prevention an effective amount of a compound of Formula (I):

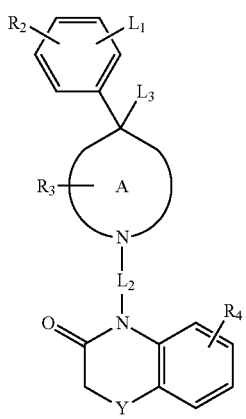

and forms thereof, wherein

Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —NH$R_6$, wherein $C_{1-8}$alkoxy is optionally substituted with one, two or three substituents each selected from the group consisting of $C_{1-8}$alkoxy, halogen, hydroxy and —NH$R_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl.

Another example of the method of the present invention is a method for treating or ameliorating a Urotensin-II mediated disorder in a subject in need thereof comprising administering to the subject an effective amount of a compound of Formula (I) or a form thereof.

In particular, a Urotensin II-mediated disorder includes, and is not limited to, chronic vascular disease, vascular hypertension, heart failure, atherosclerosis, inflammatory bowel disease, Crohn's disease, ulcerative colitis, inflammatory colitis (caused by bacteria, ischemia, radiation, drugs or chemical substances), renal dysfunction, renal failure, renal failure caused by drug induced toxicity, nephrotoxicity and diarrhea caused by anti-neoplastic agents, nephrotoxicity caused by radiocontrast agents and aminoglycosides, postmyocardial infarction, pulmonary hypertension, pulmonary fibrosis, insulin resistance and impaired glucose tolerance, diabetes, diabetic complications, diabetic nephropathy, pain, Alzheimer's disease, convulsions, depression, migraine, psychosis, anxiety, neuromuscular deficit and stroke.

The present invention also includes the use of the compound of formula (I) or a form thereof for the manufacture of a medicament for treating or ameliorating a Urotensin-II mediated disorder in a subject in need thereof.

An example of the present invention includes a method for treating or ameliorating a Urotensin-II mediated disorder, wherein the disorder is heart failure.

The term "medicament" refers to a product for use in treating or ameliorating a Urotensin-II mediated disorder.

The term "subject" as used herein, refers to an animal, preferably a mammal, most preferably a human, who has been a patient or the object of treatment, observation or experiment.

The term "effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The effective amount of said compound or form thereof is from about 0.001 mg/kg/day to about 300 mg/kg/day.

As used herein, the term "composition" is intended to encompass a product comprising the specified ingredients in the specified amounts, as well as any product which results, directly or indirectly, from combinations of the specified ingredients in the specified amounts.

As used herein, the term "neoplasm" refers to an abnormal growth of cells or tissue and is understood to include benign, i.e., non-cancerous growths, and malignant, i.e., cancerous growths. The term "neoplastic" means of or related to neoplasm.

As used herein, the term "agent" is understood to mean a substance that produces a desired effect in a tissue, system, animal, mammal (in particular human), or other subject. Accordingly, the term "anti-neoplastic agent" is understood to mean a substance producing an anti-neoplastic effect in a tissue, system, animal, mammal (in particular human), or other subject. It is understood that an "agent" may be a single compound or a combination or composition of two or more compounds.

Some of the typical anti-neoplastic agents include alkylating agents such as melphalan, chlorambucil, cyclophosphamide, mechlorethamine, hexamethylmelamine, busulfan, carmustine, lomustine, and dacarbazine; antimetabolites such as 5-fluorouracil, methotrexate, cytarabine, mercaptopurine, and thioguanine; antimitotic agents such as paclitaxel, docetaxel, vinblastine, vincristine; topoisomerase I inhibitors such as irinotecan, camptothecin and camptothecin derivatives, for example topotecan; topoisomerase II inhibitors such as doxorubicin; and platinum coordination complexes such as cisplatin and carboplatin.

An embodiment of the present invention is a method for treating a U-II mediated disorder including, but not limited to, vascular hypertension, heart failure, atherosclerosis, renal failure, renal failure caused by drug induced toxicity, nephrotoxicity and diarrhea caused by anti-neoplastic agents, nephrotoxicity caused by radiocontrast agents and aminoglycosides, post-myocardial infarction, pulmonary hypertension, pulmonary fibrosis, insulin resistance and impaired glucose tolerance, diabetes, diabetic complications, diabetic nephropathy, depression, psychosis, anxiety and stroke.

The present method of using Urotensin II receptor antagonists to reduce anti-neoplastic agent induced diarrhea and nephrotoxicity is applicable in any situation when anti-neoplastic agents (such as cisplatin, cis-diaminedichloroplatinum) are being administered to treat cancers or tumors. However, most often UII antagonists are used when tumors or cancers being treated are those of solid malignancies, notably those of the bladder, cervix, lung, ovary, and testis such as testicular tumor, bladder cancer, ureterpyelonephritic tumor, prostatic cancer, ovarian cancer, head and neck cancer, non-small-cell lung cancer, esophageal cancer, cervical cancer, neuroblastoma, gastric cancer, small cell lung cancer, bone cancer, non-Hodgkin's lymphomas, tumors of brain, endometrium, upper gastrointestinal tract, head and neck and thymus, neuroblastoma and sarcoma of bone and soft tissue.

Recent data has demonstrated that Urotensin II receptor antagonists may be useful for improving cardiac function and for cardiac remodeling associated with chronic heart failure (CHF) (N. Bousette, F. Hu, E. H. Ohlstein, D. Dhanak, S. A. Douglas, A. Giaid, *Journal of Molecular and Cellular Cardiology* 2006, In Press). Long-term treatment of streptozotocin-induced diabetic rats with palosuran improved survival, increased insulin, and slowed the increase in glycemia, glycosylated hemoglobin, and serum lipids. Furthermore, palosuran increased renal blood flow and delayed the development of proteinuria and renal damage (M. Clozel, P. Hess, C. Qiu, S. S. Ding, M. Rey, J. Pharmacol. Exp. Ther. 2006, 316 (3), 1115-1121).

A therapeutically effective amount for use of the instant compounds or a pharmaceutical composition thereof comprises a dose range from about 0.1 mg to about 3000 mg, in particular from about 1 mg to about 1000 mg or, more particularly from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

Optimal dosages of the compounds of Formula (I) to be administered for the treatment of or prevention of Urotensin II mediated disorders may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

A representative compound of Formula (I) or a form thereof includes a compound selected from the group consisting of:

| Cpd | Name |
| --- | --- |
| 1 | 2-{1-[2-(3-oxo-2,3-dihydro-benzo[1,4]oxazin-4-yl)-ethyl]-piperidin-4-yl}-N-phenethyl-benzamide, |
| 2 | N-benzyl-2-{1-[2-(3-oxo-2,3-dihydro-benzo[1,4]oxazin-4-yl)-ethyl]-piperidin-4-yl}-benzamide, |
| 3 | 2-{1-[2-(3-oxo-2,3-dihydro-benzo[1,4]oxazin-4-yl)-ethyl-piperidin-4-yl}-N-(3-phenyl-propyl)-benzamide, |
| 4 | 2-{1-[2-(3-oxo-2,3-dihydro-benzo[1,4]oxazin-4-yl)-ethyl-piperidin-4-yl}-N-(4-phenyl-butyl)-benzamide, |
| 5 | N-benzyl-N-methyl-2-{1-[2-(3-oxo-2,3-dihydro-benzo[1,4]oxazin-4-yl)-ethyl]-piperidin-4-yl}-benzamide, |
| 6 | N-[2-(3-methoxy-phenyl)-ethyl]-2-{1-[2-(3-oxo-2,3-dihydro-benzo[1,4]oxazin-4-yl)-ethyl]-piperidin-4-yl}-benzamide, |
| 7 | N-[2-(2,4-dichloro-phenyl)-ethyl]-2-{1-[2-(3-oxo-2,3-dihydro-benzo[1,4]oxazin-4-yl)-ethyl]-piperidin-4-yl}-benzamide, |
| 8 | N-[2-(2-chloro-phenyl)-ethyl]-2-{1-[2-(3-oxo-2,3-dihydro-benzo[1,4]oxazin-4-yl)-ethyl]-piperidin-4-yl}-benzamide, |
| 9 | N-[2-(4-chloro-phenyl)-ethyl]-2-{1-[2-(3-oxo-2,3-dihydro-benzo[1,4]oxazin-4-yl)-ethyl]-piperidin-4-yl}-benzamide, |
| 10 | N-[2-(3,4-dimethoxy-phenyl)-ethyl]-2-{1-[2-(3-oxo-2,3-dihydro-benzo[1,4]oxazin-4-yl)-ethyl]-piperidin-4-yl}-benzamide, |
| 11 | N-[2-(3,4-dichloro-phenyl)-ethyl]-2-{1-[2-(3-oxo-2,3-dihydro-benzo[1,4]oxazin-4-yl)-ethyl]-piperidin-4-yl}-benzamide, |
| 12 | N-[2-(4-chloro-phenyl)-1-methyl-ethyl]-2-{1-[2-(3-oxo-2,3-dihydro-benzo[1,4]oxazin-4-yl)-ethyl]-piperidin-4-yl}-benzamide, |
| 13 | N-[2-(2,5-dimethoxy-phenyl)-ethyl]-2-{1-[2-(3-oxo-2,3-dihydro-benzo[1,4]oxazin-4-yl)-ethyl]-piperidin-4-yl}-benzamide, |
| 14 | N-[2-(4-methoxy-phenyl)-ethyl]-2-{1-[2-(3-oxo-2,3-dihydro-benzo[1,4]oxazin-4-yl)-ethyl]-piperidin-4-yl}-benzamide, |
| 15 | N-[2-(2-methoxy-phenyl)-ethyl]-2-{1-[2-(3-oxo-2,3-dihydro-benzo[1,4]oxazin-4-yl)-ethyl]-piperidin-4-yl}-benzamide, |
| 16 | N-[2-(4-fluoro-phenyl)-ethyl]-2-{1-[2-(3-oxo-2,3-dihydro-benzo[1,4]oxazin-4-yl)-ethyl]-piperidin-4-yl}-benzamide, |
| 17 | N-[2-(3,5-dimethoxy-phenyl)-ethyl]-2-{1-[2-(3-oxo-2,3-dihydro-benzo[1,4]oxazin-4-yl)-ethyl]-piperidin-4-yl}-benzamide, |

| Cpd | Name |
|---|---|
| 18 | N-methyl-2-{1-[2-(3-oxo-2,3-dihydro-benzo[1,4]oxazin-4-yl)-ethyl]-piperidin-4-yl}-N-phenethyl-benzamide, |
| 19 | N-[2-(3,4-difluoro-phenyl)-ethyl]-2-{1-[2-(3-oxo-2,3-dihydro-benzo[1,4]oxazin-4-yl)-ethyl]-piperidin-4-yl}-benzamide, |
| 20 | N-(2-naphthalen-2-yl-ethyl)-2-{1-[2-(3-oxo-2,3-dihydro-benzo[1,4]oxazin-4-yl)-ethyl]-piperidin-4-yl}-benzamide, |
| 21 | N-[2-(3,5-difluoro-phenyl)-ethyl]-2-{1-[2-(3-oxo-2,3-dihydro-benzo[1,4]oxazin-4-yl)-ethyl]-piperidin-4-yl}-benzamide, |
| 22 | N-[2-(2,5-difluoro-phenyl)-ethyl]-2-{1-[2-(3-oxo-2,3-dihydro-benzo[1,4]oxazin-4-yl)-ethyl]-piperidin-4-yl}-benzamide, |
| 23 | N-[2-(2,3-difluoro-phenyl)-ethyl]-2-{1-[2-(3-oxo-2,3-dihydro-benzo[1,4]oxazin-4-yl)-ethyl]-piperidin-4-yl}-benzamide, |
| 24 | N-cyclopropylmethyl-2-{1-[2-(3-oxo-2,3-dihydro-benzo[1,4]oxazin-4-yl)-ethyl]-piperidin-4-yl}-benzamide, |
| 25 | N-(1-methyl-3-phenyl-propyl)-2-{1-[2-(3-oxo-2,3-dihydro-benzo[1,4]oxazin-4-yl)-ethyl]-piperidin-4-yl}-benzamide, |
| 26 | N-[2-(1H-indol-3-yl)-ethyl]-2-{1-[2-(3-oxo-2,3-dihydro-benzo[1,4]oxazin-4-yl)-ethyl]-piperidin-4-yl}-benzamide, |
| 27 | N-indan-1-yl-2-{1-[2-(3-oxo-2,3-dihydro-benzo[1,4]oxazin-4-yl)-ethyl]-piperidin-4-yl}-benzamide, |
| 28 | 2-{1-[2-(3-oxo-2,3-dihydro-benzo[1,4]oxazin-4-yl)-ethyl]-piperidin-4-yl}-N-(2-phenyl-propyl)-benzamide, |
| 29 | 2-{1-[2-(3-oxo-2,3-dihydro-benzo[1,4]oxazin-4-yl)-ethyl]-piperidin-4-yl}-N-propyl-benzamide, |
| 31 | 2-{1-[2-(3-oxo-2,3-dihydro-benzo[1,4]oxazin-4-yl)-ethyl]-piperidin-4-yl}-N-(2-pyrrolidin-1-yl-ethyl)-benzamide, |
| 32 | N-cyclohexylmethyl-2-{1-[2-(3-oxo-2,3-dihydro-benzo[1,4]oxazin-4-yl)-ethyl]-piperidin-4-yl}-benzamide, |
| 33 | N-furan-2-ylmethyl-N-methyl-2-{1-[2-(3-oxo-2,3-dihydro-benzo[1,4]oxazin-4-yl)-ethyl]-piperidin-4-yl}-benzamide, |
| 34 | N-(2-{1-[2-(3-oxo-2,3-dihydro-benzo[1,4]oxazin-4-yl)-ethyl]-piperidin-4-yl}-phenyl)-3-phenyl-propionamide, |
| 35 | [4-(2-{1-[2-(3-oxo-2,3-dihydro-benzo[1,4]oxazin-4-yl)-ethyl]-piperidin-4-yl}-benzoylamino)-butyl]-carbamic acid tert-butyl ester, |
| 36 | N-(2-methoxy-ethyl)-2-{1-[2-(3-oxo-2,3-dihydro-benzo[1,4]oxazin-4-yl)-ethyl]-piperidin-4-yl}-benzamide, |
| 37 | N-(3-methoxy-propyl)-2-{1-[2-(3-oxo-2,3-dihydro-benzo[1,4]oxazin-4-yl)-ethyl]-piperidin-4-yl}-benzamide, |
| 38 | N-(3-ethoxy-propyl)-2-{1-[2-(3-oxo-2,3-dihydro-benzo[1,4]oxazin-4-yl)-ethyl]-piperidin-4-yl}-benzamide, |
| 39 | N-(3-hydroxy-propyl)-2-{1-[2-(3-oxo-2,3-dihydro-benzo[1,4]oxazin-4-yl)-ethyl]-piperidin-4-yl}-benzamide, |
| 40 | 2-{1-[2-(3-oxo-2,3-dihydro-benzo[1,4]oxazin-4-yl)-ethyl]-piperidin-4-yl}-N-[2-(4-trifluoromethyl-phenyl)-ethyl]-benzamide, |
| 41 | 2-{1-[2-(3-oxo-2,3-dihydro-benzo[1,4]oxazin-4-yl)-ethyl]-piperidin-4-yl}-N-pyridin-2-ylmethyl-benzamide, |
| 42 | 2-{1-[2-(3-oxo-2,3-dihydro-benzo[1,4]oxazin-4-yl)-ethyl]-piperidin-4-yl}-N-(2-pyridin-2-yl-ethyl)-benzamide, |
| 43 | 2-{1-[2-(3-oxo-2,3-dihydro-benzo[1,4]oxazin-4-yl)-ethyl]-piperidin-4-yl}-N-pyridin-3-ylmethyl-benzamide, |
| 44 | 2-{1-[2-(3-oxo-2,3-dihydro-benzo[1,4]oxazin-4-yl)-ethyl]-piperidin-4-yl}-N-pyridin-4-ylmethyl-benzamide, |
| 45 | 2-{1-[2-(3-oxo-2,3-dihydro-benzo[1,4]oxazin-4-yl)-ethyl]-piperidin-4-yl}-N-(2-pyridin-4-yl-ethyl)-benzamide, |
| 46 | 2-{1-[2-(3-oxo-2,3-dihydro-benzo[1,4]oxazin-4-yl)-ethyl]-piperidin-4-yl}-N-thiophen-2-ylmethyl-benzamide, |
| 47 | 2-{1-[2-(3-oxo-2,3-dihydro-benzo[1,4]oxazin-4-yl)-ethyl]-piperidin-4-yl}-N-(2-thiophen-2-yl-ethyl)-benzamide, |
| 48 | N-(3-imidazol-1-yl-propyl)-2-{1-[2-(3-oxo-2,3-dihydro-benzo[1,4]oxazin-4-yl)-ethyl]-piperidin-4-yl}-benzamide, |
| 49 | N-(2-acetylamino-ethyl)-2-{1-[2-(3-oxo-2,3-dihydro-benzo[1,4]oxazin-4-yl)-ethyl]-piperidin-4-yl}-benzamide, |
| 50 | 4-[(2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester, |
| 51 | 2-{1-[2-(3-oxo-2,3-dihydro-benzo[1,4]oxazin-4-yl)-ethyl]-piperidin-4-yl}-N-[3-(2-oxo-pyrrolidin-1-yl)-propyl]-benzamide, |
| 52 | 2-{1-[2-(3-oxo-2,3-dihydro-benzo[1,4]oxazin-4-yl)-ethyl]-piperidin-4-yl}-N-(2-piperidin-1-yl-ethyl)-benzamide, |
| 53 | 4-(2-{4-[2-(3,4-dihydro-1H-isoquinoline-2-carbonyl)-phenyl]-piperidin-1-yl}-ethyl)-4H-benzo[1,4]oxazin-3-one, |
| 54 | N-[2-(3-naphthalen-2-yl-ureido)-ethyl]-2-{1-[2-(3-oxo-2,3-dihydro-benzo[1,4]oxazin-4-yl)-ethyl]-piperidin-4-yl}-benzamide, |
| 55 | N-[2-(3-naphthalen-1-yl-ureido)-ethyl]-2-{1-[2-(3-oxo-2,3-dihydro-benzo[1,4]oxazin-4-yl)-ethyl]-piperidin-4-yl}-benzamide, |
| 56 | 5-chloro-2-{1-[2-(3-oxo-2,3-dihydro-benzo[1,4]oxazin-4-yl)-ethyl]-piperidin-4-yl}-benzoic acid methyl ester, |
| 57 | 5-chloro-2-{1-[2-(3-oxo-2,3-dihydro-benzo[1,4]oxazin-4-yl)-ethyl]-piperidin-4-yl}-N-phenethyl-benzamide, |

| Cpd | Name |
|---|---|
| 58 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester, |
| 59 | 5-chloro-N,N-dimethyl-2-{1-[2-(3-oxo-2,3-dihydro-benzo[1,4]oxazin-4-yl)-ethyl]-piperidin-4-yl}-benzamide, |
| 60 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid tert-butyl ester, |
| 61 | 5-chloro-N-(2-naphthalen-2-yl-ethyl)-2-{1-[2-(3-oxo-2,3-dihydro-benzo[1,4]oxazin-4-yl)-ethyl]-piperidin-4-yl}-benzamide, |
| 62 | 5-chloro-N-[2-(1H-indol-3-yl)-ethyl]-2-{1-[2-(3-oxo-2,3-dihydro-benzo[1,4]oxazin-4-yl)-ethyl]-piperidin-4-yl}-benzamide, |
| 63 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzyl ester, |
| 64 | N-(1-benzoyl-piperidin-4-ylmethyl)-5-chloro-2-{1-[2-(3-oxo-2,3-dihydro-benzo[1,4]oxazin-4-yl)-ethyl]-piperidin-4-yl}-benzamide, |
| 65 | 5-chloro-N-[1-(3,3-dimethyl-butyryl)-piperidin-4-ylmethyl]-2-{1-[2-(3-oxo-2,3-dihydro-benzo[1,4]oxazin-4-yl)-ethyl]-piperidin-4-yl}-benzamide, |
| 66 | 4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester, |
| 67 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzylamide, |
| 68 | 4-[2-(5-chloro-2-{1-[2-(3-oxo-2,3-dihydro-benzo[1,4]oxazin-4-yl)-ethyl]-piperidin-4-yl}-benzoylamino)-ethyl]-piperidine-1-carboxylic acid tert-butyl ester, |
| 69 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid benzyl ester, |
| 70 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid tert-butyl ester, |
| 71 | 5-chloro-2-{1-[2-(3-oxo-2,3-dihydro-benzo[1,4]oxazin-4-yl)-ethyl]-piperidin-4-yl}-N-(2-piperidin-1-yl-ethyl)-benzamide, |
| 72 | 5-chloro-2-{1-[2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide, |
| 73 | 5-chloro-2-{1-[2-(3-oxo-2,3-dihydro-benzo[1,4]oxazin-4-yl)-ethyl]-piperidin-4-yl}-N-(2-piperazin-1-yl-ethyl)-benzamide, |
| 74 | [6-(5-chloro-2-{1-[2-(3-oxo-2,3-dihydro-benzo[1,4]oxazin-4-yl)-ethyl]-piperidin-4-yl}-benzoylamino)-hexyl]-carbamic acid tert-butyl ester, |
| 75 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid benzyl ester, |
| 76 | 5-chloro-N-[5-(3,3-dimethyl-butyrylamino)-pentyl]-2-{1-[2-(3-oxo-2,3-dihydro-benzo[1,4]oxazin-4-yl)-ethyl]-piperidin-4-yl}-benzamide, |
| 77 | N-[5-(3-benzyl-ureido)-pentyl]-5-chloro-2-{1-[2-(3-oxo-2,3-dihydro-benzo[1,4]oxazin-4-yl)-ethyl]-piperidin-4-yl}-benzamide, |
| 78 | 5-chloro-2-{1-[2-(3-oxo-2,3-dihydro-benzo[1,4]oxazin-4-yl)-ethyl]-piperidin-4-yl}-N-(5-phenylmethanesulfonylamino-pentyl)-benzamide, |
| 79 | {2-[2-(5-chloro-2-{1-[2-(3-oxo-2,3-dihydro-benzo[1,4]oxazin-4-yl)-ethyl]-piperidin-4-yl}-benzoylamino)-ethoxy]-ethyl}-carbamic acid tert-butyl ester, |
| 80 | 5-chloro-N-[5-(3-isopropyl-ureido)-pentyl]-2-{1-[2-(3-oxo-2,3-dihydro-benzo[1,4]oxazin-4-yl)-ethyl]-piperidin-4-yl}-benzamide, |
| 81 | 5-chloro-2-{1-[2-(3-oxo-2,3-dihydro-benzo[1,4]oxazin-4-yl)-ethyl]-piperidin-4-yl}-N-[5-(3-phenyl-ureido)-pentyl]-benzamide, |
| 82 | 5-chloro-2-{1-[2-(3-oxo-2,3-dihydro-benzo[1,4]oxazin-4-yl)-ethyl]-piperidin-4-yl}-N-[5-(3-phenethyl-ureido)-pentyl]-benzamide, |
| 83 | [5-(5-chloro-2-{1-[2-(2-oxo-3,4-dihydro-2H-quinolin-1-yl)-ethyl]-piperidin-4-yl}-benzoylamino)-pentyl]-carbamic acid tert-butyl ester, |
| 84 | 5-chloro-2-{1-[1-methyl-2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide, |
| 85 | 4-{2-[4-(4-chloro-phenyl)-piperidin-1-yl]-ethyl}-4H-benzo[1,4]oxazin-3-one, |
| 86 | 4-[2-(4-phenyl-piperidin-1-yl)-ethyl]-4H-benzo[1,4]oxazin-3-one, |
| 87 | 4-{2-[4-(4-methoxy-phenyl)-piperidin-1-yl]-ethyl}-4H-benzo[1,4]oxazin-3-one, |
| 88 | 4-{2-[4-(3-fluoro-phenyl)-piperidin-1-yl]-ethyl}-4H-benzo[1,4]oxazin-3-one, |
| 89 | 4-{2-[4-(2-fluoro-phenyl)-piperidin-1-yl]-ethyl}-4H-benzo[1,4]oxazin-3-one, |
| 90 | 4-[2-(4-p-tolyl-piperidin-1-yl)-ethyl]-4H-benzo[1,4]oxazin-3-one, |
| 91 | 4-[2-(4-o-tolyl-piperidin-1-yl)-ethyl]-4H-benzo[1,4]oxazin-3-one, |
| 92 | 4-{2-[4-(3-chloro-phenyl)-piperidin-1-yl]-ethyl}-4H-benzo[1,4]oxazin-3-one, |
| 93 | 2-{1-[2-(3-oxo-2,3-dihydro-benzol[1,4]oxain-4-yl-ethyl]-piperidine-4-yl-benzoic acid methyl ester, |
| 94 | 4-[2-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-ethyl]-piperazine-1-carboxylic acid tert-butyl ester, |
| 95 | [5-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-pentyl]-carbamic acid tert-butyl ester, |
| 96 | 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester, |

| Cpd | Name |
|---|---|
| 97 | [5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester, |
| 98 | [5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester, |
| 99 | 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester, |
| 100 | [5-(5-chloro-2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester, |
| 101 | 4-[2-(3-phenyl-8-aza-bicyclo[3.2.1]oct-8-yl)-ethyl]-4H-benzo[1,4]oxazin-3-one, |
| 102 | [5-(5-chloro-2-{2,6-dimethyl-1-[2-(3-oxo-2,3-dihydro-benzo[1,4]oxazin-4-yl)-ethyl]-1,2,3,6-tetrahydro-pyridin-4-yl}-benzoylamino)pentyl]-carbamic acid tert-butyl ester, |
| 103 | 1-[2-(3-oxo-2,3-dihydro-benzo[1,4]oxazin-4-yl)-ethyl]-4-phenyl-piperidine-4-carboxylic acid dimethyl amide, |
| 104 | 1-[2-(3-oxo-2,3-dihydro-benzo[1,4]oxazin-4-yl)-ethyl]-4-phenyl-piperidine-4-carboxylic acid benzylamide, |
| 105 | 1-[2-(3-oxo-2,3-dihydro-benzo[1,4]oxazin-4-yl)-ethyl]-4-phenyl-piperidine-4-carboxylic acid phenethyl-amide, |
| 106 | 1-[2-(3-oxo-2,3-dihydro-benzo[1,4]oxazin-4-yl)-ethyl]-4-phenyl-piperidine-4-carboxylic acid methyl-phenethyl-amide, |
| 107 | 1-[2-(3-oxo-2,3-dihydro-benzo[1,4]oxazin-4-yl)-ethyl]-4-phenyl-piperidine-4-carboxylic acid (3-phenyl-propyl)-amide, |
| 108 | 1-[2-(3-oxo-2,3-dihydro-benzo[1,4]oxazin-4-yl)-ethyl]-4-phenyl-piperidine-4-carboxylic acid (4-phenyl-butyl)-amide, |
| 109 | 4-(4-chloro-phenyl)-1-[2-(3-oxo-2,3-dihydro-benzo[1,4]oxazin-4-yl)-ethyl]-piperidine-4-carboxylic acid phenethyl-amide, |
| 110 | 1-[2-(6-chloro-3-oxo-2,3-dihydro-benzo[1,4]oxazin-4-yl)-ethyl]-4-(4-chloro-phenyl)-piperidine-4-carboxylic acid dimethylamide, |
| 111 | 4-(4-chloro-phenyl)-1-[2-(6-methyl-3-oxo-2,3-dihydro-benzo[1,4]oxazin-4-yl)-ethyl]-piperidine-4-carboxylic acid dimethylamide, |
| 112 | 4-(4-chloro-phenyl)-1-[2-(6-fluoro-3-oxo-2,3-dihydro-benzo[1,4]oxazin-4-yl)-ethyl]-piperidine-4-carboxylic acid dimethylamide, |
| 113 | 4-(4-chloro-phenyl)-1-[2-(3-oxo-2,3-dihydro-benzo[1,4]oxazin-4-yl)-ethyl]-piperidine-4-carboxylic acid dimethylamide, |
| 114 | 4-(4-chloro-phenyl)-1-[2-(3-oxo-2,3-dihydro-benzo[1,4]thiazin-4-yl)-ethyl]-piperidine-4-carboxylic acid dimethylamide, |
| 115 | 4-(4-chloro-phenyl)-1-[2-(2-oxo-3,4-dihydro-2H-quinolin-1-yl)-ethyl]-piperidine-4-carboxylic acid dimethylamide, and |
| 116 | 4-[2-(4-phenyl-piperidin-1-yl)-propyl]-4H-benzo[1,4]oxazin-3-one. |

A compound of Formula (I) or a form thereof further includes a compound selected from the group consisting of:

| Cpd | Name |
|---|---|
| 3 | 2-{1-[2-(3-oxo-2,3-dihydro-benzo[1,4]oxazin-4-yl)-ethyl-piperidin-4-yl}-N-(3-phenyl-propyl)-benzamide, |
| 20 | N-(2-naphthalen-2-yl-ethyl)-2-{1-[2-(3-oxo-2,3-dihydro-benzo[1,4]oxazin-4-yl)-ethyl]-piperidin-4-yl}-benzamide, |
| 26 | N-[2-(1H-indol-3-yl)-ethyl]-2-{1-[2-(3-oxo-2,3-dihydro-benzo[1,4]oxazin-4-yl)-ethyl]-piperidin-4-yl}-benzamide, |
| 34 | N-[2-(4-bromo-phenyl)-ethyl]-2-{1-[2-(3-oxo-2,3-dihydro-benzo[1,4]oxazin-4-yl)-ethyl]-piperidin-4-yl}-benzamide, |
| 35 | [4-(2-{1-[2-(3-oxo-2,3-dihydro-benzo[1,4]oxazin-4-yl)-ethyl]-piperidin-4-yl}-benzoylamino)-butyl]-carbamic acid tert-butyl ester, |
| 50 | 4-[(2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester, |
| 55 | N-[2-(3-naphthalen-1-yl-ureido)-ethyl]-2-{1-[2-(3-oxo-2,3-dihydro-benzo[1,4]oxazin-4-yl)-ethyl]-piperidin-4-yl}-benzamide, |
| 57 | 5-chloro-2-{1-[2-(3-oxo-2,3-dihydro-benzo[1,4]oxazin-4-yl)-ethyl]-piperidin-4-yl}-N-phenethyl-benzamide, |
| 58 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester, |
| 60 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid tert-butyl ester, |
| 61 | 5-chloro-N-(2-naphthalen-2-yl-ethyl)-2-{1-[2-(3-oxo-2,3-dihydro-benzo[1,4]oxazin-4-yl)-ethyl]-piperidin-4-yl}-benzamide, |
| 62 | 5-chloro-N-[2-(1H-indol-3-yl)-ethyl]-2-{1-[2-(3-oxo-2,3-dihydro-benzo[1,4]oxazin-4-yl)-ethyl]-piperidin-4-yl}-benzamide, |
| 63 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzyl ester, |

| Cpd | Name |
|---|---|
| 64 | N-(1-benzoyl-piperidin-4-ylmethyl)-5-chloro-2-{1-[2-(3-oxo-2,3-dihydro-benzo[1,4]oxazin-4-yl)-ethyl]-piperidin-4-yl}-benzamide, |
| 65 | 5-chloro-N-[1-(3,3-dimethyl-butyryl)-piperidin-4-ylmethyl]-2-{1-[2-(3-oxo-2,3-dihydro-benzo[1,4]oxazin-4-yl)-ethyl]-piperidin-4-yl}-benzamide, |
| 66 | 4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester, |
| 67 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzylamide, |
| 68 | 4-[2-(5-chloro-2-{1-[2-(3-oxo-2,3-dihydro-benzo[1,4]oxazin-4-yl)-ethyl]-piperidin-4-yl}-benzoylamino)-ethyl]-piperidine-1-carboxylic acid tert-butyl ester, |
| 69 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid benzyl ester, |
| 70 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid tert-butyl ester, |
| 71 | 5-chloro-2-{1-[2-(3-oxo-2,3-dihydro-benzo[1,4]oxazin-4-yl)-ethyl]-piperidin-4-yl}-N-(2-piperidin-1-yl-ethyl)-benzamide, |
| 72 | 5-chloro-2-{1-[2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide, |
| 74 | [6-(5-chloro-2-{1-[2-(3-oxo-2,3-dihydro-benzo[1,4]oxazin-4-yl)-ethyl]-piperidin-4-yl}-benzoylamino)-hexyl]-carbamic acid tert-butyl ester, |
| 75 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid benzyl ester, |
| 76 | 5-chloro-N-[5-(3,3-dimethyl-butyrylamino)-pentyl]-2-{1-[2-(3-oxo-2,3-dihydro-benzo[1,4]oxazin-4-yl)-ethyl]-piperidin-4-yl}-benzamide, |
| 77 | N-[5-(3-benzyl-ureido)-pentyl]-5-chloro-2-{1-[2-(3-oxo-2,3-dihydro-benzo[1,4]oxazin-4-yl)-ethyl]-piperidin-4-yl}-benzamide, |
| 78 | 5-chloro-2-{1-[2-(3-oxo-2,3-dihydro-benzo[1,4]oxazin-4-yl)-ethyl]-piperidin-4-yl}-N-(5-phenylmethanesulfonylamino-pentyl)-benzamide, |
| 79 | {2-[2-(5-chloro-2-{1-[2-(3-oxo-2,3-dihydro-benzo[1,4]oxazin-4-yl)-ethyl]-piperidin-4-yl}-benzoylamino)-ethoxy]-ethyl}-carbamic acid tert-butyl ester, |
| 80 | 5-chloro-N-[5-(3-isopropyl-ureido)-pentyl]-2-{1-[2-(3-oxo-2,3-dihydro-benzo[1,4]oxazin-4-yl)-ethyl]-piperidin-4-yl}-benzamide, |
| 81 | 5-chloro-2-{1-[2-(3-oxo-2,3-dihydro-benzo[1,4]oxazin-4-yl)-ethyl]-piperidin-4-yl}-N-[5-(3-phenyl-ureido)-pentyl]-benzamide, |
| 82 | 5-chloro-2-{1-[2-(3-oxo-2,3-dihydro-benzo[1,4]oxazin-4-yl)-ethyl]-piperidin-4-yl}-N-[5-(3-phenethyl-ureido)-pentyl]-benzamide, |
| 83 | [5-(5-chloro-2-{1-[2-(2-oxo-3,4-dihydro-2H-quinolin-1-yl)-ethyl]-piperidin-4-yl}-benzoylamino)-pentyl]-carbamic acid tert-butyl ester, |
| 84 | 5-chloro-2-{1-[1-methyl-2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide, |
| 94 | 4-[2-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-ethyl]-piperazine-1-carboxylic acid tert-butyl ester, and |
| 95 | [5-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-pentyl]-carbamic acid tert-butyl ester. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a MeI-Temp II apparatus (Laboratory Devices Inc.) and were uncorrected. Electrospray mass spectra (MS-ES) were recorded on a Hewlett Packard 59987A spectrometer. High resolution mass spectra (HRMS) were obtained on a Micromass Autospec. E spectrometer by fast atom bombardment (FAB) technique.

The terms used in describing the invention are commonly used and known to those skilled in the art. Abbreviations used in the instant specification, particularly the Schemes and Examples, are as follows:

| | |
|---|---|
| BAP | borane-pyridine complex |
| Boc | tert-butoxycarbonyl |
| BSA | bovine serum albumin |
| DCM | dichloromethane |
| DMF | N,N-dimethylformamide |
| DMSO | dimethylsulfoxide |
| DIPEA | diisopropylethylamine |
| Et$_2$O | diethyl ether |
| EtOAc | ethyl acetate |
| EtOH | ethanol |

| | |
|---|---|
| hr(s) | hour(s) |
| HBTU | O-benzotriazol-1-yl-N,N,N',N'-tetramethyluronium hexafluorophosphate |
| HOBt | hydroxybenzotriazole hydrate |
| HPLC | High Performance Liquid Chromatography |
| HEPES | 4-(2-hydroxyethyl)-1-piperazine-ethanesulfonic acid |
| MeOH | methanol |
| min | minutes |
| MTBE | methyl t-butyl ether |
| PdCl$_2$dppf-CH$_2$Cl$_2$ | [1,1'-bis(diphenylphosphino)ferrocene]-dichloropalladium(II) dichloromethane complex |
| psi | pounds per square inch |
| rt | room temperature |
| SDS | sodium dodecasulfate |
| TEA or Et$_3$N | triethylamine |
| THF | tetrahydrofuran |
| TFA | trifluoroacetic acid |

Scheme A describes the synthesis of compounds of the present invention wherein A is a piperidinyl ring of Formula (I).

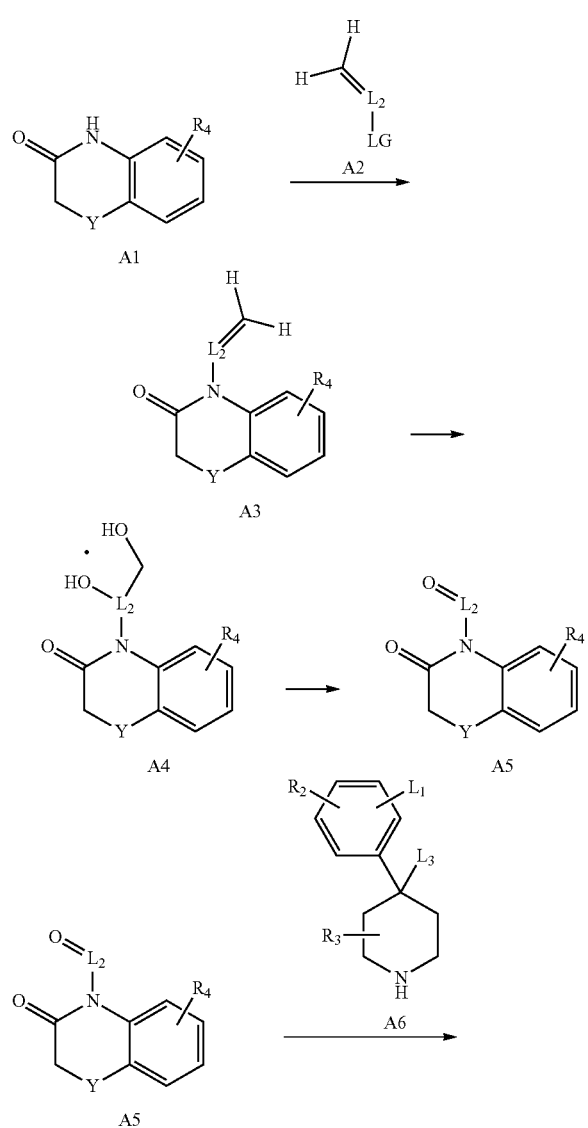

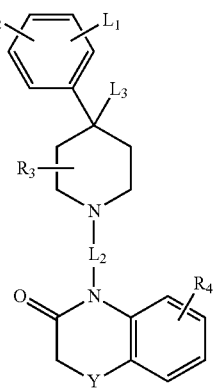

Formula (I)-1

A commercially available heterocycle of Compound A1 may be reacted with a strong base such as sodium hydride and a commercially available or readily accessible electrophile Compound A2 in which an appropriate leaving group (LG) is displaced. Examples of appropriate leaving groups include fluoride, bromide, iodide, triflate, mesylate, and the like.

The leaving group of Compound A2 may be displaced to give a Compound A3. The terminal olefin in Compound A3 can be converted to a carbonyl of Compound A5 directly or through the intermediate Compound A4.

For example oxidation of Compound A3 with potassium osmate (VI) can deliver diol Compound A4, which may be decomposed to Compound A5 with sodium metaperiodate.

Alternatively ozone will convert Compound A3 to Compound A5 directly after a reductive workup with a reductant such as dimethylsulfide or triphenylphosphine. The carbonyl of Compound A5 may be coupled to Compound A6 under reductive amination conditions to afford compounds of Formula (I)-1, representative of a compound of Formula (I).

Reductive amination conditions would include a reducing agent such as borane-pyridine, sodium cyanoborohydride, sodium triacetoxyborohydride, and the like. Use of Brönsted or Lewis acids and a dehydrating agent may also be beneficial.

Scheme B

Scheme B describes the synthesis of compounds of the present invention wherein Ring A is piperidinyl and L$_3$ is —C(O)N(R$_5$)—R$_7$.

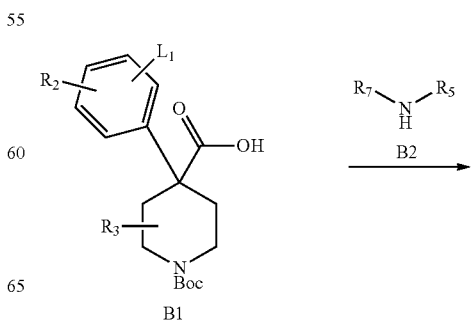

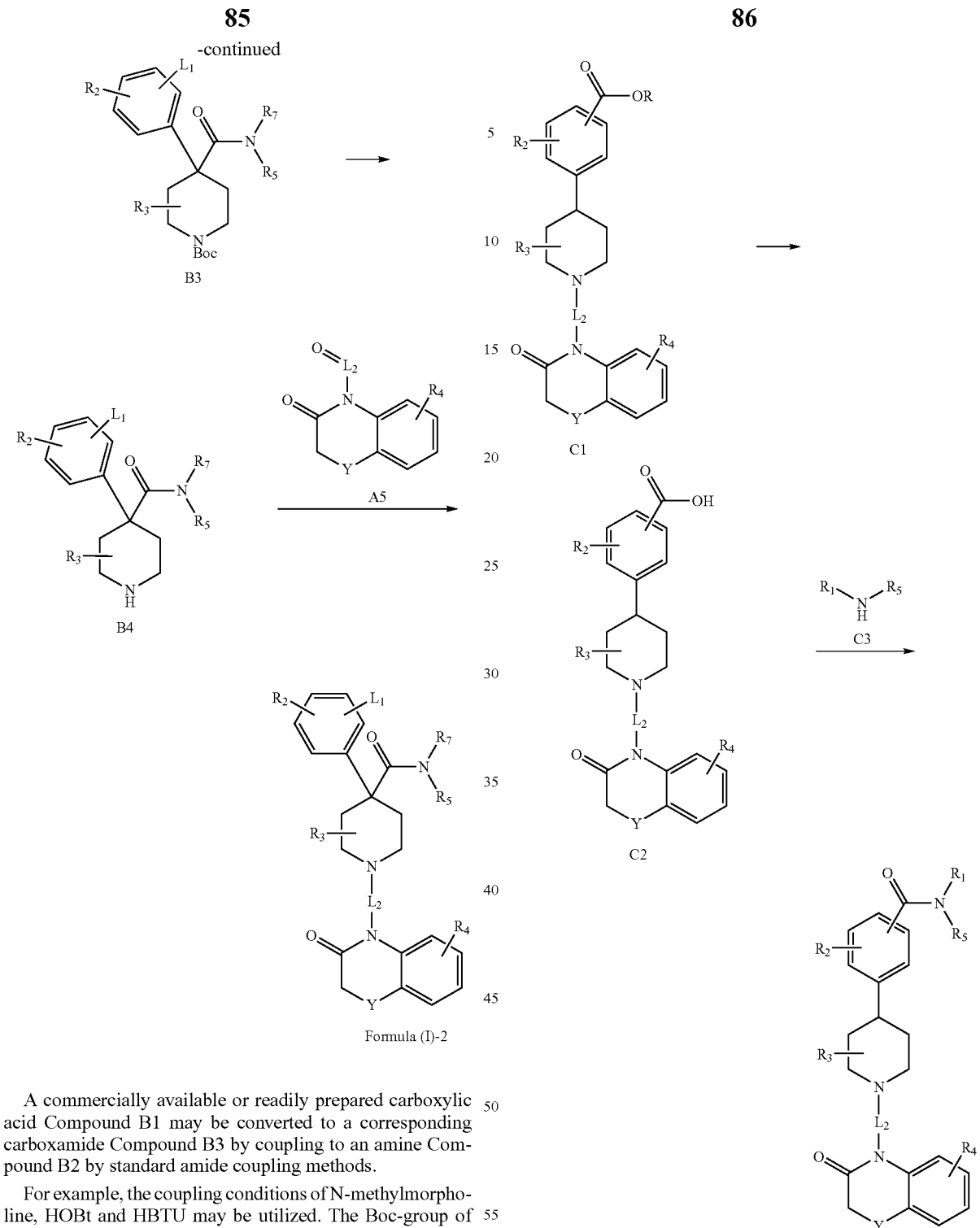

Formula (I)-2

A commercially available or readily prepared carboxylic acid Compound B1 may be converted to a corresponding carboxamide Compound B3 by coupling to an amine Compound B2 by standard amide coupling methods.

For example, the coupling conditions of N-methylmorpholine, HOBt and HBTU may be utilized. The Boc-group of Compound B3 can be removed with an acid such as hydrogen chloride or trifluoroacetic acid to afford the free amine of Compound B4.

Reductive coupling of Compound B4 and Compound A5 by the methods described in general Scheme A for coupling of A6 and A5 may afford compounds of Formula (I)-2, representative of a compound of Formula (I).

Scheme C

Scheme C describes the synthesis of certain compounds of the present invention in which $L_1$ is a carboxamide substituent.

An ester Compound C1 is prepared by the methods described in general Scheme A. Compound C1 can be hydrolyzed to the carboxylic acid Compound C2 with a base such as lithium hydroxide. Coupling of Compound C2 to the amine Compound C3 by methods described in general Scheme B for the coupling of Compound B1 and Compound B2 provides compounds of Formula (I)-3, representative of a compound of Formula (I).

A subset of amine Compound C3 are the primary amines of Compound C5. Compound C5 can be prepared by reduction of the corresponding nitrile Compound C4 by a reagent such as a borane-tetrahydrofuran complex.

Scheme D

Scheme D describes the synthesis of compounds of the present invention wherein the phenylpiperidine group is not commercially available.

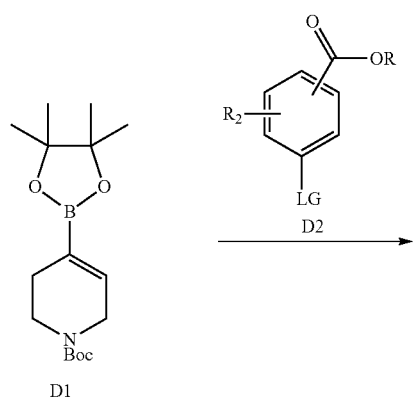

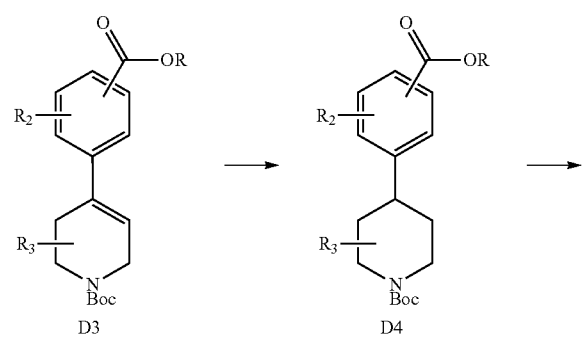

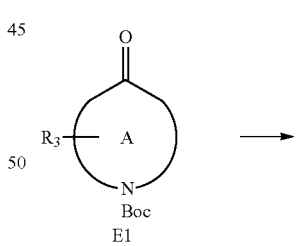

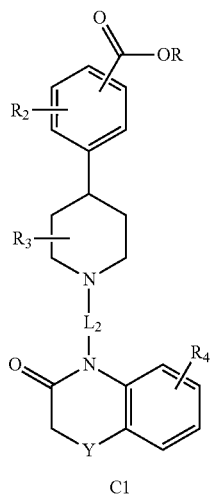

Commercially available boronate Compound D1 can be coupled with a Compound D2, in which LG may be a leaving group as previously defined or, for the reaction illustrated in this Scheme, when LG is bromide or triflate. The Suzuki Miyaura coupling (P. R. Eastwood, Tetrahedron Lett., 2000, 41, 3705) is facilitated by a palladium catalyst such as $PdCl_2dppf\text{-}CH_2Cl_2$.

Reduction of the double bond in Compound D3 may be accomplished with hydrogen and a catalyst such as platinum (IV) oxide. Deprotection of the Boc-group on Compound D4 can be done as described in general Scheme B for Compound B3. Reductive coupling of Compound D5 and Compound A5 is achieved by the methods described in general Scheme A for Compound A6 and Compound A5. Conversion of Compound C1 to the structures of Formula (I)-3 is accomplished by the sequence described in general Scheme C.

Scheme E

Scheme E describes the synthesis of compounds in which the vinyl boronate within Ring A needs to be prepared.

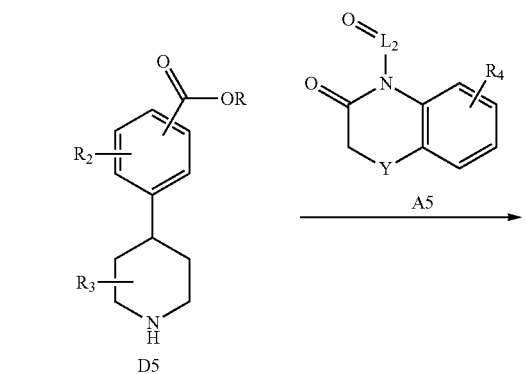

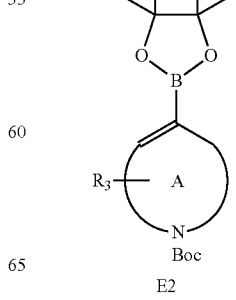

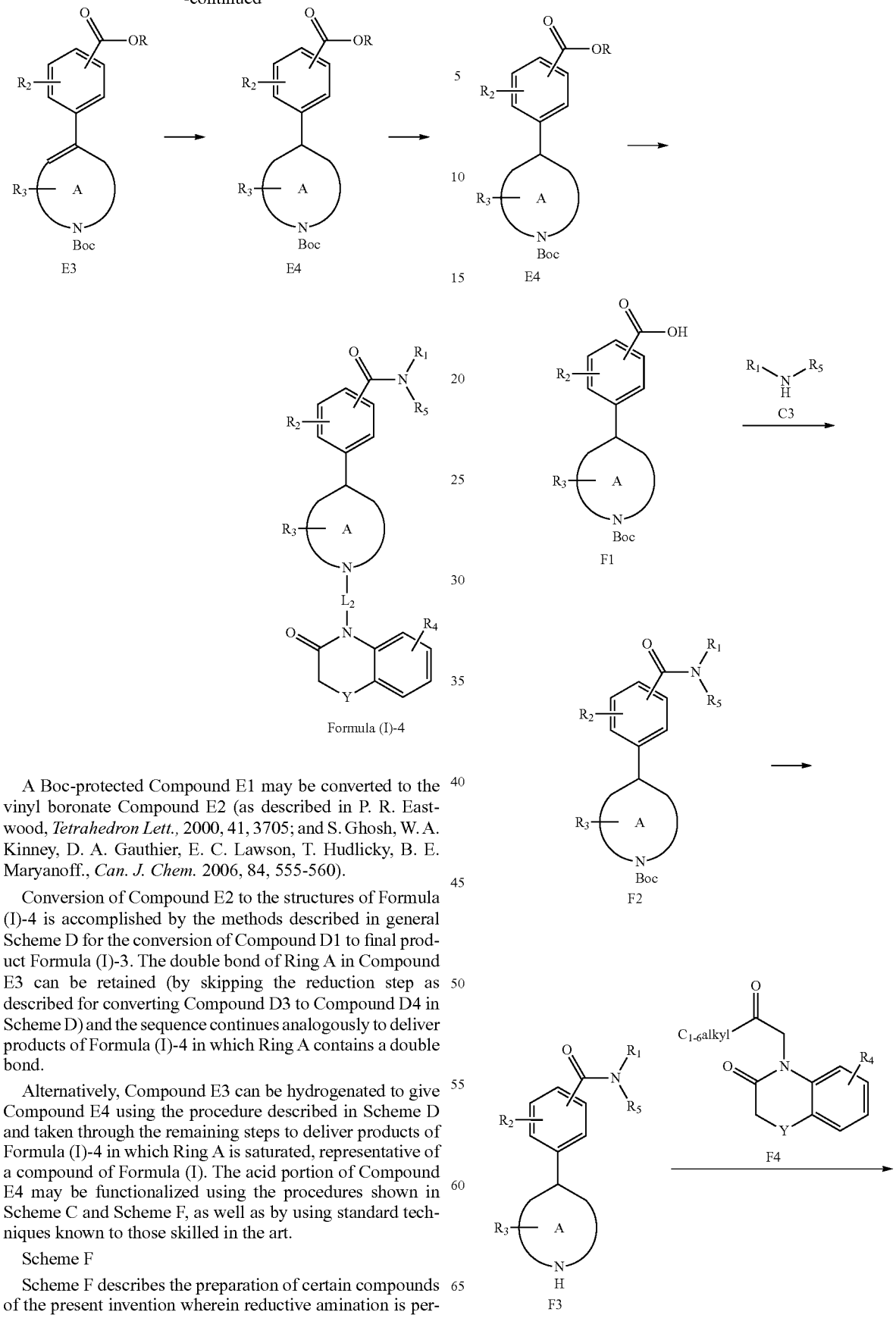

Formula (I)-4

A Boc-protected Compound E1 may be converted to the vinyl boronate Compound E2 (as described in P. R. Eastwood, *Tetrahedron Lett.*, 2000, 41, 3705; and S. Ghosh, W. A. Kinney, D. A. Gauthier, E. C. Lawson, T. Hudlicky, B. E. Maryanoff., *Can. J. Chem.* 2006, 84, 555-560).

Conversion of Compound E2 to the structures of Formula (I)-4 is accomplished by the methods described in general Scheme D for the conversion of Compound D1 to final product Formula (I)-3. The double bond of Ring A in Compound E3 can be retained (by skipping the reduction step as described for converting Compound D3 to Compound D4 in Scheme D) and the sequence continues analogously to deliver products of Formula (I)-4 in which Ring A contains a double bond.

Alternatively, Compound E3 can be hydrogenated to give Compound E4 using the procedure described in Scheme D and taken through the remaining steps to deliver products of Formula (I)-4 in which Ring A is saturated, representative of a compound of Formula (I). The acid portion of Compound E4 may be functionalized using the procedures shown in Scheme C and Scheme F, as well as by using standard techniques known to those skilled in the art.

Scheme F

Scheme F describes the preparation of certain compounds of the present invention wherein reductive amination is performed on a ketone.

-continued

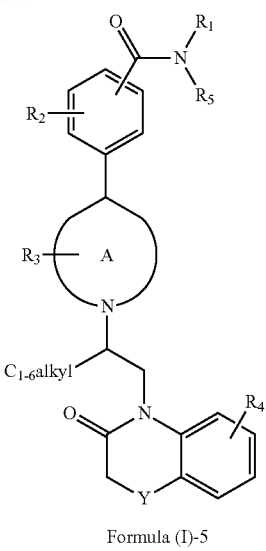

Formula (I)-5

The Boc-protected carboxylic acid ester Compound E4 can be converted to the corresponding carboxyl acid Compound F1 by the action of a base such as sodium hydroxide. Coupling of Compound F1 to Compound C3 is accomplished using the procedure for coupling Compound B1 and Compound B2 in Scheme B. Compound F2 is then deprotected as described in Scheme B to give a Compound F3.

The reductive amination of ketone Compound F4 with Compound F3 is achieved by using a neat Lewis acid such as titanium (IV) isopropoxide with heat. The reaction mixture is then treated a hydride source such as sodium borohydride in an alcoholic solvent to afford a compound of Formula (I)-5, representative of a compound of Formula (I).

Example 1

4-[2-(4-phenyl-piperidin-1-yl)-ethyl]-4H-benzo[1,4]oxazin-3-one (Compound 86)
2-{1-[2-(3-oxo-2,3-dihydro-benzo[1,4]oxain-4-yl-ethyl-piperidine-4-yl-benzoic acid methyl ester (Compound 93)

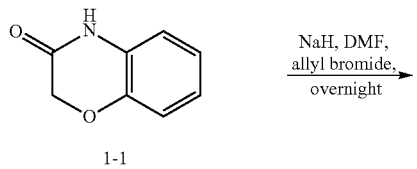

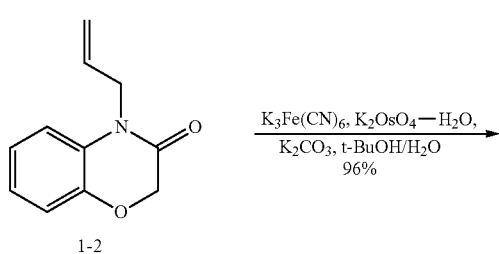

-continued

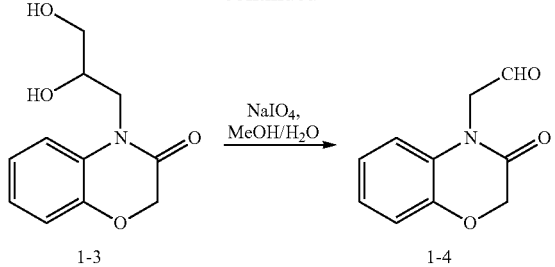

Step 1. Synthesis of 4-allyl-4H-benzo[1,4]oxazin-3-one (Compound 1-2)

Compound 1-1 (5.06 g, 34 mmol) was dissolved in DMF (200 mL) and chilled to 4° C. in an ice bath. To this solution was added 95% sodium hydride (946 mg, 39 mmol) in three equal parts keeping the temperature at 4° C. Stirring was continued in the ice bath for 30 min before adding the allyl bromide (3.23 mL, 37 mmol) dropwise through an addition funnel. The reaction mixture was stirred (20 hrs), allowing the mixture to come to room temperature. The reaction mixture was then poured slowly into cold 1N hydrochloric acid solution (100 mL) and diluted with EtOAc (150 mL). The organic layer was washed with 1N sodium hydroxide solution (2×50 mL), water (2×50 mL) and brine (1×100 mL), then dried over $Na_2SO_4$; and concentrated to give a glass-like oil. The compound was purified on silica gel (elution with 25% EtOAc in hexane) to give Compound 1-2 (5.2 g, 28 mmol, 82%). $^1$H NMR (300 MHz, $CDCl_3$) δ 6.95 (s, 4H), 5.89-5.78 (m, 1H), 5.21-5.17 (m, 2H), 4.57 (s, 2H), 4.51-4.45 (m, 2H); MS ($ES^+$) m/z 190.1 (M+1).

Step 2. Synthesis of 4-(2,3-dihydroxy-propyl)-4H-benzo[1,4]oxazin-3-one (Compound 1-3)

A solution of potassium carbonate (4.40 g, 32 mmol), $K_3Fe(CN)_6$ (10.5 g, 32 mmol), and $K_2OsO_4 \cdot H_2O$ (195 mg, 0.53 mmol) in t-BuOH/$H_2O$ (12 mL of 1/1) was prepared in a 200 mL round bottom flask. The mixture was chilled in an ice bath, then a solution of Compound 1-2 (2.0 g, 11 mmol) in t-BuOH/$H_2O$ (12 mL of 1/1) was added at 4° C. and the reaction mixture was allowed to stir for 24 hrs while warming to rt. The reaction mixture was poured into EtOAc (100 mL) and washed with 2 N hydrochloric acid solution (5×75 mL). The organic layer was dried over $Na_2SO_4$, concentrated, and purified on silica gel (elution with 90:9:1 dichloromethane/methanol/ammonium hydroxide) to give Compound 1-3 (2.2 g, 96%) as a glass-like oil. $H^1$ NMR (300 MHz, $CDCl_3$) δ 7.20-7.16 (m, 1H), 7.07-6.98 (m, 3H), 4.60 (s, 2H), 4.20-3.92 (m, 3H), 3.72-3.56 (m, 2H); MS ($ES^+$) m/z 224.1 (M+1).

Step 3. Synthesis of (3-oxo-2,3dihydro-benzo[1,4]oxazin-4-yl)-acetaldehyde (Compound 1-4)

Compound 1-3 (1.69 g, 7.58 mmol) was dissolved in MeOH (126 mL) and $H_2O$ (25 mL) in a 300 mL round bottom flask at rt, and treated with $NaIO_4$ (4.86 g, 23.0 mmol). After 2 hrs the solid was filtered, washing with methanol. The filtrate was concentrated to a white solid, taken up in dichloromethane (50 mL), washed with water (3×) and brine, then dried over sodium sulfate, and concentrated to give Compound 1-4 as a white solid (1.23 g, 83%, mp=97.1-98.0° C.). $^1$H NMR (500 MHz, $CDCl_3$) δ 9.68 (s, 1H), 7.04-7.00 (m, 3H), 6.68-6.65 (m, 1H), 4.73 (s, 2H), 4.70 (s, 2H); $^{13}$C NMR (125 MHz, CDCl$_3$) 195, 165.2, 145.3, 128.7, 124.7, 123.2, 117.6, 114.7, 67.6, 51.2; Anal Calcd. for C$_{10}$H$_9$NO$_3$: C, 62.82; H, 4.74; N, 7.33. Found: C, 62.85; H, 4.46; N, 7.22.

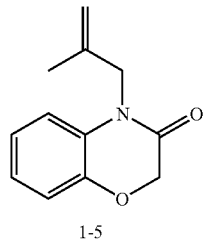

1-5

1) O$_3$, CH$_2$Cl$_2$, -70° C.,
2) PPh$_3$ (43%)

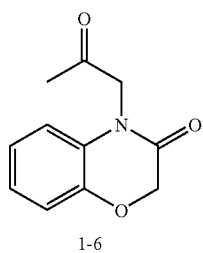

1-6

Step 4. Synthesis of 4-(2-oxo-propyl)-4H-benzo[1,4]oxazin-3-one (Compound 1-6)

Compound 1-5 was prepared by the same method as Compound 1-2 with the exception that 3-chloro-2-methylpropene was utilized instead of allyl bromide. Ozone was bubbled through a cold (-70° C.) solution of Compound 1-5 (30.0 g, 147 mmol) and Sudan III (trace) in dichloromethane (450 mL) for 1.5 hrs. Triphenylphosphine (46.3 g, 177 mmol) was added at a rate that the internal temperature was maintained at -70° C. The resulting solution was stirred at -70° C. for 30 min, warmed to rt, and stirred for 1 hr. The volatile materials were removed by evaporation to give a crude residue, which was dissolved in dichloromethane and applied to a flash column for purification (1.36 kg of 230-400 mesh silica gel, gradient elution with 0-30% EtOAc in hexane). Evaporation of the appropriate fractions gave Compound 1-6 as a white solid (13.0 g, 43%, mp 74-76° C.). $^1$H NMR (300 MHz, CDCl$_3$) δ 7.04-6.95 (m, 3H), 6.64-6.59 (m, 1H), 4.69 (s, 4H), 2.26 (s, 3H); $^{13}$C NMR (75 Hz, CDCl$_3$) δ 201.8, 164.9, 145.2, 128.8, 124.4, 123.1, 117.4, 114.6, 67.6, 51.2, 27.1; MS (ES$^+$) m/z 206.1 (M+1); Anal Calcd. for C$_{11}$H$_{11}$NO$_3$: C, 64.38; H, 5.40; N, 6.83. Found: C, 64.23; H, 5.12; N, 6.75.

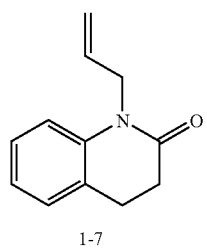

1-7

1) O$_3$, MeOH, -78° C.,
2) DMS (60%)

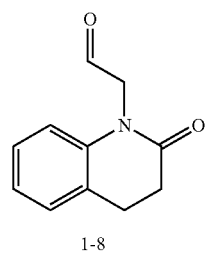

1-8

Step 5. Synthesis of (2-oxo-3,4-dihydro-2H-quinolin-1-yl)-acetaldehyde (Compound 1-8)

Compound 1-7 was prepared by the same method as Compound 1-2 with the exception that dihydroquinolinone was utilized instead of Compound 1-1. Ozone (8 psi) was bubbled slowly into a cold (-78° C.) solution of Compound 1-7 (10 g, 54 mmol) in methanol (535 mL) for 90 min, while the solution turned from yellow to blue-green. Oxygen was bubbled through the solution until the solution turned yellow, and then dimethylsulfide (5.3 mL, 73 mmol) was added dropwise at such a rate that the internal temperature was maintained at -78° C. The resulting solution was kept at 3° C. for 18 hrs, then warmed to rt. The solvent was evaporated to give a crude product, which was purified by column chromatography on silica gel (gradient elution with 10-50% EtOAc in hexane). Evaporation of the appropriate fractions gave 9 g of an oil that was treated with tetrahydrofuran (150 mL), water (50 mL), and 4 M HCl (20 mL). The resulting mixture was stirred for 1 hr at rt and treated with MTBE. The organic layer was washed with water, dried over sodium sulfate, filtered, and evaporated to give a clear oil which was treated a second time with THF, water and 4 M HCl, and stirred for 2 hrs. Extraction again with MTBE, washing, drying, and evaporation afforded Compound 1-8 as an oil (6.1 g, 60%). $^1$H NMR (300 MHz, CDCl$_3$) δ 9.65 (s, 1H), 7.24-7.16 (m, 2H), 7.06-7.00 (m, 1H), 6.67 (d, J=9.3 Hz, 1H), 4.71 (s, 2H), 3.01-2.95 (m, 2H), 2.77-2.71 (m, 2H); $^{13}$C NMR (75 Hz, CDCl$_3$) δ 197.40, 171.05, 139.65, 128.44, 127.90, 126.51, 123.71, 114.66, 52.78, 31.55, 25.58; MS (ES$^+$) m/z 190.11 (M+1).

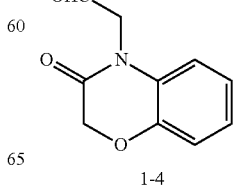

1-4

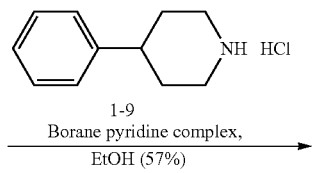

1-9
Borane pyridine complex,
EtOH (57%)

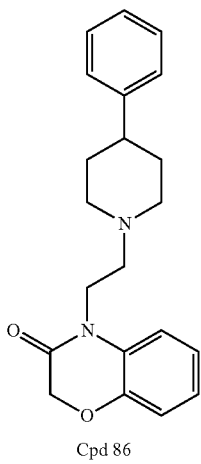

Cpd 86

Step 6. Synthesis of 4-[2-(4-phenyl-piperidine-1-yl)-ethyl]-4H-benzo[1,4]oxazin-3-one (Compound 86)

Following the procedure of *Synthetic Comm.* 23 (6), 789-795, 1993, to a solution of 4-phenylpiperidine hydrochloride Compound 1-9 (290 mg, 1.5 mmol) and Compound 1-4 (300 mg, 1.5 mmol) in 10 mL of absolute ethanol was added BAP (154 μL, 1.5 mmol). After stirring for 2 hrs, an additional equivalent of aldehyde Compound 1-4 and BAP was added. The reaction mixture was stirred overnight and concentrated to give an oily residue. The residue was taken up in DCM, washed with saturated sodium bicarbonate solution NaHCO$_3$ and brine, dried over Na$_2$SO$_4$, and concentrated. The residue was purified on silica gel (elution with 30% EtOAc in hexane) to yield Compound 86 as a glass-like oil (287 mg, 57%) of a glass-like oil. $^1$H NMR (300 MHz, CDCl$_3$) δ 7.25-7.11 (m, 5H), 7.04-6.91 (m, 4H), 4.53 (s, 2H), 4.04 (m, 2H), 3.04 (m, 2H), 2.58 (m, 2H), 2.45-2.40 (m, 1H), 2.15, (t of d, J=11 and 3 Hz, 2H), 1.83-1.64 (m, 4H); MS (ES$^+$) m/z 337.2 (M+1); Anal Calcd. for C$_{21}$H$_{24}$N$_2$O$_2$.0.51H$_2$O: C, 73.02; H, 7.29; N, 8.11. Found: C, 72.98; H, 7.11; N, 8.00.

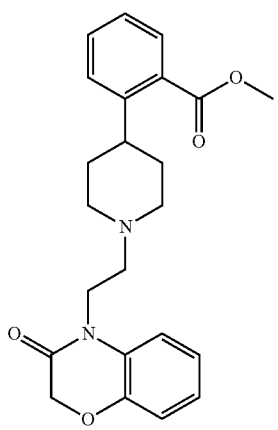

Cpd 93

Step 7. Synthesis of 2-{1-[2-(3-oxo-2,3-dihydro-benzol[1,4]oxain-4-yl-ethyl]-piperidine-4-yl-benzoic acid methyl ester (Compound 93)

Compound 93 was synthesized in the same manner as Compound 86 with the exception that 2-(piperidin-4-yl)ben- zoic acid methyl ester was used instead of Compound 1-9 as starting material. Compound 93 was purified on silica gel (elution with 50% EtOAc in hexane) to afford a glass-like oil (25%). $^1$H NMR (300 MHz, CDCl$_3$) δ 7.77 (d, J=7 Hz, 1H), 7.46-7.40 (m, 2H), 7.08 (m, 1H), 7.05-7.00 (m, 4H), 4.60 (s, 2H), 4.12 (m, 2H), 3.89 (s, 3H), 3.42-3.31 (m, 1H), 3.12 (m, 2H), 2.69 (m, 2H), 2.27 (t of d, J=11 and 3 Hz, 2H), 1.85-1.73 (m, 4H); MS (ES$^+$) m/z 395.2 (M+1).

Using the procedure of Example 1, other compounds representative of the present invention may be prepared:

| Cpd | Name | MS |
| --- | --- | --- |
| 85 | 4-{2-[4-(4-chloro-phenyl)-piperidin-1-yl]-ethyl}-4H-benzo[1,4]oxazin-3-one | 371.2 |
| 87 | 4-{2-[4-(4-methoxy-phenyl)-piperidin-1-yl]-ethyl}-4H-benzo[1,4]oxazin-3-one | 367.2 |
| 88 | 4-{2-[4-(3-fluoro-phenyl)-piperidin-1-yl]-ethyl}-4H-benzo[1,4]oxazin-3-one | 355.2 |
| 89 | 4-{2-[4-(2-fluoro-phenyl)-piperidin-1-yl]-ethyl}-4H-benzo[1,4]oxazin-3-one | 355.2 |
| 90 | 4-[2-(4-p-tolyl-piperidin-1-yl)-ethyl]-4H-benzo[1,4]oxazin-3-one | 351.3 |
| 91 | 4-[2-(4-o-tolyl-piperidin-1-yl)-ethyl]-4H-benzo[1,4]oxazin-3-one | 351.1 |
| 92 | 4-{2-[4-(3-chloro-phenyl)-piperidin-1-yl]-ethyl}-4H-benzo[1,4]oxazin-3-one | 371.2 |

Example 2

4-(4-chloro-phenyl)-1-[2-(2-oxo-3,4-dihydro-2H-quinolin-1-yl)-ethyl]-piperidine-4-carboxylic acid dimethylamide (Compound 115)

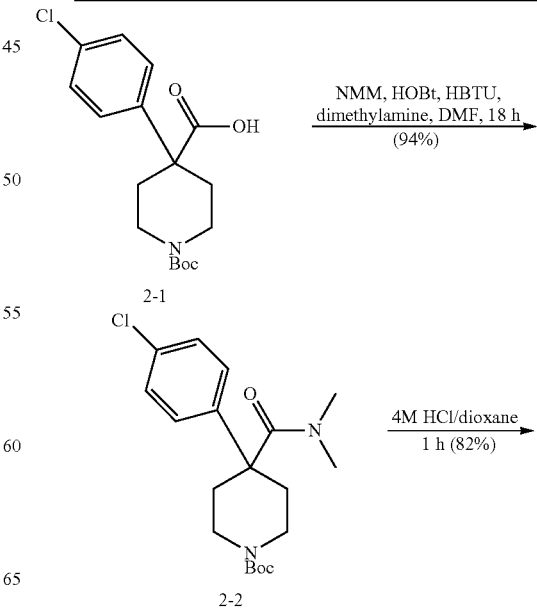

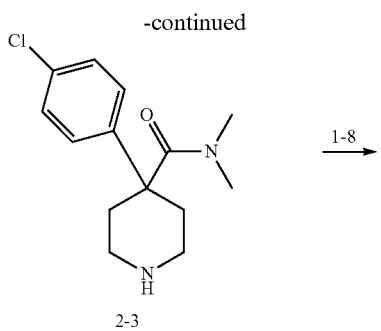

Step 2. Synthesis of 4-(4-chloro-phenyl)-piperidine-4-carboxylic acid dimethylamide hydrochloride (Compound 2-3)

Compound 2-2 (6.1 g 17 mmol) was dissolved in 4 M hydrogen chloride in dioxane (5 mL) and stirred at rt for 1 hr. Concentration in vacuo gave Compound 2-3-HCl (4.2 g, 14 mmol, 82%) as a white solid, which is carried forward without purification. MS (ES$^+$) m/z 267.1 (M+1); Anal Calcd. for $C_{14}H_{19}ClN_2O$—HCl—$H_2O$; C, 52.34; H, 6.90; N, 8.72. Found: C, 52.28; H, 6.71; N, 8.71.

Step 3. Synthesis of 4-(4-chloro-phenyl)-1-[2-(2-oxo-3,4-dihydro-2H-quinolin-1-yl)-ethyl]-piperidine-4-carboxylic acid dimethylamide (Compound 115)

Compound 115 was prepared by the same method as Compound 86 with the exception that Compound 2-3 was used instead of Compound 1-9 and that Compound 1-8 was used instead of Compound 1-4. Compound 115 was isolated as a white solid (53%, mp 243-245° C.). $^1$H (300 MHz, CDCl$_3$,) δ 7.44-7.01 (m, 8H), 4.55 (m, 2H), 3.62 (m, 2H), 3.31-2.40 (m, 18H); MS (ES$^+$) m/z 440.0 (M+1).

Using the procedure of Example 2, other compounds representative of the present invention may be prepared:

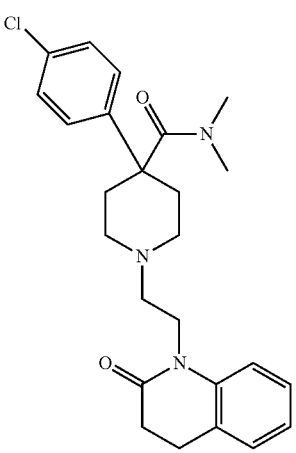

Cpd 115

Step 1. Synthesis of 4-(4-chlorophenyl)-4-dimethyl-carbamoyl-piperidine-1-carboxylic acid tert-butyl ester (Compound 2-2)

N-Boc-4-(4-chlorophenyl)-4-piperidine carboxylic acid Compound 2-1 (5.96 g, 18 mmol, Arch Chemical) was dissolved in DMF (175 mL) and chilled in an ice bath temp. To the solution was added N-methylmorpholine (5.76 mL, 53 mmol), HOBt (1.18 g, 8.8 mmol), dimethylamine hydrochloride (1.41 g, 18 mmol), and HBTU (10.0 g, 26 mmol). The solution was allowed to warm overnight to rt, poured into 1N sodium hydroxide solution (100 mL), and extracted with EtOAc (3×75 mL). The combined organic layers were washed with 1N NaOH (2×), 1N hydrochloric acid solution (2×), and brine (3×); and dried over Na$_2$SO$_4$ and concentrated to give Compound 2-2 (6.1 g, 17 mmol, 94%) as a white solid. $^1$H NMR (300 MHz, CDCl$_3$,) δ 7.32 (d, J=9 Hz, 2H), 7.17 (d, J=9 Hz, 2H), 4.2-3.8 (br m, 2H), 3.0-2.6 (br m, 2H), 2.96 (s, 3H), 2.80 (s, 3H), 2.25 (m, 2H), 2.1-1.7 (br m, 2H), 1.45 (s, 9H).

| Cpd | Name | MS |
|---|---|---|
| 103 | 1-[2-(3-oxo-2,3-dihydro-benzo[1,4]oxazin-4-yl)-ethyl]-4-phenyl-piperidine-4-carboxylic acid dimethyl amide | 408.1 |
| 104 | 1-[2-(3-oxo-2,3-dihydro-benzo[1,4]oxazin-4-yl)-ethyl]-4-phenyl-piperidine-4-carboxylic acid benzylamide | 470.2 |
| 105 | 1-[2-(3-oxo-2,3-dihydro-benzo[1,4]oxazin-4-yl)-ethyl]-4-phenyl-piperidine-4-carboxylic acid phenethyl-amide | 484.3 |
| 106 | 1-[2-(3-oxo-2,3-dihydro-benzo[1,4]oxazin-4-yl)-ethyl]-4-phenyl-piperidine-4-carboxylic acid methyl-phenethyl-amide | 498.1 |
| 107 | 1-[2-(3-oxo-2,3-dihydro-benzo[1,4]oxazin-4-yl)-ethyl]-4-phenyl-piperidine-4-carboxylic acid (3-phenyl-propyl)-amide | 498.1 |
| 108 | 1-[2-(3-oxo-2,3-dihydro-benzo[1,4]oxazin-4-yl)-ethyl]-4-phenyl-piperidine-4-carboxylic acid (4-phenyl-butyl)-amide | 512.3 |
| 109 | 4-(4-chloro-phenyl)-1-[2-(3-oxo-2,3-dihydro-benzo[1,4]oxazin-4-yl)-ethyl]-piperidine-4-carboxylic acid phenethyl-amide | 518.2 |
| 110 | 1-[2-(6-chloro-3-oxo-2,3-dihydro-benzo[1,4]oxazin-4-yl)-ethyl]-4-(4-chloro-phenyl)-piperidine-4-carboxylic acid dimethylamide | 476.2 |
| 111 | 4-(4-chloro-phenyl)-1-[2-(6-methyl-3-oxo-2,3-dihydro-benzo[1,4]oxazin-4-yl)-ethyl]-piperidine-4-carboxylic acid dimethylamide | 456.1 |
| 112 | 4-(4-chloro-phenyl)-1-[2-(6-fluoro-3-oxo-2,3-dihydro-benzo[1,4]oxazin-4-yl)-ethyl]-piperidine-4-carboxylic acid dimethylamide | 460.0 |
| 113 | 4-(4-chloro-phenyl)-1-[2-(3-oxo-2,3-dihydro-benzo[1,4]oxazin-4-yl)-ethyl]-piperidine-4-carboxylic acid dimethylamide | 442.2 |
| 114 | 4-(4-chloro-phenyl)-1-[2-(3-oxo-2,3-dihydro-benzo[1,4]thiazin-4-yl)-ethyl]-piperidine-4-carboxylic acid dimethylamide | 458.0 |

Example 3

2-{1-[2-(3-oxo-2,3-dihydro-benzol[1,4]oxazin-4-yl)-ethyl-piperidin-4-yl}-N-(3-phenyl-propyl)-benzamide (Compound 3)
N-(2-naphthalen-2-yl-ethyl)-2-{1-[2-(3-oxo-2,3-dihydro-benzo[1,4]oxazin-4-yl)-ethyl]-piperidin-4-yl}-benzamide (Compound 20)

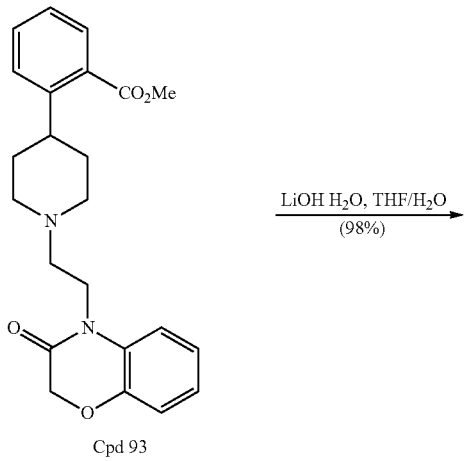

Cpd 93

LiOH H₂O, THF/H₂O
(98%)

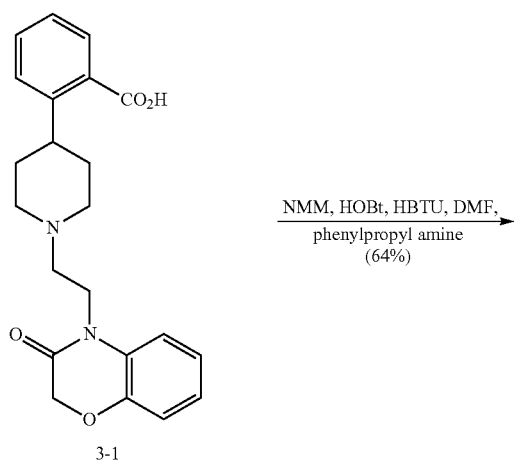

3-1

NMM, HOBt, HBTU, DMF,
phenylpropyl amine
(64%)

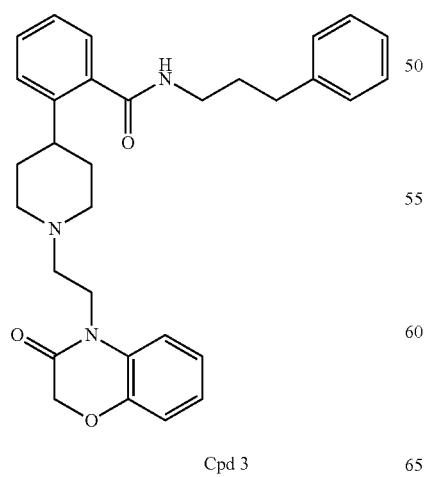

Cpd 3

Step 1. Synthesis of 2-{1-[2-(3-oxo-2,3-dihydro-benzo[1,4]oxazin-4-yl)-ethyl]-piperidin-4-yl}-benzoic acid (Compound 3-1)

2-{1-[2-(3-oxo-2,3-dihydro-benzo[1,4]oxazin-4-yl)-ethyl]-piperidin-4-yl}-benzoic acid methyl ester Compound 93 (1.2 g, 3.0 mmol) was dissolved in THF (10 mL) and treated with lithium hydroxide monohydrate (864 mg, 21 mmol). The reaction mixture was heated to 40° C. for 24 hrs, cooled to rt, adjusted to pH 3 with 1N HCl, and concentrated in vacuo. Purification by Gilson HPLC (elution with 10 to 90 gradient of H₂O 0.2% TFA buffer/acetonitrile with 0.1% TFA buffer) afforded Compound 3-1 as a white solid (1.45 g, 2.93 mmol, 98%). $^1$H NMR (300 MHz, CDCl$_3$) δ 8.71 (d, J=5 Hz, 1H), 7.92 (m, 1H), 7.59-7.43 (m, 2H), 7.32-7.22 (m, 1H), 7.14-6.89 (m, 3H), 4.62 (s, 2H), 3.97-3.68 (m, 2H), 3.45-2.94 (m, 4H), 2.71-2.33 (m, 3H), 2.13-1.96 (m, 2H), 1.80-1.65 (m, 2H); MS (ES⁺) m/z 381.1 (M+1).

Step 2. Synthesis of 2-{1-[2-(3-oxo-2,3-dihydro-benzo[1,4]oxazin-4-yl)-ethyl-piperidin-4-yl}-N-(3-phenyl-propyl)-benzamide (Compound 3)

Compound 3-1 (150 mg, 0.39 mmol) was dissolved in dry DMF (10 mL), and treated with N-methylmorpholine (162 μL, 1.5 mmol), 1-hydroxybenzotriazole (6.3 mg, 0.047 mmol), and phenylpropylamine (70 μL, 0.49 mmol). The reaction mixture was chilled to 4° C. in an ice bath, treated with HBTU (280 mg, 0.74 mmol), and stirred overnight, allowing it to warm to rt. The reaction mixture was poured into EtOAc (50 mL) and washed with 1 N sodium hydroxide solution (3×), 1 N hydrochloric acid solution (3×), and brine. The organic layer was dried over Na₂SO₄ and concentrated to give a crude product, which was purified on silica gel (elution with 90% EtOAc in hexane) to give Compound 3 (125 mg, 0.25 mmol, 64%) as a yellow oil. $^1$H NMR (300 MHz, CDCl$_3$) δ 7.37-6.98 (m, 13H), 5.97 (t, J=6 Hz, 1H), 4.56 (s, 2H), 4.09 (t, J=7 Hz, 2H), 3.45 (t, J=7 Hz, 2H), 3.10-2.93 (m, 3H), 2.74-2.61 (m, 4H), 2.27, (t of d, J=8 and 3 Hz, 2H), 2.02-1.83 (m, 6H); MS (ES⁺) m/z 498.3 (M+1); Anal Calcd. for C$_{31}$H$_{35}$N$_3$O$_3$-0.18H$_2$O-0.62 HCl: C, 71.13; H, 6.93; N, 8.03; H₂O, 0.62. found C, 71.13; H, 6.90; N, 7.91; KF=0.60.

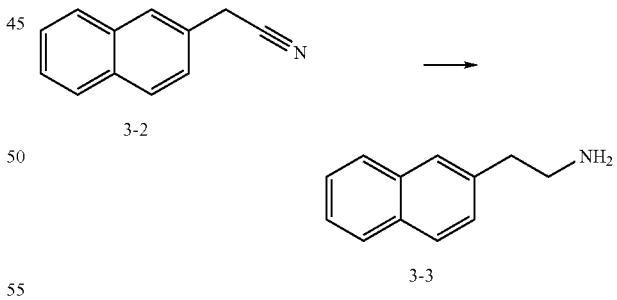

Step 3. Synthesis of 2-naphthalen-2-yl-ethylamine (Compound 3-3)

Arylethylamines that were not commercially available were made by the following procedure. 2-Naphthylacetonitrile Compound 3-2 (16.7 g, 0.10 mol) in anhydrous tetrahydrofuran (50 mL) was added to 1M solution of BH$_3$-THF (250 mL, 0.25 mol) over 10 min at room temperature. The reaction proceeds with an induction period of 2-4 min. Following the addition, the mixture was heated under reflux and under argon for one hour (TLC of a quenched aliquot showed no starting material). The reaction was cooled in an ice bath and 10% aqueous HCl (150 mL) was added with caution over a 30 min period (vigorous reaction with the first few drops). Following the addition concentrated hydrochloric acid (100 mL) was added and the mixture brought up to reflux for 30 min. The reaction was cooled in an ice bath and extracted once with ethyl ether. The aqueous layer was carefully brought to pH 12 with 40% sodium hydroxide solution (use of concentrated base allows for smaller volumes of the aqueous layer and simplifies the extraction of the amine) and extracted with diethyl ether (4×250 mL). The organic layer was washed with brine (50 mL), dried over sodium sulfate, and evaporated at reduced pressure below 40° C. The solvent was not completely removed to avoid loss of product. TLC (85:15 CHCl$_3$/MeOH, R$_f$=0.1) shows that the amine is essentially pure. Oxalic acid (9.0 g, 0.10 mole) was dissolved in methanol (10 mL) and added to the crude amine diluted with diethyl ether to a 300 mL volume. The white precipitate was collected by filtration, washed with ether, and dried in vacuo to provide Compound 3-3 (22.3 g, 85%) as the oxalate salt (mp=191-193° C.). Anal Calcd. for $C_{12}H_{13}N$-0.85 $C_2O_4H_2$: C, 66.42; H, 5.98. Found: C, 66.67; H, 6.05. Compound 3-3 freebase: $^1$H NMR (300 MHz, CDCl$_3$) δ 7.83-7.77 (m, 3H), 7.65 (s, 1H), 7.49-7.40 (m, 2H), 7.34 (d of d, J=8.5 and 1.6 Hz, 1H), 3.06 (t, J=7 Hz, 2H), 2.92 (t, J=7 Hz, 2H).

Step 4. Synthesis of N-(2-naphthalen-2-yl-ethyl)-2-{1-[2-(3-oxo-2,3-dihydro-benzo[1,4]oxazin-4-yl)-ethyl]-piperidin-4-yl}-benzamide (Compound 20)

Compound 20 was prepared by the method of step 2 above with the exception that Compound 3-3 was used instead of phenylpropylamine. MS (ES$^+$) m/z 534.4 (M+1).

Using the procedure of Example 3, other compounds representative of the present invention may be prepared:

| Cpd | Name | MS |
|---|---|---|
| 1 | 2-{1-[2-(3-oxo-2,3-dihydro-benzo[1,4]oxazin-4-yl)-ethyl]-piperidin-4-yl}-N-phenethyl-benzamide | 484.4 |
| 2 | N-benzyl-2-{1-[2-(3-oxo-2,3-dihydro-benzo[1,4]oxazin-4-yl)-ethyl]-piperidin-4-yl}-benzamide | 470.2 |
| 4 | 2-{1-[2-(3-oxo-2,3-dihydro-benzo[1,4]oxazin-4-yl)-ethyl]-piperidin-4-yl}-N-(4-phenyl-butyl)-benzamide | 512.4 |
| 5 | N-benzyl-N-methyl-2-{1-[2-(3-oxo-2,3-dihydro-benzo[1,4]oxazin-4-yl)-ethyl]-piperidin-4-yl}-benzamide | 484.4 |
| 6 | N-[2-(3-methoxy-phenyl)-ethyl]-2-{1-[2-(3-oxo-2,3-dihydro-benzo[1,4]oxazin-4-yl)-ethyl]-piperidin-4-yl}-benzamide | 514.3 |
| 7 | N-[2-(2,4-dichloro-phenyl)-ethyl]-2-{1-[2-(3-oxo-2,3-dihydro-benzo[1,4]oxazin-4-yl)-ethyl]-piperidin-4-yl}-benzamide | 552.3 |
| 8 | N-[2-(2-chloro-phenyl)-ethyl]-2-{1-[2-(3-oxo-2,3-dihydro-benzo[1,4]oxazin-4-yl)-ethyl]-piperidin-4-yl}-benzamide | 518.2 |
| 9 | N-[2-(4-chloro-phenyl)-ethyl]-2-{1-[2-(3-oxo-2,3-dihydro-benzo[1,4]oxazin-4-yl)-ethyl]-piperidin-4-yl}-benzamide | 518.0 |
| 10 | N-[2-(3,4-dimethoxy-phenyl)-ethyl]-2-{1-[2-(3-oxo-2,3-dihydro-benzo[1,4]oxazin-4-yl)-ethyl]-piperidin-4-yl}-benzamide | 544.2 |
| 11 | N-[2-(3,4-dichloro-phenyl)-ethyl]-2-{1-[2-(3-oxo-2,3-dihydro-benzo[1,4]oxazin-4-yl)-ethyl]-piperidin-4-yl}-benzamide | 552.2 |
| 12 | N-[2-(4-chloro-phenyl)-1-methyl-ethyl]-2-{1-[2-(3-oxo-2,3-dihydro-benzo[1,4]oxazin-4-yl)-ethyl]-piperidin-4-yl}-benzamide | 532.0 |
| 13 | N-[2-(2,5-dimethoxy-phenyl)-ethyl]-2-{1-[2-(3-oxo-2,3-dihydro-benzo[1,4]oxazin-4-yl)-ethyl]-piperidin-4-yl}-benzamide | 544.4 |
| 14 | N-[2-(4-methoxy-phenyl)-ethyl]-2-{1-[2-(3-oxo-2,3-dihydro-benzo[1,4]oxazin-4-yl)-ethyl]-piperidin-4-yl}-benzamide | 514.2 |
| 15 | N-[2-(2-methoxy-phenyl)-ethyl]-2-{1-[2-(3-oxo-2,3-dihydro-benzo[1,4]oxazin-4-yl)-ethyl]-piperidin-4-yl}-benzamide | 514.1 |
| 16 | N-[2-(4-fluoro-phenyl)-ethyl]-2-{1-[2-(3-oxo-2,3-dihydro-benzo[1,4]oxazin-4-yl)-ethyl]-piperidin-4-yl}-benzamide | 502.0 |
| 17 | N-[2-(3,5-dimethoxy-phenyl)-ethyl]-2-{1-[2-(3-oxo-2,3-dihydro-benzo[1,4]oxazin-4-yl)-ethyl]-piperidin-4-yl}-benzamide | 544.1 |
| 18 | N-methyl-2-{1-[2-(3-oxo-2,3-dihydro-benzo[1,4]oxazin-4-yl)-ethyl]-piperidin-4-yl}-N-phenethyl-benzamide | 498.3 |
| 19 | N-[2-(3,4-difluoro-phenyl)-ethyl]-2-{1-[2-(3-oxo-2,3-dihydro-benzo[1,4]oxazin-4-yl)-ethyl]-piperidin-4-yl}-benzamide | 520.2 |
| 21 | N-[2-(3,5-difluoro-phenyl)-ethyl]-2-{1-[2-(3-oxo-2,3-dihydro-benzo[1,4]oxazin-4-yl)-ethyl]-piperidin-4-yl}-benzamide | 520.4 |
| 22 | N-[2-(2,5-difluoro-phenyl)-ethyl]-2-{1-[2-(3-oxo-2,3-dihydro-benzo[1,4]oxazin-4-yl)-ethyl]-piperidin-4-yl}-benzamide | 520.1 |
| 23 | N-[2-(2,3-difluoro-phenyl)-ethyl]-2-{1-[2-(3-oxo-2,3-dihydro-benzo[1,4]oxazin-4-yl)-ethyl]-piperidin-4-yl}-benzamide | 520.1 |
| 24 | N-cyclopropylmethyl-2-{1-[2-(3-oxo-2,3-dihydro-benzo[1,4]oxazin-4-yl)-ethyl]-piperidin-4-yl}-benzamide | 434.1 |
| 25 | N-(1-methyl-3-phenyl-propyl)-2-{1-[2-(3-oxo-2,3-dihydro-benzo[1,4]oxazin-4-yl)-ethyl]-piperidin-4-yl}-benzamide | 512.1 |
| 26 | N-[2-(1H-indol-3-yl)-ethyl]-2-{1-[2-(3-oxo-2,3-dihydro-benzo[1,4]oxazin-4-yl)-ethyl]-piperidin-4-yl}-benzamide | 523.1 |
| 27 | N-indan-1-yl-2-{1-[2-(3-oxo-2,3-dihydro-benzo[1,4]oxazin-4-yl)-ethyl]-piperidin-4-yl}-benzamide | 496.2 |
| 28 | 2-{1-[2-(3-oxo-2,3-dihydro-benzo[1,4]oxazin-4-yl)-ethyl]-piperidin-4-yl}-N-(2-phenyl-propyl)-benzamide | 497.9 |
| 29 | 2-{1-[2-(3-oxo-2,3-dihydro-benzo[1,4]oxazin-4-yl)-ethyl]-piperidin-4-yl}-N-propyl-benzamide | 422.2 |
| 30 | 2-{1-[2-(3-oxo-2,3-dihydro-benzo[1,4]oxazin-4-yl)-ethyl]-piperidin-4-yl}-N-(2-pyrrolidin-1-yl-ethyl)-benzamide | 477.2 |
| 31 | N-cyclohexylmethyl-2-{1-[2-(3-oxo-2,3-dihydro-benzo[1,4]oxazin-4-yl)-ethyl]-piperidin-4-yl}-benzamide | 476.3 |
| 32 | N-furan-2-ylmethyl-N-methyl-2-{1-[2-(3-oxo-2,3-dihydro-benzo[1,4]oxazin-4-yl)-ethyl]-piperidin-4-yl}-benzamide | 474.2 |
| 33 | N-(2-{1-[2-(3-oxo-2,3-dihydro-benzo[1,4]oxazin-4-yl)-ethyl]-piperidin-4-yl}-phenyl)-3-phenyl-propionamide | 483.8 |
| 34 | N-[2-(4-bromo-phenyl)-ethyl]-2-{1-[2-(3-oxo-2,3-dihydro-benzo[1,4]oxazin-4-yl)-ethyl]-piperidin-4-yl}-benzamide | 563.6 |
| 35 | [4-(2-{1-[2-(3-oxo-2,3-dihydro-benzo[1,4]oxazin-4-yl)-ethyl]-piperidin-4-yl}-benzoylamino)-butyl]-carbamic acid tert-butyl ester | 551.7 |
| 36 | N-(2-methoxy-ethyl)-2-{1-[2-(3-oxo-2,3-dihydro-benzo[1,4]oxazin-4-yl)-ethyl]-piperidin-4-yl}-benzamide | 438.3 |
| 37 | N-(3-methoxy-propyl)-2-{1-[2-(3-oxo-2,3-dihydro-benzo[1,4]oxazin-4-yl)-ethyl]-piperidin-4-yl}-benzamide | 452.1 |
| 38 | N-(3-ethoxy-propyl)-2-{1-[2-(3-oxo-2,3-dihydro-benzo[1,4]oxazin-4-yl)-ethyl]-piperidin-4-yl}-benzamide | 466.3 |
| 39 | N-(3-hydroxy-propyl)-2-{1-[2-(3-oxo-2,3-dihydro-benzo[1,4]oxazin-4-yl)-ethyl]-piperidin-4-yl}-benzamide | 438.3 |
| 40 | 2-{1-[2-(3-oxo-2,3-dihydro-benzo[1,4]oxazin-4-yl)-ethyl]-piperidin-4-yl}-N-[2-(4-trifluoromethyl-phenyl)-ethyl]-benzamide | 552.4 |
| 41 | 2-{1-[2-(3-oxo-2,3-dihydro-benzo[1,4]oxazin-4-yl)-ethyl]-piperidin-4-yl}-N-pyridin-2-ylmethyl-benzamide | 471.2 |
| 42 | 2-{1-[2-(3-oxo-2,3-dihydro-benzo[1,4]oxazin-4-yl)-ethyl]-piperidin-4-yl}-N-(2-pyridin-2-yl-ethyl)-benzamide | 485.6 |
| 43 | 2-{1-[2-(3-oxo-2,3-dihydro-benzo[1,4]oxazin-4-yl)-ethyl]-piperidin-4-yl}-N-pyridin-3-ylmethyl-benzamide | 471.2 |
| 44 | 2-{1-[2-(3-oxo-2,3-dihydro-benzo[1,4]oxazin-4-yl)-ethyl]-piperidin-4-yl}-N-pyridin-4-ylmethyl-benzamide | 470.8 |
| 45 | 2-{1-[2-(3-oxo-2,3-dihydro-benzo[1,4]oxazin-4-yl)-ethyl]-piperidin-4-yl}-N-(2-pyridin-4-yl-ethyl)-benzamide | 485.1 |
| 46 | 2-{1-[2-(3-oxo-2,3-dihydro-benzo[1,4]oxazin-4-yl)-ethyl]-piperidin-4-yl}-N-thiophen-2-ylmethyl-benzamide | 476.0 |
| 47 | 2-{1-[2-(3-oxo-2,3-dihydro-benzo[1,4]oxazin-4-yl)-ethyl]-piperidin-4-yl}-N-(2-thiophen-2-yl-ethyl)-benzamide | 490.2 |
| 48 | N-(3-imidazol-1-yl-propyl)-2-{1-[2-(3-oxo-2,3-dihydro-benzo[1,4]oxazin-4-yl)-ethyl]-piperidin-4-yl}-benzamide | 488.2 |
| 49 | N-(2-acetylamino-ethyl)-2-{1-[2-(3-oxo-2,3-dihydro-benzo[1,4]oxazin-4-yl)-ethyl]-piperidin-4-yl}-benzamide | 465.0 |
| 50 | 4-[(2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester | 577.4 |
| 51 | 2-{1-[2-(3-oxo-2,3-dihydro-benzo[1,4]oxazin-4-yl)-ethyl]-piperidin-4-yl}-N-[3-(2-oxo-pyrrolidin-1-yl)-propyl]-benzamide | 505.5 |
| 52 | 2-{1-[2-(3-oxo-2,3-dihydro-benzo[1,4]oxazin-4-yl)-ethyl]-piperidin-4-yl}-N-(2-piperidin-1-yl-ethyl)-benzamide | 491.5 |

103
-continued

| Cpd | Name | MS |
|---|---|---|
| 53 | 4-(2-{4-[2-(3,4-dihydro-1H-isoquinoline-2-carbonyl)-phenyl]-piperidin-1-yl}-ethyl)-4H-benzo[1,4]oxazin-3-one | 496.2 |
| 54 | N-[2-(3-naphthalen-2-yl-ureido)-ethyl]-2-{1-[2-(3-oxo-2,3-dihydro-benzo[1,4]oxazin-4-yl)-ethyl]-piperidin-4-yl}-benzamide | 592.2 |
| 55 | N-[2-(3-naphthalen-1-yl-ureido)-ethyl]-2-{1-[2-(3-oxo-2,3-dihydro-benzo[1,4]oxazin-4-yl)-ethyl]-piperidin-4-yl}-benzamide | 592.2 |

Example 4

4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester (Compound 66)

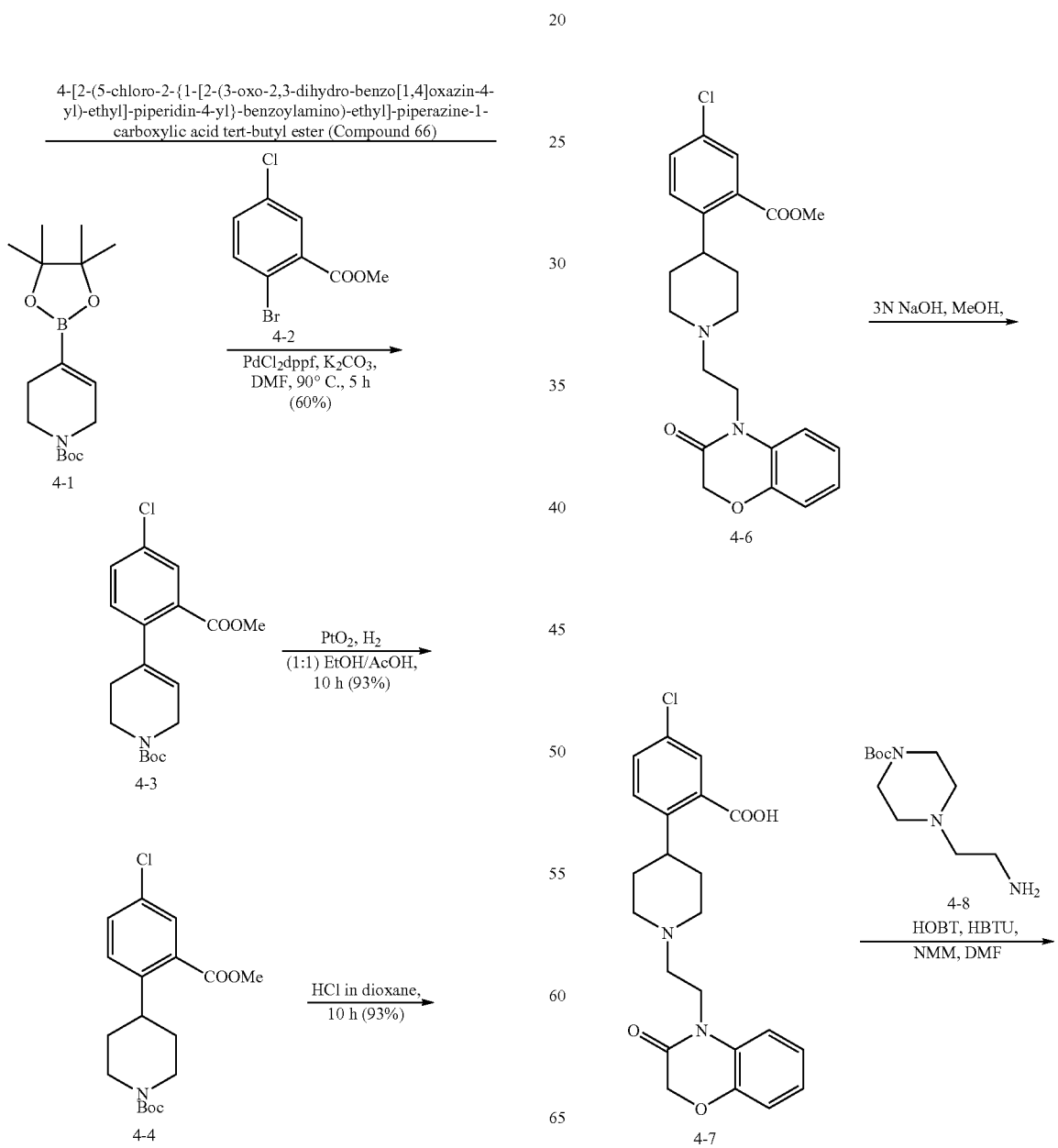

-continued

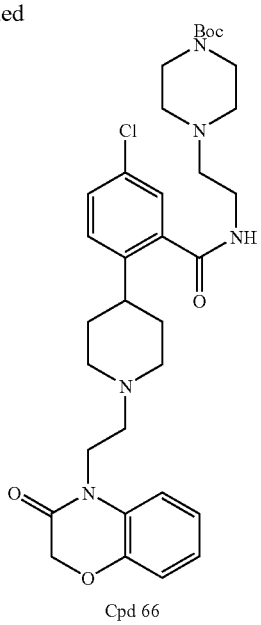

Cpd 66

Step 1. Synthesis of 4-(4-chloro-2-methoxycarbonyl-phenyl)-3,6-dihydro-2H-pyridine-1-carboxylic acid tert-butyl ester (Compound 4-3)

A solution of 2-bromo-5-chloro-benzoic acid methyl ester Compound 4-2 (5.08 g, 20.4 mmol), the boronate Compound 4-1 (6.00 g, 19.4 mmol), PdCl₂dppf-CH₂Cl₂ (1.06 g, 1.30 mmol) and K₂CO₃ (8.9 g, 58.21 mmol) in DMF and EtOH (4:1, 90 mL) was prepared in a thick walled tube. The mixture was stirred under argon at rt for 5-10 min and the tube was closed and heated at 90° C. for 5 hrs (4-16 hrs for other examples). The mixture was cooled to rt then filtered thru a pad of Celite®, washing with EtOAc. The solvent was evaporated and purified by flash chromatography (gradient elution with 5-50% EtOAc in heptane with 0.1% TEA). The desired product Compound 4-3 was isolated as yellow liquid (4.05 g, 60%). ¹H NMR (300 MHz, CDCl₃) δ 7.82 (d, J=2.2 Hz, 1H), 7.43 (d of d, J=8.2 and 2.2 Hz, 1H), 7.14 (d, J=8.2 Hz, 1H), 5.51 (br s, 1H), 4.02 (br s, 2H), 3.85 (s, 3H), 3.63 (t, J=5.6 Hz, 2H), 2.30 (br s, 2H), 1.50 (s, 9H); MS (ES⁺) m/z 374.0 (M+Na).

Step 2. Synthesis of 4-(4-chloro-2-methoxycarbonyl-phenyl)-piperidine-1-carboxylic acid tert-butyl ester (Compound 4-4)

Compound 4-3 (2.73 g, 7.76 mmol), EtOH/AcOH (1:1, 60 mL) and PtO₂ (0.895 g) were shaken in a Parr apparatus (15 psig of hydrogen) for 10 hrs. The reaction mixture was filtered thru Celite®, washing with ethanol. The solution was concentrated, and the residue was diluted with dichloromethane and washed with saturated NaHCO₃. The aqueous layer was again extracted with dichloromethane, and the combined organic layers were dried over anhydrous Na₂SO₄, filtered and concentrated. The product was purified by flash chromatography (gradient elution with 15-50% ethylacetate (0.1% TEA) in heptane. The desired product Compound 4-4 was isolated as thick colorless oil (2.55 g, 93%). ¹H NMR (300 MHz, CDCl₃) δ 7.79 (d, J=2.3 Hz, 1H), 7.43 (d of d, J=8.5 and 2.3 Hz, 1H), 7.28 (d, J=8.5 Hz, 1H), 4.22 (m, 2H), 3.91 (s, 3H), 3.52 (m, 1H), 2.82 (m, 2H), 2.8-1.5 (m, 4H), 1.48 (s, 9H);

MS (ES⁺) m/z 253.8 (M-Boc+1); HRMS (FAB⁺) Calcd for C₁₈H₂₃ClNO₄: 352.1316. Found: 352.1329.

Step 3. Synthesis of 5-chloro-2-piperidin-4-yl-benzoic acid methyl ester (Compound 4-5)

Compound 4-4 (40 mg, 0.11 mmol), dioxane (3 mL), 4N HCl in dioxane (3 mL) and a drop of anisole were added and stirred at rt for 2 hrs. The reaction mixture was concentrated, triturated with ether and dried in vacuo. Compound 4-5 was isolated as a white solid (33 mg, 100%). MS (ES⁺) m/z 253.7 (M+1).

Step 4. Synthesis of 5-Chloro-2-{1-{2-(3-oxo-2,3-dihydro-benzo[1,4]oxazin-4-yl)-ethyl]-piperidin-4-yl}-benzoic acid methyl ester (Compound 4-6)

Intermediate Compound 4-5 (0.80 g, 2.8 mmol) was dissolved in dichloroethane (20 mL) and triethylamine (0.42 mL, 3.0 mmol) was added to neutralize the HCl salt of Compound 4-5 to give the free amine. Benzoxazinone aldehyde Compound 1-4 (0.52 g, 2.8 mmol) was added at rt and stirring was continued for 45 min. Tetramethylammonium triacetoxyborohydride was added and the reaction mixture was stirred for 2 hrs, quenched with NH₄OH/H₂O (1:1, 5 mL), washed with NH₄OH:H₂O (1:1, 2×10 mL), dried over anhydrous Na₂SO₄, filtered, concentrated and purified by flash chromatography (gradient elution with 25-100% EtOAc in heptane with 0.1% TEA). The product Compound 4-6 was isolated as white solid (0.86 g, 74%). ¹H NMR (300 MHz, CDCl₃) δ 7.77 (m, 1H), 7.45-7.30 (m, 2H), 7.07-7.01 (m, 4H), 4.61 (s, 2H), 4.13 (m, 2H), 3.90 (s, 3H), 3.34 (m, 1H), 3.12 (m, 2H), 2.67 (m, 2H), 2.26 (m, 2H), 1.8-1.6 (m, 4H); MS (ES⁺) m/z 429.0 (M+1).

Step 5. Synthesis of 5-chloro-2-[1-[2(3-oxo-2,3-dihydro-benzo[1,4]oxazin-4-yl)-ethyl]-piperidin-4-yl}-benzoic acid (Compound 4-7)

Compound 4-6 (1.00 g, 2.33 mmol) was dissolved in methanol (3 mL), treated with 3N sodium hydroxide solution (3.1 mL, 9.33 mmol) at rt, and stirred for 24 hrs. The reaction was neutralized with 2N hydrochloric acid solution (7 mL, 14 mmol) and purified by RP HPLC (gradient elution with 15-90% acetonitrile in water, each containing 0.1% TFA). Lyophilization afforded product Compound 4-7 as a white solid (trifluoroacetate salt, 0.62 g, 64%). ¹H NMR (300 MHz, DMSO) δ 7.76 (br s, 1H), 7.64 (br d, J=8 Hz, 1H), 7.41 (d, J=8.5 Hz, 1H), 7.30 (d, J=6.9 Hz, 1H), 7.11-7.06 (m, 3H), 4.70 (s, 2H), 4.33 (m, 2H), 3.86-3.20 (m, 7H), 2.04-1.86 (m, 4H); MS (ES⁺) m/z 414.9 (M+1); Anal Calcd. for C₂₂H₂₃ClN₂O₄·1.75CF₃CO₂H: C, 50.05; H, 4.08; N, 4.60. Found: C, 50.11; H, 4.23; N, 4.56.

Step 6. Synthesis of 4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester (Compound 66)

A solution of Compound 4-7 (0.24 g, 0.58 mmol) in dimethylformamide (3 mL) was combined with N-methylmorpholine (0.19 mL, 1.74 mmol), 1-hydroxybenzotriazole (0.04 g, 0.29 mmol), O-benzotriazol-1-yl-N,N,N',N'-tetramethyluronium hexafluorophosphate (HBTU, 0.26 g, 0.70 mmol) and Compound 4-8 (0.16 g, 0.70 mmol). The reaction mixture was stirred overnight at rt, quenched with saturated ammonium chloride, and extracted with ethylacetate. The combined organic layers were dried over anhydrous sodium sulfate, filtered and concentrated. The crude product was purified by RP HPLC (gradient elution with 10-60% acetonitrile in water, each with 0.1% TFA) and lyophilized to yield Compound 66 as white solid (trifluoroacetate salt, 0.26 g, 72%).
$^1$H NMR (300 MHz, DMSO) δ 7.58-7.53 (m, 2H), 7.37 (d, J=8.5 Hz, 1H), 7.30 (m, 1H), 7.12-7.05 (m, 3H), 4.70 (s, 2H), 4.3-3.1 (m, 21H), 2.0-1.8 (m, 4H), 1.42 (s, 9H); MS (ES$^+$) m/z 626.1 (M+1); Anal Calcd. for $C_{33}H_{44}ClN_5O_5 \cdot 3.6CF_3CO_2H$: C, 46.58; H, 4.63; N, 6.76. Found: C, 46.25, H, 4.48; N, 6.73.

Using the procedure of Example 4, other compounds representative of the present invention may be prepared:

| Cpd | Name | MS |
|---|---|---|
| 56 | 5-chloro-2-{1-[2-(3-oxo-2,3-dihydro-benzo[1,4]oxazin-4-yl)-ethyl]-piperidin-4-yl}-benzoic acid methyl ester | 429.0 |
| 57 | 5-chloro-2-{1-[2-(3-oxo-2,3-dihydro-benzo[1,4]oxazin-4-yl)-ethyl]-piperidin-4-yl}-N-phenethyl-benzamide | 518.2 |
| 58 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester | 611.3 |
| 59 | 5-chloro-N,N-dimethyl-2-{1-[2-(3-oxo-2,3-dihydro-benzo[1,4]oxazin-4-yl)-ethyl]-piperidin-4-yl}-benzamide | 442.2 |
| 60 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid tert-butyl ester | 585.3 |
| 61 | 5-chloro-N-(2-naphthalen-2-yl-ethyl)-2-{1-[2-(3-oxo-2,3-dihydro-benzo[1,4]oxazin-4-yl)-ethyl]-piperidin-4-yl}-benzamide | 568.0 |
| 62 | 5-chloro-N-[2-(1H-indol-3-yl)-ethyl]-2-{1-[2-(3-oxo-2,3-dihydro-benzo[1,4]oxazin-4-yl)-ethyl]-piperidin-4-yl}-benzamide | 557.0 |
| 63 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzyl ester | 645.3 |
| 64 | N-(1-benzoyl-piperidin-4-ylmethyl)-5-chloro-2-{1-[2-(3-oxo-2,3-dihydro-benzo[1,4]oxazin-4-yl)-ethyl]-piperidin-4-yl}-benzamide | 615.3 |
| 65 | 5-chloro-N-[1-(3,3-dimethyl-butyryl)-piperidin-4-ylmethyl]-2-{1-[2-(3-oxo-2,3-dihydro-benzo[1,4]oxazin-4-yl)-ethyl]-piperidin-4-yl}-benzamide | 609.2 |
| 67 | 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzylamide | 644.2 |
| 68 | 4-[2-(5-chloro-2-{1-[2-(3-oxo-2,3-dihydro-benzo[1,4]oxazin-4-yl)-ethyl]-piperidin-4-yl}-benzoylamino)-ethyl]-piperidine-1-carboxylic acid tert-butyl ester | 625.2 |
| 69 | [4-(5-chloro-2-{1-[2-(3-oxo-2,3-dihydro-benzo[1,4]oxazin-4-yl)-ethyl]-piperidin-4-yl}-benzoylamino)-butyl]-carbamic acid benzyl ester | 619.2 |
| 70 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid tert-butyl ester | 599.2 |
| 71 | 5-chloro-2-{1-[2-(3-oxo-2,3-dihydro-benzo[1,4]oxazin-4-yl)-ethyl]-piperidin-4-yl}-N-(2-piperidin-1-yl-ethyl)-benzamide | 525.1 |
| 72 | 5-chloro-2-{1-[2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide | 665.2 |
| 73 | 5-chloro-2-{1-[2-(3-oxo-2,3-dihydro-benzo[1,4]oxazin-4-yl)-ethyl]-piperidin-4-yl}-N-(2-piperazin-1-yl-ethyl)-benzamide | 526.0 |
| 74 | [6-(5-chloro-2-{1-[2-(3-oxo-2,3-dihydro-benzo[1,4]oxazin-4-yl)-ethyl]-piperidin-4-yl}-benzoylamino)-hexyl]-carbamic acid tert-butyl ester | 613.2 |
| 75 | [5-(5-chloro-2-{1-[2-(3-oxo-2,3-dihydro-benzo[1,4]oxazin-4-yl)-ethyl]-piperidin-4-yl}-benzoylamino)-pentyl]-carbamic acid benzyl ester | 633.0 |
| 76 | 5-chloro-N-[5-(3,3-dimethyl-butyrylamino)-pentyl]-2-{1-[2-(3-oxo-2,3-dihydro-benzo[1,4]oxazin-4-yl)-ethyl]-piperidin-4-yl}-benzamide | 597.2 |
| 77 | N-[5-(3-benzyl-ureido)-pentyl]-5-chloro-2-{1-[2-(3-oxo-2,3-dihydro-benzo[1,4]oxazin-4-yl)-ethyl]-piperidin-4-yl}-benzamide | 632.1 |
| 78 | 5-chloro-2-{1-[2-(3-oxo-2,3-dihydro-benzo[1,4]oxazin-4-yl)-ethyl]-piperidin-4-yl}-N-(5-phenylmethanesulfonylamino-pentyl)-benzamide | 653.3 |
| 79 | {2-[2-(5-chloro-2-{1-[2-(3-oxo-2,3-dihydro-benzo[1,4]oxazin-4-yl)-ethyl]-piperidin-4-yl}-benzoylamino)-ethoxy]-ethyl}-carbamic acid tert-butyl ester | 601.2 |
| 80 | 5-chloro-N-[5-(3-isopropyl-ureido)-pentyl]-2-{1-[2-(3-oxo-2,3-dihydro-benzo[1,4]oxazin-4-yl)-ethyl]-piperidin-4-yl}-benzamide | 584.1 |
| 81 | 5-chloro-2-{1-[2-(3-oxo-2,3-dihydro-benzo[1,4]oxazin-4-yl)-ethyl]-piperidin-4-yl}-N-[5-(3-phenyl-ureido)-pentyl]-benzamide | 618.2 |

-continued

| Cpd | Name | MS |
|---|---|---|
| 82 | 5-chloro-2-{1-[2-(3-oxo-2,3-dihydro-benzo[1,4]oxazin-4-yl)-ethyl]-piperidin-4-yl}-N-[5-(3-phenethyl-ureido)-pentyl]-benzamide | 645.9 |
| 83 | [5-(5-chloro-2-{1-[2-(2-oxo-3,4-dihydro-2H-quinolin-1-yl)-ethyl]-piperidin-4-yl}-benzoylamino)-pentyl]-carbamic acid tert-butyl ester | 597.3 |

Example 5

[5-(5-chloro-2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester (Compound 100)
[5-(5-chloro-2-{2,6-dimethyl-1-[2-(3-oxo-2,3-dihydro-benzo[1,4]oxazin-4-yl)-ethyl]-1,2,3,6-tetrahydro-pyridin-4-yl}-benzoylamino)pentyl-carbamic acid tert-butyl ester (Compound 102)

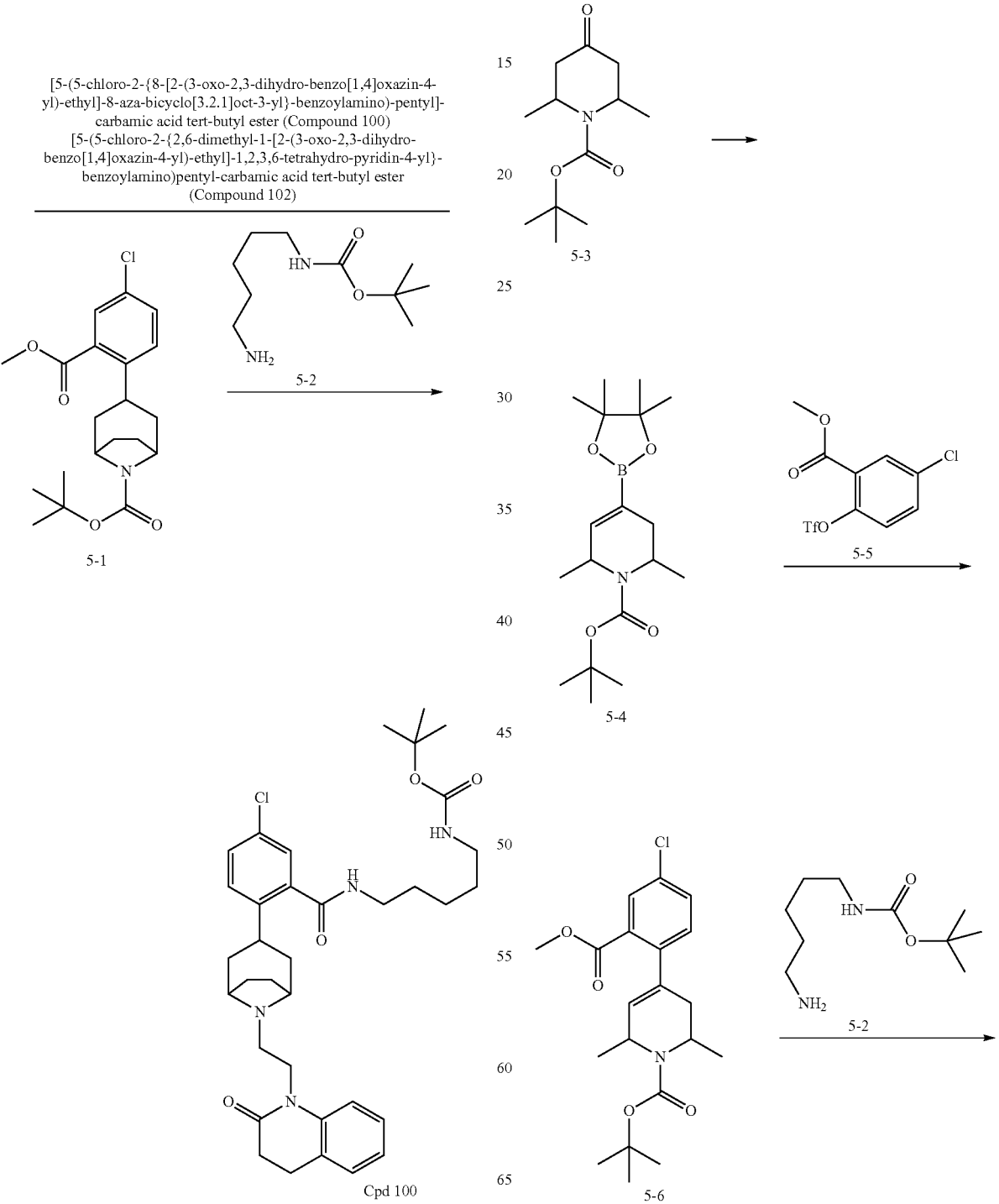

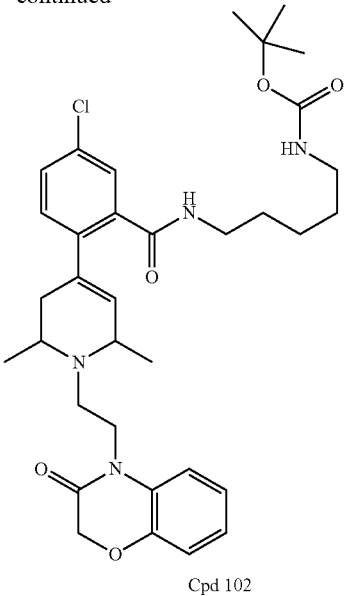

Cpd 102

Step 1. Synthesis of [5-(5-chloro-2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester (Compound 100)

Compound 100 was made using the methods described for Compound 66 (Example 4) with the exception that Compound 5-1 was used instead of Compound 4-4 and Compound 5-2 was used instead of Compound 4-8. Compound 5-1 was prepared as described and is shown as compound 10-f in "Convenient Preparation of Aryl-Substituted Nortropanes by Suzuki-Miyaura Methodology" S Ghosh, W A Kinney, D A Gauthier, E C Lawson, T Hudlicky, B E Maryanoff, *Can. J. Chem.* 2006, 84, 555-560. $^1$H NMR (300 MHz, CDCl$_3$) δ 7.6-7.0 (m, 7H), 4.61 (s, 2H), 4.7-4.3 (m, 2H), 4.16 (m, 2H), 3.7-2.8 (m, 7H), 2.5-1.3 (m, 14H), 1.88 (s, 9H); MS (ES$^+$) m/z 625.3 (M+1); HRMS (FAB$^+$) Calcd. for C34H45ClN4O5+H, 625.3157. Found: 625.3170.

Step 2. Synthesis of 2,6-dimethyl-4-oxo-piperidine-1-carboxylic acid tert-butyl ester (Compound 5-3)

Compound 5-3 was made in a manner similar to Hall, H. K. Jr.; *J. Am. Chem. Soc.,* 1957, 79, 5444-5447. Step 2a: Into a mixture of diethyl acetonedicarboxylate (103.6 g, 0.512 mol) and acetaldehyde (45.3 g, 1.33 mol) was bubbled ammonia gas until that liquid was saturated at −30° C. The solution was stored in freezer overnight. The yellow sludge was dissolved in dichloromethane (15 mL), filtered though silica gel and washed with EtOAc. The organic layer was concentrated to give diethyl 2,6-dimethyl-4-oxopiperidine-3,5-dicarboxylate as a thick yellow oil (92 g, 54%). Step 2b: A solution of the diester (90 g, 0.332 mol) in 10% aqueous hydrochloric acid solution (400 mL) was refluxed for overnight. Water was evaporated to yield 2,6-Dimethyl-4-piperidone/HCl, which was used for the next step without further purification. Step 2c: 2,6-Dimethyl-4-piperidone HCl salt (25.0 g, 0.153 mol) was partitioned into dioxane (250 mL) and H$_2$O (250 mL), and sodium bicarbonate (50 g, 0.59 mol) was added in several portions. Boc anhydride (80 g, 0.37 mol) was added and the resulting reaction mixture was stirred at rt overnight. The reaction mixture was evaporated to remove dioxane. The residue was extracted with Et$_2$O and the organic layer was washed with brine and dried over sodium sulfate. After evaporation, the crude product was purified by chromatography (gradient elution of 9-14% EtOAc in hexane) to give Compound 5-3 as a white solid (18.0 g, 52%, mixture of 70:30 trans:cis) (based on comparison to NMR spectra of trans Compound 5-3 reported by Beak, P.; Lee, W. K.; *J. Org. Chem.* 1993, 58, 1109-1117). MS (ES$^+$) m/z 128 (M-Boc+1).

Trans Compound 5-3: $^1$H NMR (300 MHz, CDCl$_3$) δ 4.39 (t, J=6.4 Hz, 2H, C-2,6), 2.85 (dd, J=18 and 6.4, Hz, 2H$_{ax}$, C-3,5), 2.38 (dd, J=18 and 1.8 Hz, 2H$_{eq}$, C-3,5), 1.50 (s, 9H, BOC), 1.26 (d, J=6.8 Hz, 6H, 2CH$_3$). $^{13}$C NMR (75 MHz, CDCl$_3$) δ 208.11, 154.59, 80.06, 46.70, 44.37, 28.66, 22.90.

Cis Compound 5-3: $^1$H NMR (300 MHz, CDCl$_3$) δ 4.73 (t of d, J=7.2 and 2.4 Hz, 2H, C-2,6), 2.73 (dd, J=14.8 and 8.0 Hz, 2H$_{ax}$, C-3,5), 2.28 (dd, J=14.8 and 2.4 Hz, 2H$_{eq}$, C-3,5), 1.49 (s, 9H, BOC), 1.28 (d, J=7.2 Hz, 6H, 2CH$_3$). $^{13}$C NMR (75 Hz, CDCl$_3$) δ 208.93, 154.69, 80.34, 48.63, 45.57, 28.60, 23.05.

Step 3. Synthesis of 2,6-dimethyl-4-(4,4,5,5-tetramethyl-[1,3,2]dioxaborolan-2-yl)-3,6-dihydro-2H-pyridine-1-carboxylic acid tert-butyl ester (Compound 5-4)

Compound 5-4 was prepared from Compound 5-3 (7.5 g, 33 mmol) by methods described in *Canadian Journal of Chemistry* 2006. Compound 5-4 was obtained in two batches: pure trans-Compound 5-4 as a solid (0.97 g, 9%, mp 84-85° C.) and a mixture of trans- and cis-isomers of Compound 5-4 as an oil (4.25 g, 2.25:1 of trans:cis, 38%).

Compound 5-4 (trans): $^1$H NMR (300 MHz, CDCl$_3$) δ 6.58 (m, 1H), 4.23-4.14 (m, 2H), 2.41-2.36 (m, 1H), 2.17 (d, J=18 Hz, 1H), 1.48 (s, 9H), 1.27 (br s, 15H), 1.05 (d, J=7 Hz, 3H); $^{13}$C NMR (75 Hz, CDCl$_3$) δ 155.70, 145.66, 83.81, 79.54, 48.59, 47.26, 31.20, 28.90, 25.19, 25.14, 21.11, 19.59; MS (EI$^+$) m/z 337 (M$^+$); HRMS (EI$^+$) Calcd. for C$_{18}$H$_{32}$NO$_4$B:; 337.2424. Found: 337.2433; R$_f$: 0.52 (pentane/EtOAc, 9:1); Anal Calcd. for C$_{18}$H$_{32}$NO$_4$B: C, 64.10; H, 9.56. Found: C, 64.15; H, 9.80.

Compound 5-4 (trans and cis in a ratio of 2.25:1): $^1$H NMR (300 MHz, CDCl$_3$) δ 6.58 (m, 0.7H), 6.39 (m, 0.3H), 4.56-4.31 (m, 0.6H), 4.23-4.14 (m, 1.4H), 2.41-2.04 (m, 2H), 1.47 (m, 9H), 1.27 (m, 15H), 1.09 (d, J=7 Hz, 0.9H), 1.05 (d, J=7 Hz, 2.1H); $^{13}$C NMR (75 Hz, CDCl$_3$) δ 155.65, 154.74, 145.60, 143.14, 83.76, 83.72, 79.47, 48.57, 48.42, 47.24, 43.43, 31.20, 28.89, 28.87, 25.36, 25.15, 25.10, 21.08, 20.91, 19.55; MS (EI$^+$) m/z 337 (M$^+$); HRMS (EI$^+$) Calcd. for C$_{18}$H$_{32}$NO$_4$B:; 337.2424. Found: 337.2424; R$_f$: 0.52 and 0.46 (pentane/EtOAc, 9:1); Anal Calcd. for C$_{18}$H$_{32}$NO$_4$B: C, 64.10; H, 9.56. Found: C, 63.97; H, 9.75.

Step 4. Synthesis of [5-(5-chloro-2-{2,6-dimethyl-1-[2-(3-oxo-2,3-dihydro-benzo[1,4]oxazin-4-yl)-ethyl]-1,2,3,6-tetrahydro-pyridin-4-yl}-benzoylamino)pentyl]-carbamic acid tert-butyl ester (Compound 102)

Compound 5-4, as a mixture of cis- and trans-isomers, was converted to Compound 5-6 by the methods described for the conversion of Compound 4-1 to Compound 4-3, with the exception that the triflate Compound 5-5 was utilized instead of the arylbromide Compound 4-2. Compound 5-6 was converted to Compound 102 in several steps by the methods described for the conversion of Compound 4-4 to Compound 66 (Example 4), utilizing amine Compound 5-2 in the final step instead of Compound 4-8. Compound 102 was isolated as a gummy solid (trifluoroacetate salt). $^1$H NMR (300 MHz, CDCl$_3$) δ 7.55 (d, J=2.2 Hz, 1H), 7.31 (d of d, J=8.2 and 2.2 Hz, 1H), 7.10-6.91 (m, 5H), 6.06, 5.67 (m, 1H), 4.60 (s, 2H), 4.01 (m, 2H), 3.4-2.0 (m, 10H), 1.56 (s, 9H), 1.6-1.3 (m, 6H), 1.19 (d, J=6.7 Hz, 3H), 1.05 (d, J=6.6 Hz, 3H); MS (ES$^+$) m/z 624.9 (M+1).

Using the procedure of Example 5, other compounds representative of the present invention may be prepared:

| Cpd | Name | MS |
|---|---|---|
| 94 | 4-[2-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-ethyl]-piperazine-1-carboxylic acid tert-butyl ester | 649.8 |
| 95 | [5-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-pentyl]-carbamic acid tert-butyl ester | 622.8 |
| 96 | 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester | 618.5 |
| 97 | [5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester | 591.5 |
| 98 | [5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester | 581.5 |
| 99 | 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester | 618.5 |
| 101 | 4-[2-(3-phenyl-8-aza-bicyclo[3.2.1]oct-8-yl)-ethyl]-4H-benzo[1,4]oxazin-3-one | 363.3 |

Example 6

4-[2-(4-phenyl-piperidin-1-yl)-propyl]-4H-benzo[1,4]oxazin-3-one (Compound 116)

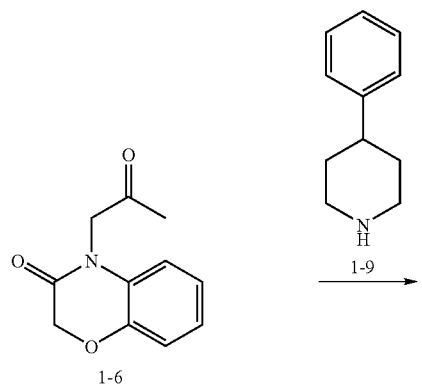

Synthesis of 4-[2-(4-phenyl-piperidin-1-yl)-propyl]-4H-benzo[1,4]oxazin-3-one (Compound 116). A 100 mL flask was equipped with a magnetic stirring bar. The flask was purged with N$_2$ and charged with ketone Compound 1-6 (0.45 g, 2.2 mmol), 4-phenylpiperidine Compound 1-9 (0.39 g, 2.4 mmol) and titanium (IV) isopropoxide (2.83 g, 10 mmol). The mixture was heated in an oil bath at 50° C. for 1.5 hrs, when the reaction was judged complete by TLC. The reaction mixture was cooled to rt and a suspension of sodium borohydride (0.52 g, 14 mmol) in absolute ethanol (10 mL) was carefully added to the reaction mixture, which was diluted with absolute ethanol (18 mL). After stirring for 15 hrs, 1N sodium hydroxide solution (28 mL) was added and a large amount of white solid was formed. It was diluted with H$_2$O (10 mL) and stirred vigorously with CH$_2$Cl$_2$ (50 mL). The suspension was filtered through a Celite® pad (15 g), which was washed with dichloromethane (3×20 mL). The filtrate was transferred to a separatory funnel. The organic phase was separated and the aqueous phase was extracted with methylene chloride (2×40 mL). The organic extracts were combined, dried (Na$_2$SO$_4$), concentrated, and purified by chromatographed on flash silica gel (50 g, elution with 20% EtOAc in hexanes, 1000 mL). The eluent was collected in 50 mL fractions. Fractions 7-11 were combined and concentrated to give Compound 116 as a colorless oil (0.30 g, 39%). R$_f$=0.49 (30% EtOAc/Hexanes); $^1$H NMR (300 MHz, CDCl$_3$) δ 7.32-7.25 (m, 2H), 7.21-7.16 (m, 3H), 7.11-6.99 (m, 4H), 4.66-4.55 (m, 2H), 4.11-3.94 (m, 2H), 3.10-2.97 (m, 2H), 2.78-2.74 (m, 1H), 2.57-2.32 (m, 3H), 1.86-1.59 (m, 4H), 1.02 (d, J=9.2 Hz, 3H); $^{13}$C NMR (75 MHz, CDCl$_3$): 164.8, 146.7, 145.9, 128.9, 128.5, 127.0, 126.2, 123.9, 122.8, 117.3, 115.7, 67.9, 56.7, 52.1, 47.4, 43.8, 43.2, 34.4, 33.8, 11.7.

Example 7

5-chloro-2-{1-[1-methyl-2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide (Compound 84)

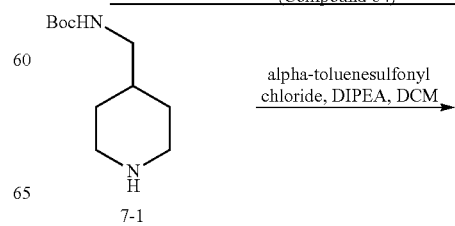

-continued

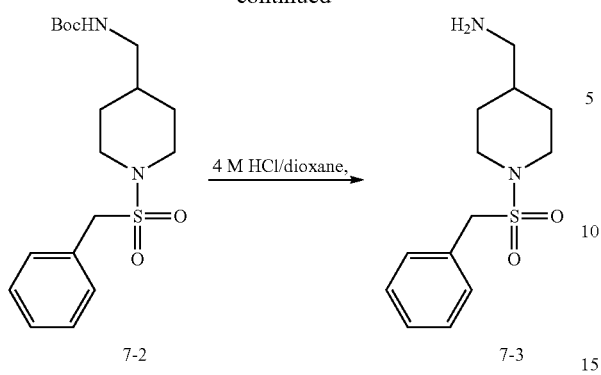

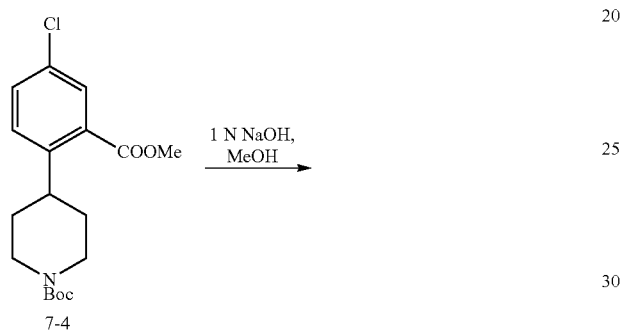

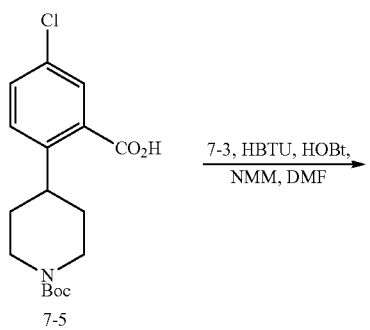

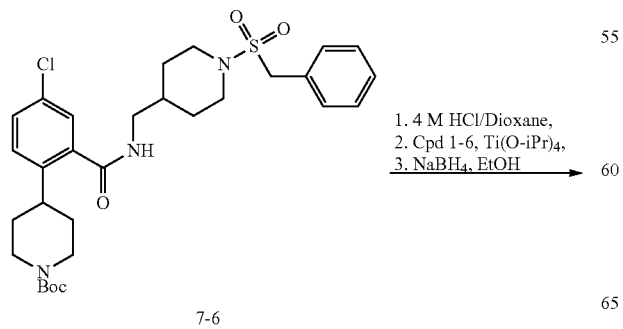

-continued

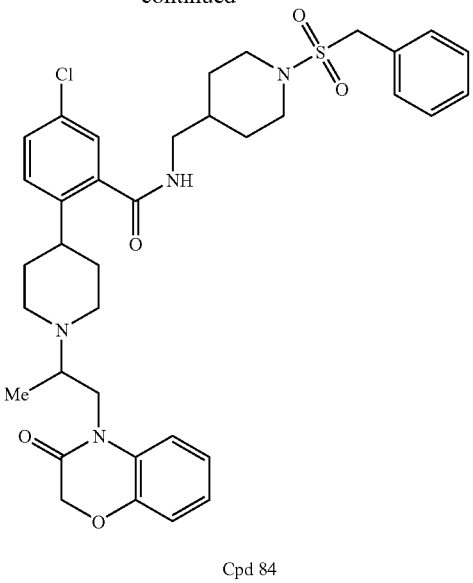

Cpd 84

Step 1. Synthesis of (1-phenylmethanesulfonyl-piperidine-4ylmethyl)-carbamic acid tert-butyl ester (Compound 7-2)

Compound 7-1 (1.00 g, 4.67 mmol) was dissolved in dichloromethane (50 mL) and treated with DIPEA (2.44 mL, 14.0 mmol). The reaction mixture was placed in an ice bath before adding the alpha-toluenesulfonyl chloride (890 mg, 4.67 mmol). The reaction mixture was allowed to warm to rt over a 48 hr period. The reaction was poured into 50 ml of dichloromethane and washed with 1 N hydrochloric acid solution (2×30 mL), 1 N sodium hydroxide solution (2×30 mL), and brine (50 mL). The organic layer was dried over sodium sulfate and concentrated to give Compound 7-2 (1.1 g, 64%) as a white solid. $^1$H NMR (300 MHz, CDCl$_3$) δ 7.38 (m, 5H), 4.60 (bs, NH), 4.20 (s, 2H), 3.65 (d, J=12 Hz, 2H), 2.97 (t, J=6 Hz, 2H), 2.53 (m, 2H), 1.63 (d, J=12 Hz, 2H), 1.43 (m & s, 10H), 1.12 (m, 2H); MS (ES$^+$) m/z 269.1 (M-Boc+1).

Step 2. Synthesis of (1-phenylmethanesulfonyl-piperidin-4-yl)-methylamine hydrochloride (Compound 7-3)

A suspension of Compound 7-2 (142 mg, 0.386 mmol) was stirred in dioxane (2 mL). A solution of 4 M hydrogen chloride in dioxane (1 mL, 4 mmol) was added and stirring continued for 2 hrs before concentrating to a yield Compound 7-3-HCl as a white solid. $^1$H NMR (300 MHz, DMSO d$_6$) δ 7.38 (m, 5H), 4.39 (s, 2H), 3.57 (d, J=12 Hz, 2H), 2.70-2.63 (m, 4H), 1.77-1.60 (m, 3H), 1.12 (m, 2H); MS (ES$^+$) m/z 269.1 (M+1).

Step 3. Synthesis of 4-{4-chloro-2-[(1-phenylmethanesulfonyl-piperidin-4-ylmethyl)-carbamoyl]-phenyl}-piperidine-1-carboxylic acid tert-butyl ester (Compound 7-6)

Compound 7-4 (311 mg, 0.881 mmol) was dissolved in methanol (8 mL) and 1 N sodium hydroxide solution (14 mL) was added. This solution was heated to reflux for 18 hrs, cooled to rt and concentrated to give Compound 7-5 (200 mg, 63%) as the sodium salt. MS (m/z, ES$^+$) 240 (M-Boc+1).

Compound 7-5 (200 mg, 0.55 mmol) was dissolved in dimethylformamide (5 mL) and treated with N-methylmorpholine (194 mL, 1.77 mmol) and HOBt (7 mg, 0.05 mmol). This mixture was chilled to ice bath temperature before adding a mixture of Compound 7-3 (206 mg, 0.77 mmol) and N-methylmorpholine (194 µL, 1.77 mmol) in 5 mL of DMF. Once the solution has equilibrated to ice bath temperature, HBTU (263 mg, 0.696 mmol) was added and stirring was continued in an ice bath for 4 hrs. The reaction mixture was diluted with 50 mL of EtOAc and washed with 1 N sodium hydroxide solution (2×30 mL), 1 N hydrochloric acid solution (2×30 mL), and brine (30 mL). The organic layer was dried over sodium sulfate and concentrated to give Compound 7-6 (0.26 g, 75% crude yield) and was used as is in the next reaction. MS (ES$^+$) m/z 489.9 (M-Boc+1).

Step 4. Synthesis of 5-chloro-2-{1-[1-methyl-2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide (Compound 84)

Compound 7-6 (0.26 g, 0.44 mmol) was dissolved in dioxane (2 mL) and treated with a solution of 4 M hydrogen chloride in dioxane (1 mL, 4 mmol). This solution was stirred at rt for 2 hrs, concentrated, and dissolved in EtOAc (20 mL). The organic layer was washed with 1 N sodium hydroxide (2×10 mL), dried over sodium sulfate, and concentrated to give the piperidine intermediate as a clear oil. Compound 1-6 (182 mg, 0.883 mmol) was combined with the piperidine intermediate and titanium (IV) isopropoxide (1.0 mL, 3.3 mmol) and heated to 50° C. for 1.5 hrs. The reaction mixture was cooled to rt and a slurry of sodium borohydride (171 mg, 4.62 mmol) in absolute ethanol (1 mL) was added. After 15 min additional absolute ethanol (10 mL) was added. After 20 hrs, the reaction mixture was poured into 1 N sodium hydroxide solution (20 mL) and the solids were filtered off. The basic filtrate was diluted with 50 mL of EtOAc and separated. The EtOAc layer was washed with 1 N NaOH (2×20 mL), dried over sodium sulfate and concentrated to a glass like oil. The oil was purified on by reversed phase HPLC (gradient 35-90% acetonitrile in water, both with 0.2% TFA) to give Compound 84 (17.7 mg, 5% over 3 steps). $^1$H NMR (300 MHz, CDCl$_3$) δ 7.46-7.39 (m, 7H), 7.25-7.00 (m, 5H), 6.01 (t, J=7 Hz, NH), 4.62 (m, 2H), 4.6-4.3 (m, 2H), 4.22 (s, 2H), 3.8-2.7 (m, 12H), 2.6-1.2 (m, 8H), 1.34 (d, J=6.7 Hz, 3H); MS (ES$^+$) m/z 679.2 (M+1).

BIOLOGICAL EXAMPLES

Example 1

Calcium Flux Assay

A calcium mobilization assay based on a Fluorescence Imaging Plate Reader (FLIPR, Molecular Devices, Sunnyvale, Calif.) was used to determine antagonist activity, after a 5 min incubation, in response to the agonist cyclic peptide (Ac)-CFWK(2-NaI)C—NH$_2$ (FLIPR EC$_{50}$=0.54±0.2 nM, rU-II Ki=0.12±0.05 nM) at 1 nM (W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, *Angew. Chem., Intl. Ed.* 2002, 41, 2940-2944), in CHO cells transfected with rat GPR14 (U-II receptor) (M. Tal, D. A. Ammar, M. Karpuj, V. Krizhanovsky, M. Naim, D. A. Thompson, *Biochem. Biophys. Res. Commun.* 1995, 209, 752-759. A. Marchese, M. Heiber, T. Nguyen, H. H. Heng, V. R. Saldivia, R. Cheng, P. M. Murphy, L. C. Tsui, X. Shi, P. Gregor, *Genomics* 1995, 29, 335-344).

To derive these cells, the complete coding sequence of rat U-II (Genbank Accession No. U32673) was amplified by nested PCR from rat heart marathon-Ready cDNA. PCR was carried out by using the DNA polymerase PFU (Stratagene) following conditions suggested by the manufacturer. The PCR products were cloned into pcDNA3 (Invitrogen) digested with EcoR I and Xba I. Clones containing rat U-II receptor were verified by complete sequencing of the U-II receptor insert to ensure a lack of PCR-introduced errors. The constructed vector was transfected into CHO cells by using lipofectamine (GIBCO BRL). CHO cells with high expression of rat U-II receptor were selected and established as stable cell lines by using G418. CHO cells were seeded at 25,000 cells per well into 96-well, black-wall, clear-bottom microtiter plates 24 hrs before assay. Cells in culture media (DMEM/F12 containing 15 mM HEPES, L-glutamine, pyridoxine hydrochloride; 10% fetal bovine serum; 1 mg/mL G418 sulfate; antibiotic-antimycotic; pH 7.4) were loaded with proprietary dye, from the FLIPR Calcium Assay Kit (Molecular Devices), prepared in assay buffer (Hanks Balanced Salts Solution, 20 mM HEPES, 0.1% BSA, 2.5 mM probenecid, pH 7.4), and incubated for 1 hr at 37° C. Calcium mobilization determinations were performed at room temperature (23° C.). The use of rat GPR14 was considered acceptable, because human U-II has similar affinity for human or rat GPR14 in the transfected cells (S. A. Douglas, E. H. Ohlstein, *Trends Cardiovasc. Med.* 2000, 10, 229-237). The resulting data is shown in Table 3.

Example 2

Human Radioligand Binding Assay

Human Skeletal Muscle Myoblasts (HSMM) were obtained from Cambrex, and were cultured according to manufacturer's instruction. Cell viability was examined by trypan blue exclusion. Cells at less than 4 passages were used in all studies. For the ($^{125}$I)-U-II binding experiments (Described in: "Characterization of Functional Urotensin II Receptors in Human Skeletal Muscle Myoblasts: Comparison with Angiotensin II Receptors" J. Qi, L. K. Minor, C. Smith, B, Hu, J. Yang, P. Adrade-Gordon, B. Damiano, *Peptides* 2005, 26, 683-690), HSMM were plated in 12-well Costar plates in complete medium for 48 hrs to reach 70% confluence. The binding medium used was Dulbecco's modified Eagle's medium (DMEM) containing 2 mg/ml BSA and 25 mM HEPES (pH 7.4). The cells were washed at room temperature 2× with the binding medium, and were incubated with 0.2 ml per well of prepared binding medium containing 0.150 nM ($^{125}$I)-U-II and compounds for 3 hrs. The cells were washed 4× with the binding medium and solubilized in 1% SDS and 0.5 N NaOH. Radioactivity was quantified by gamma counting.

Radiolabeled ($^{125}$I)-U-II bound specifically and saturably to intact adherent HSMM. The binding assays were performed at 25° C. to lower nonspecific uptake of ($^{125}$I)-U-II by the cells that is seen at 37° C. Using this method, the nonspecific binding was below 10% of total binding. Analysis of the saturation data using the non-linear curve-fitting technique of GraphPad Prism Version 3.0 revealed that the best fit observed was for a one-site model. The derived Kd value was 0.309±0.022 nM (N=3 experiments) with the Hill slope close to unity. Based on the number of cells in a well and Bmax value, the number of UT receptors in HSMM was 2311±236 per cell (N=3 experiments). A time course experiment demonstrated that ($^{125}$I)-U-II binding to HSMM reached steady state at 3 hrs, and remained constant up to 5 hr, the longest time point measured. Human U-II, when add at time 0, efficiently displaced specific binding of ($^{125}$I)-U-II with a Ki of 0.425±0.096 nM (N=3 experiments). The resulting data is shown in Table 4.

TABLE 3

In Vitro Evaluation Rat UII receptors using FLIPR*

| Cpd | IC$_{50}$ (µM) |
|---|---|
| 1 | 7.5 |
| 2 | 7.9 |
| 3 | 4.2 |
| 4 | 3.1 |
| 5 | 11 |
| 6 | 10 |
| 7 | 19 |
| 8 | 14 |
| 9 | 3.2 |
| 10 | 13 |
| 11 | 5.4 |
| 12 | 10 |
| 13 | 8.0 |
| 14 | 4.0 |
| 15 | 8.0 |
| 16 | 8.0 |
| 17 | 7.0 |
| 18 | 15 |
| 19 | 6.0 |
| 20 | 2.0 |
| 21 | 9.0 |
| 22 | 13 |
| 23 | 7.0 |
| 24 | 12 |
| 25 | 4.0 |
| 26 | 2.0 |
| 27 | 43 |
| 28 | 9.0 |
| 29 | 20 |
| 30 | 32 |
| 31 | 13 |
| 32 | 14 |
| 33 | 4.0 |
| 34 | 3.0 |
| 35 | 3.0 |
| 36 | 25 |
| 37 | 30 |
| 38 | 23 |
| 39 | 32 |
| 40 | 4.0 |
| 41 | 21 |
| 42 | 20 |
| 43 | 18 |
| 44 | 21 |
| 45 | 16 |
| 46 | 6.0 |
| 47 | 7.0 |
| 48 | 43 |
| 49 | 38 |
| 50 | 2.5 |
| 51 | 22 |
| 52 | 16 |
| 53 | 18 |
| 54 | 7.0 |
| 55 | 2.0 |
| 56 | 8.0 |
| 57 | 1.3 |
| 58 | 0.60 |
| 59 | 10 |
| 60 | 0.50 |
| 61 | 2.0 |
| 62 | 0.90 |
| 63 | 0.40 |
| 64 | 0.52 |
| 65 | 0.33 |
| 66 | 0.015 |
| 67 | 0.21 |
| 68 | 0.10 |
| 69 | 0.15 |
| 70 | 0.032 |
| 71 | 0.27 |
| 72 | 0.053 |
| 73 | 1.9 |
| 74 | 0.045 |
| 75 | 0.040 |
| 76 | 0.15 |
| 77 | 0.027 |
| 78 | 0.10 |
| 79 | 0.037 |
| 80 | 0.21 |
| 81 | 0.53 |
| 82 | 0.17 |
| 83 | 0.36 |
| 84 | 2.0 |
| 85 | 18 |
| 86 | 24 |
| 87 | 47 |
| 88 | 28 |
| 89 | 23 |
| 90 | 15 |
| 91 | 21 |
| 92 | 20 |
| 93 | 32 |
| 94 | 0.29 |
| 95 | 0.64 |
| 96 | 3.5 |
| 97 | 5.4 |
| 98 | 1.6 |
| 99 | 1.1 |
| 100 | 0.45 |
| 101 | 19 |
| 102 | 7.6 |
| 103 | 24 |
| 104 | 26 |
| 105 | 7.0 |
| 106 | 14 |
| 107 | 9.1 |
| 108 | 8.8 |
| 109 | 5.0 |
| 110 | 11 |
| 111 | 8.0 |
| 112 | 5.0 |
| 113 | 4.4 |
|  | 7.0 |
|  | 21 |
|  | 70 |

*Inhibition of acetyl-cyclic[Cys-Phe-Trp-Lys-(2-Nal)-Cys]-NH$_2$ induced Ca2+ mobilization (FLIPR) in CHO cells transfected with rat UII receptor referenced in: "Structure-Function Analysis of Urotensin II and Its Use in the Construction of a Ligand-Receptor Working Model" W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, Angewandte Chemie, Int. Ed. 2002, 41, 2940-2944.

TABLE 4

In Vitro Evaluation Human UII receptors Binding*

| Cpd | Ki (µM) |
|---|---|
| 1 | 2.9 |
| 3 | 0.33 |
| 20 | 0.72 |
| 26 | 0.75 |
| 34 | 0.62 |
| 35 | 0.59 |
| 50 | 0.43 |
| 55 | 0.84 |
| 57 | 0.19 |
| 58 | 0.14 |
| 60 | 0.15 |
| 61 | 0.26 |

TABLE 4-continued

In Vitro Evaluation Human UII receptors Binding*

| Cpd | Ki (μM) |
|---|---|
| 63 | 0.054 |
| 65 | 0.032 |
| 66 | 0.057 |
| 67 | 0.030 |
| 68 | 0.047 |
| 69 | 0.062 |
| 70 | 0.025 |
| 72 | 0.030 |
| 74 | 0.10 |
| 75 | 0.034 |
| 76 | 0.043 |
| 77 | 0.037 |
| 78 | 0.040 |
| 79 | 0.053 |
| 82 | 0.12 |
| 83 | 0.22 |
| 84 | 0.21 |
| 94 | 1.9 |
| 95 | 1.3 |
| 98 | 1.4 |
| 99 | 1.4 |
| 100 | 1.2 |
| 113 | 1.7 |

*The ($^{125}$I)-U-II binding experiments are described in: "Characterization of Functional Urotensin II Receptors in Human Skeletal Muscle Myoblasts: Comparison with Angiotensin II Receptors" J. Qi, L. K. Minor, C. Smith, B, Hu, J. Yang, P. Adrade-Gordon, B. Damiano, Peptides 2005, 26, 683-690.

While foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

What is claimed is:
1. A compound of Formula (I):

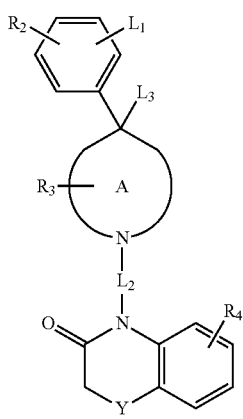

wherein
Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;
Y is selected from the group consisting of $CH_2$, O and S;
$L_1$ is absent or is selected from the group consisting of —C(O)O—$R_1$, —C(O)N($R_5$)—$R_1$ and —NHC(O)—$R_1$;
$L_2$ is $C_{1-8}$alkyl;
$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl,
wherein $C_{1-8}$alkyl is optionally substituted with one, two or three substituents each selected from the group consisting of $C_{1-8}$alkoxy, halogen, hydroxy and —NHR$_6$,
wherein $C_{1-8}$alkoxy is optionally substituted with one, two or three substituents each selected from the group consisting of $C_{1-8}$alkoxy, halogen, hydroxy and —NHR$_6$,
wherein each instance of aryl is optionally substituted with one, two or three substituents each selected from the group consisting of $C_{1-8}$alkyl, $C_{1-8}$alkoxy, halogen and halo-$C_{1-8}$alkyl, and
wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;
$R_2$ is one, two or three substituents each selected from the group consisting of hydrogen, $C_{1-8}$alkyl, $C_{1-8}$alkoxy and halogen;
$R_3$ is one, two or three substituents each selected from the group consisting of hydrogen and $C_{1-4}$alkyl;
$R_4$ is one, two or three substituents each selected from the group consisting of hydrogen, $C_{1-8}$alkyl, $C_{1-8}$alkoxy, hydroxy and halogen;
$R_5$ is selected from the group consisting of hydrogen and $C_{1-4}$alkyl;
$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and,
$R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl,
and pharmaceutically acceptable salts, stereoisomers, tautomers, and esters thereof.

2. The compound of claim 1, wherein Ring A is piperidinyl.
3. The compound of claim 1, wherein Ring A is 8-azabicyclo[3.2.1]oct-2-enyl.
4. The compound of claim 1, wherein Ring A is 8-azabicyclo[3.2.1]octyl.
5. The compound of claim 1, wherein Ring A is 1,2,3,6-tetrahydro-pyridinyl.
6. The compound of claim 1, wherein Y is $CH_2$.
7. The compound of claim 1, wherein Y is O.
8. The compound of claim 1, wherein Y is S.
9. The compound of claim 1, wherein $R_1$ is selected from the group consisting of $C_{1-8}$alkyl, $C_{1-8}$alkoxy, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl and heteroaryl-$C_{1-8}$alkyl,
wherein $C_{1-8}$alkyl is optionally substituted with a substituent selected from the group consisting of $C_{1-8}$alkoxy, hydroxy and —NHR$_6$,
wherein $C_{1-8}$alkoxy is optionally substituted with —NHR$_6$,
wherein each instance of aryl is optionally substituted with one, two or three substituents each selected from the group consisting of $C_{1-8}$alkoxy, halogen and halo-$C_{1-8}$alkyl, and
wherein each instance of heterocyclyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl.

10. The compound of claim 9, wherein $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl,
- wherein each instance of phenyl is optionally substituted with one, two or three substituents each selected from the group consisting of $C_{1-8}$alkoxy, chloro, fluoro, bromo and halo-$C_{1-8}$alkyl, and
- wherein each instance of 1,2,3,4-tetrahydro-isoquinolinyl, pyrrolidinyl-$C_{1-8}$alkyl, piperidinyl-$C_{1-8}$alkyl, and piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl.

11. The compound of claim 1, wherein $R_2$ is one substituent selected from the group consisting of hydrogen, $C_{1-8}$alkyl, $C_{1-8}$alkoxy and halogen.

12. The compound of claim 1, wherein $R_3$ is one or two substituents each selected from the group consisting of hydrogen and $C_{1-4}$alkyl.

13. The compound of claim 1, wherein $R_4$ is one substituent selected from the group consisting of hydrogen, $C_{1-8}$alkyl and halogen.

14. The compound of claim 1, wherein $R_5$ is hydrogen.

15. The compound of claim 1, wherein $R_5$ is $C_{1-4}$alkyl.

16. The compound of claim 1, wherein $R_6$ is selected from the group consisting of $C_{1-8}$alkyl-carbonyl, $C_{1-8}$alkoxy-carbonyl, $C_{1-8}$alkyl-N($R_5$)-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl.

17. The compound of claim 1, wherein $R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl.

18. The compound of claim 1, wherein $R_7$ is selected from the group consisting of $C_{1-8}$alkyl and aryl-$C_{1-8}$alkyl.

19. The compound of claim 1, wherein $R_7$ is selected from the group consisting of $C_{1-8}$alkyl and phenyl-$C_{1-8}$alkyl.

20. The compound of claim 1, wherein
- Ring A is selected from the group consisting of piperidinyl, 8-aza-bicyclo[3.2.1]oct-2-enyl, 8-aza-bicyclo[3.2.1]octyl and 1,2,3,6-tetrahydro-pyridinyl;
- $R_1$ is selected from the group consisting of $C_{1-8}$alkyl, $C_{1-8}$alkoxy, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl and heteroaryl-$C_{1-8}$alkyl,
- wherein $C_{1-8}$alkyl is optionally substituted with a substituent selected from the group consisting of $C_{1-8}$alkoxy, hydroxy and —$NR_6$,
- wherein $C_{1-8}$alkoxy is optionally substituted with —$NHR_6$,
- wherein each instance of aryl is optionally substituted with one, two or three substituents each selected from the group consisting of $C_{1-8}$alkoxy, halogen and halo-$C_{1-8}$alkyl, and
- wherein each instance of heterocyclyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;
- $R_2$ is one substituent selected from the group consisting of hydrogen, $C_{1-8}$alkyl, $C_{1-8}$alkoxy and halogen;
- $R_3$ is one or two substituents each selected from the group consisting of hydrogen and $C_{1-4}$alkyl;
- $R_4$ is one substituent selected from the group consisting of hydrogen, $C_{1-8}$alkyl and halogen;
- $R_6$ is selected from the group consisting of $C_{1-8}$alkyl-carbonyl, $C_{1-8}$alkoxy-carbonyl, $C_{1-8}$alkyl-N($R_5$)-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and
- $R_7$ is selected from the group consisting of $C_{1-8}$alkyl and aryl-$C_{1-8}$alkyl.

21. The compound of claim 20, wherein
- $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl,
- wherein each instance of phenyl is optionally substituted with one, two or three substituents each selected from the group consisting of $C_{1-8}$alkoxy, chloro, fluoro, bromo and halo-$C_{1-8}$alkyl, and
- wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;
- $R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and
- $R_7$ is selected from the group consisting of $C_{1-8}$alkyl and phenyl-$C_{1-8}$alkyl.

22. A compound of Formula (Ia):

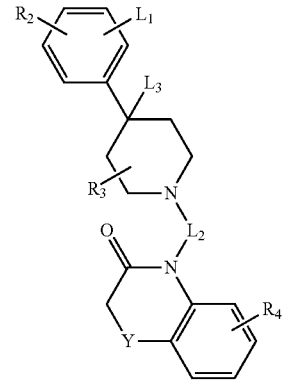

wherein
- Y is selected from the group consisting of $CH_2$, O and S;
- $L_1$ is absent or is selected from the group consisting of —C(O)O—$R_1$, —C(O)N($R_5$)—$R_1$ and —NHC(O)—$R_1$;
- $L_2$ is $C_{1-8}$alkyl;
- $L_3$ is absent or is —C(O)N($R_5$)—$R_7$;
- $R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl,
- wherein $C_{1-8}$alkyl is optionally substituted with one, two or three substituents each selected from the group consisting of $C_{1-8}$alkoxy, halogen, hydroxy and —$NHR_6$, wherein $C_{1-8}$alkoxy is optionally substituted with one, two or three substituents each selected from the group consisting of $C_{1-8}$alkoxy, halogen, hydroxy and —NHR$_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N(R$_5$)-carbonyl, aryl-carbonyl, aryl-$C_{1-8}$alkyl-carbonyl, aryl-$C_{1-8}$alkoxy-carbonyl, aryl-N(R$_5$)-carbonyl, aryl-$C_{1-8}$alkyl-N(R$_5$)-carbonyl or aryl-$C_{1-8}$alkyl-sulfonyl;

R$_2$ is one, two or three substituents each selected from the group consisting of hydrogen, $C_{1-8}$alkyl, $C_{1-8}$alkoxy and halogen;

R$_3$ is one, two or three substituents each selected from the group consisting of hydrogen and $C_{1-4}$alkyl;

R$_4$ is one, two or three substituents each selected from the group consisting of hydrogen, $C_{1-8}$alkyl, $C_{1-8}$alkoxy, hydroxy and halogen;

R$_5$ is selected from the group consisting of hydrogen and $C_{1-4}$alkyl;

R$_6$ is selected from the group consisting of $C_{1-8}$alkyl-carbonyl, $C_{1-8}$alkoxy-carbonyl, $C_{1-8}$alkyl-N(R$_5$)-carbonyl, aryl-carbonyl, aryl-$C_{1-8}$alkyl-carbonyl, aryl-$C_{1-8}$alkoxy-carbonyl, aryl-N(R$_5$)-carbonyl, aryl-$C_{1-8}$alkyl-N(R$_5$)-carbonyl and aryl-$C_{1-8}$alkyl-sulfonyl; and, R$_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, and pharmaceutically acceptable salts, stereoisomers, tautomers, and esters thereof.

23. The compound of claim 22, wherein
R$_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —NR$_6$, wherein $C_{1-8}$alkoxy is optionally substituted with —NHR$_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N(R$_5$)-carbonyl or aryl-$C_{1-8}$alkyl-sulfonyl;

R$_2$ is one substituent selected from the group consisting of hydrogen, $C_{1-8}$alkyl, $C_{1-8}$alkoxy and halogen;

R$_3$ is one or two substituents each selected from the group consisting of hydrogen and $C_{1-4}$alkyl;

R$_4$ is one substituent selected from the group consisting of hydrogen, $C_{1-8}$alkyl and halogen;

R$_5$ is selected from the group consisting of hydrogen and $C_{1-4}$alkyl;

R$_6$ is selected from the group consisting of $C_{1-8}$alkyl-carbonyl, $C_{1-8}$alkoxy-carbonyl, $C_{1-8}$alkyl-N(R$_5$)-carbonyl, phenyl-$C_{1-8}$alkoxy-carbonyl, phenyl-N(R$_5$)-carbonyl, phenyl-$C_{1-8}$alkyl-N(R$_5$)-carbonyl and phenyl-$C_{1-8}$alkyl-sulfonyl; and R$_7$ is selected from the group consisting of $C_{1-8}$alkyl and phenyl-$C_{1-8}$alkyl.

24. A compound of Formula (Ib):

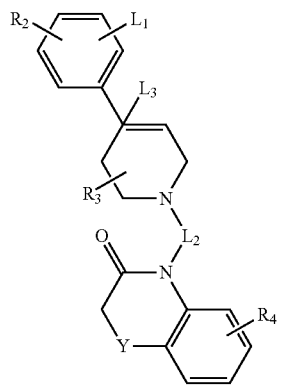

wherein
Y is selected from the group consisting of $CH_2$, O and S;
L$_1$ is absent or is selected from the group consisting of —C(O)O—R$_1$, —C(O)N(R$_5$)—R$_1$ and —NHC(O)—R$_1$;
L$_2$ is $C_{1-8}$alkyl;
L$_3$ is absent;
R$_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —NHR$_6$, wherein $C_{1-8}$alkoxy is optionally substituted with one, two or three substituents each selected from the group consisting of $C_{1-8}$alkoxy, halogen, hydroxy and —NHR$_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N(R$_5$)-carbonyl, aryl-carbonyl, aryl-$C_{1-8}$alkyl-carbonyl, aryl-$C_{1-8}$alkoxy-carbonyl, aryl-N(R$_5$)-carbonyl, aryl-$C_{1-8}$alkyl-N(R$_5$)-carbonyl or aryl-$C_{1-8}$alkyl-sulfonyl;

R$_2$ is one, two or three substituents each selected from the group consisting of hydrogen, $C_{1-8}$alkyl, $C_{1-8}$alkoxy and halogen;

R$_3$ is one, two or three substituents each selected from the group consisting of hydrogen and $C_{1-4}$alkyl;

R$_4$ is one, two or three substituents each selected from the group consisting of hydrogen, $C_{1-8}$alkyl, $C_{1-8}$alkoxy, hydroxy and halogen;

R$_5$ is selected from the group consisting of hydrogen and $C_{1-4}$alkyl;

R$_6$ is selected from the group consisting of $C_{1-8}$alkyl-carbonyl, $C_{1-8}$alkoxy-carbonyl, $C_{1-8}$alkyl-N(R$_5$)-carbonyl, aryl-carbonyl, aryl-$C_{1-8}$alkyl-carbonyl, aryl- $C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, and pharmaceutically acceptable salts, stereoisomers, tautomers, and esters thereof.

25. The compound of claim 24, wherein $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

26. A compound of Formula (Ic):

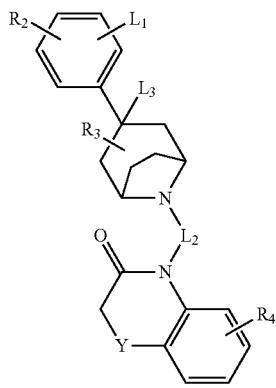

wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent or is —C(O)N($R_5$)—$R_7$;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —$NHR_6$, wherein $C_{1-8}$alkoxy is optionally substituted with one, two or three substituents each selected from the group consisting of $C_{1-8}$alkoxy, halogen, hydroxy and —$NHR_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, and pharmaceutically acceptable salts, stereoisomers, tautomers, and esters thereof.

27. The compound of claim 26, wherein $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —$NR_6$, wherein $C_{1-8}$alkoxy is optionally substituted with —$NHR_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

28. A compound of Formula (Id):

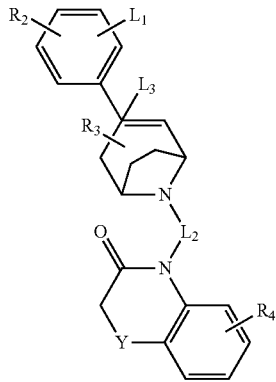

wherein

Y is selected from the group consisting of $CH_2$, O and S;

$L_1$ is absent or is selected from the group consisting of —C(O)O—$R_1$, —C(O)N($R_5$)—$R_1$ and —NHC(O)—$R_1$;

$L_2$ is $C_{1-8}$alkyl;

$L_3$ is absent;

$R_1$ is selected from the group consisting of $C_{1-8}$alkyl, $C_{1-8}$alkoxy, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, wherein $C_{1-8}$alkyl is optionally substituted with one, two or three substituents each selected from the group consisting of $C_{1-8}$alkoxy, halogen, hydroxy and —NHR$_6$, wherein $C_{1-8}$alkoxy is optionally substituted with one, two or three substituents each selected from the group consisting of $C_{1-8}$alkoxy, halogen, hydroxy and —NHR$_6$, wherein each instance of aryl is optionally substituted with one, two or three substituents each selected from the group consisting of $C_{1-8}$alkyl, $C_{1-8}$alkoxy, halogen and halo-$C_{1-8}$alkyl, and wherein each instance of heterocyclyl is optionally substituted with oxo, $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl or aryl-$C_{1-8}$alkyl-sulfonyl;

$R_2$ is one, two or three substituents each selected from the group consisting of hydrogen, $C_{1-8}$alkyl, $C_{1-8}$alkoxy and halogen;

$R_3$ is one, two or three substituents each selected from the group consisting of hydrogen and $C_{1-4}$alkyl;

$R_4$ is one, two or three substituents each selected from the group consisting of hydrogen, $C_{1-8}$alkyl, $C_{1-8}$alkoxy, hydroxy and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, aryl-carbonyl, aryl-$C_{1-8}$alkyl-carbonyl, aryl-$C_{1-8}$alkoxy-carbonyl, aryl-N($R_5$)-carbonyl, aryl-$C_{1-8}$alkyl-N($R_5$)-carbonyl and aryl-$C_{1-8}$alkyl-sulfonyl; and, $R_7$ is selected from the group consisting of $C_{1-8}$alkyl, aryl, aryl-$C_{1-8}$alkyl, $C_{3-14}$cycloalkyl, $C_{3-14}$cycloalkyl-$C_{1-8}$alkyl, heterocyclyl, heterocyclyl-$C_{1-8}$alkyl, heteroaryl and heteroaryl-$C_{1-8}$alkyl, and pharmaceutically acceptable salts, stereoisomers, tautomers, and esters thereof.

29. The compound of claim 28, wherein $R_1$ is selected from the group consisting of $C_{1-8}$alkyl, $C_{1-8}$alkoxy, phenyl-$C_{1-8}$alkyl, naphthyl-$C_{1-8}$alkyl, indanyl, cyclopropyl-$C_{1-8}$alkyl, cyclohexyl-$C_{1-8}$alkyl, 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl, furanyl-$C_{1-8}$alkyl, thienyl-$C_{1-8}$alkyl, imidazolyl-$C_{1-8}$alkyl, pyridinyl-$C_{1-8}$alkyl and indolyl-$C_{1-8}$alkyl, wherein $C_{1-8}$alkyl is optionally substituted with a substituent selected from the group consisting of $C_{1-8}$alkoxy, hydroxy and —NR$_6$, wherein $C_{1-8}$alkoxy is optionally substituted with —NHR$_6$, wherein each instance of phenyl is optionally substituted with one, two or three substituents each selected from the group consisting of $C_{1-8}$alkoxy, chloro, fluoro, bromo and halo-$C_{1-8}$alkyl, and wherein each instance of 1,2,3,4-tetrahydro-isoquinolinyl, pyrrolidinyl-$C_{1-8}$alkyl, piperidinyl-$C_{1-8}$alkyl, piperazinyl-$C_{1-8}$alkyl is optionally substituted with oxo, $C_{1-8}$alkyl-carbonyl, $C_{1-8}$alkoxy-carbonyl, aryl-carbonyl, aryl-$C_{1-8}$alkoxy-carbonyl, aryl-$C_{1-8}$alkyl-N($R_5$)-carbonyl or aryl-$C_{1-8}$alkyl-sulfonyl;

$R_2$ is one substituent selected from the group consisting of hydrogen, $C_{1-8}$alkyl, $C_{1-8}$alkoxy and halogen;

$R_3$ is one or two substituents each selected from the group consisting of hydrogen and $C_{1-4}$alkyl;

$R_4$ is one substituent selected from the group consisting of hydrogen, $C_{1-8}$alkyl and halogen;

$R_5$ is selected from the group consisting of hydrogen and $C_{1-4}$alkyl;

$R_6$ is selected from the group consisting of $C_{1-8}$alkyl-carbonyl, $C_{1-8}$alkoxy-carbonyl, $C_{1-8}$alkyl-N($R_5$)-carbonyl, phenyl-$C_{1-8}$alkoxy-carbonyl, phenyl-N($R_5$)-carbonyl, phenyl-$C_{1-8}$alkyl-N($R_5$)-carbonyl and phenyl-$C_{1-8}$alkyl-sulfonyl; and $R_7$ is selected from the group consisting of $C_{1-8}$alkyl and phenyl-$C_{1-8}$alkyl.

30. A compound selected from the group consisting of:

2-{1-[2-(3-oxo-2,3-dihydro-benzo[1,4]oxazin-4-yl)-ethyl]-piperidin-4-yl}-N-phenethyl-benzamide, N-benzyl-2-{1-[2-(3-oxo-2,3-dihydro-benzo[1,4]oxazin-4-yl)-ethyl]-piperidin-4-yl}-benzamide, 2-{1-[2-(3-oxo-2,3-dihydro-benzo[1,4]oxazin-4-yl)-ethyl-piperidin-4-yl}-N-(3-phenyl-propyl)-benzamide, 2-{1-[2-(3-oxo-2,3-dihydro-benzo[1,4]oxazin-4-yl)-ethyl]-piperidin-4-yl}-N-(4-phenyl-butyl)-benzamide, N-benzyl-N-methyl-2-{1-[2-(3-oxo-2,3-dihydro-benzo[1,4]oxazin-4-yl)-ethyl]-piperidin-4-yl}-benzamide, N-[2-(3-methoxy-phenyl)-ethyl]-2-{1-[2-(3-oxo-2,3-di-hydro-benzo[1,4]oxazin-4-yl)-ethyl]-piperidin-4-yl}-benzamide,
N-[2-(2,4-dichloro-phenyl)-ethyl]-2-{1-[2-(3-oxo-2,3-di-hydro-benzo[1,4]oxazin-4-yl)-ethyl]-piperidin-4-yl}-benzamide,
N-[2-(2-chloro-phenyl)-ethyl]-2-{1-[2-(3-oxo-2,3-dihy-dro-benzo[1,4]oxazin-4-yl)-ethyl]-piperidin-4-yl}-benzamide,
N-[2-(4-chloro-phenyl)-ethyl]-2-{1-[2-(3-oxo-2,3-dihy-dro-benzo[1,4]oxazin-4-yl)-ethyl]-piperidin-4-yl}-benzamide,
N-[2-(3,4-dimethoxy-phenyl)-ethyl]-2-{1-[2-(3-oxo-2,3-dihydro-benzo[1,4]oxazin-4-yl)-ethyl]-piperidin-4-yl}-benzamide,
N-[2-(3,4-dichloro-phenyl)-ethyl]-2-{1-[2-(3-oxo-2,3-di-hydro-benzo[1,4]oxazin-4-yl)-ethyl]-piperidin-4-yl}-benzamide,
N-[2-(4-chloro-phenyl)-1-methyl-ethyl]-2-{1-[2-(3-oxo-2,3-dihydro-benzo[1,4]oxazin-4-yl)-ethyl]-piperidin-4-yl}-benzamide,
N-[2-(2,5-dimethoxy-phenyl)-ethyl]-2-{1-[2-(3-oxo-2,3-dihydro-benzo[1,4]oxazin-4-yl)-ethyl]-piperidin-4-yl}-benzamide,
N-[2-(4-methoxy-phenyl)-ethyl]-2-{1-[2-(3-oxo-2,3-di-hydro-benzo[1,4]oxazin-4-yl)-ethyl]-piperidin-4-yl}-benzamide,
N-[2-(2-methoxy-phenyl)-ethyl]-2-{1-[2-(3-oxo-2,3-di-hydro-benzo[1,4]oxazin-4-yl)-ethyl]-piperidin-4-yl}-benzamide,
N-[2-(4-fluoro-phenyl)-ethyl]-2-{1-[2-(3-oxo-2,3-dihy-dro-benzo[1,4]oxazin-4-yl)-ethyl]-piperidin-4-yl}-benzamide,
N-[2-(3,5-dimethoxy-phenyl)-ethyl]-2-{1-[2-(3-oxo-2,3-dihydro-benzo[1,4]oxazin-4-yl)-ethyl]-piperidin-4-yl}-benzamide,
N-methyl-2-{1-[2-(3-oxo-2,3-dihydro-benzo[1,4]oxazin-4-yl)-ethyl]-piperidin-4-yl}-N-phenethyl-benzamide,
N-[2-(3,4-difluoro-phenyl)-ethyl]-2-{1-[2-(3-oxo-2,3-di-hydro-benzo[1,4]oxazin-4-yl)-ethyl]-piperidin-4-yl}-benzamide,
N-(2-naphthalen-2-yl-ethyl)-2-{1-[2-(3-oxo-2,3-dihydro-benzo[1,4]oxazin-4-yl)-ethyl]-piperidin-4-yl}-benzamide,
N-[2-(3,5-difluoro-phenyl)-ethyl]-2-{1-[2-(3-oxo-2,3-di-hydro-benzo[1,4]oxazin-4-yl)-ethyl]-piperidin-4-yl}-benzamide,
N-[2-(2,5-difluoro-phenyl)-ethyl]-2-{1-[2-(3-oxo-2,3-di-hydro-benzo[1,4]oxazin-4-yl)-ethyl]-piperidin-4-yl}-benzamide,
N-[2-(2,3-difluoro-phenyl)-ethyl]-2-{1-[2-(3-oxo-2,3-di-hydro-benzo[1,4]oxazin-4-yl)-ethyl]-piperidin-4-yl}-benzamide,
N-cyclopropylmethyl-2-{1-[2-(3-oxo-2,3-dihydro-benzo[1,4]oxazin-4-yl)-ethyl]-piperidin-4-yl}-benzamide,
N-(1-methyl-3-phenyl-propyl)-2-{1-[2-(3-oxo-2,3-dihy-dro-benzo[1,4]oxazin-4-yl)-ethyl]-piperidin-4-yl}-benzamide,
N-[2-(1H-indol-3-yl)-ethyl]-2-{1-[2-(3-oxo-2,3-dihydro-benzo[1,4]oxazin-4-yl)-ethyl]-piperidin-4-yl}-benzamide,
N-indan-1-yl-2-{1-[2-(3-oxo-2,3-dihydro-benzo[1,4]ox-azin-4-yl)-ethyl]-piperidin-4-yl}-benzamide,
2-{1-[2-(3-oxo-2,3-dihydro-benzo[1,4]oxazin-4-yl)-ethyl]-piperidin-4-yl}-N-(2-phenyl-propyl)-benzamide,
2-{1-[2-(3-oxo-2,3-dihydro-benzo[1,4]oxazin-4-yl)-ethyl]-piperidin-4-yl}-N-propyl-benzamide,
2-{1-[2-(3-oxo-2,3-dihydro-benzo[1,4]oxazin-4-yl)-ethyl]-piperidin-4-yl}-N-(2-pyrrolidin-1-yl-ethyl)-benzamide,
N-cyclohexylmethyl-2-{1-[2-(3-oxo-2,3-dihydro-benzo[1,4]oxazin-4-yl)-ethyl]-piperidin-4-yl}-benzamide,
N-furan-2-ylmethyl-N-methyl-2-{1-[2-(3-oxo-2,3-dihy-dro-benzo[1,4]oxazin-4-yl)-ethyl]-piperidin-4-yl}-benzamide,
N-(2-{1-[2-(3-oxo-2,3-dihydro-benzo[1,4]oxazin-4-yl)-ethyl]-piperidin-4-yl}-phenyl)-3-phenyl-propiona-mide,
[4-(2-{1-[2-(3-oxo-2,3-dihydro-benzo[1,4]oxazin-4-yl)-ethyl]-piperidin-4-yl}-benzoylamino)-butyl]-carbamic acid tert-butyl ester,
N-(2-methoxy-ethyl)-2-{1-[2-(3-oxo-2,3-dihydro-benzo[1,4]oxazin-4-yl)-ethyl]-piperidin-4-yl}-benzamide,
N-(3-methoxy-propyl)-2-{1-[2-(3-oxo-2,3-dihydro-benzo[1,4]oxazin-4-yl)-ethyl]-piperidin-4-yl}-benzamide,
N-(3-ethoxy-propyl)-2-{1-[2-(3-oxo-2,3-dihydro-benzo[1,4]oxazin-4-yl)-ethyl]-piperidin-4-yl}-benzamide,
N-(3-hydroxy-propyl)-2-{1-[2-(3-oxo-2,3-dihydro-benzo[1,4]oxazin-4-yl)-ethyl]-piperidin-4-yl}-benzamide,
2-{1-[2-(3-oxo-2,3-dihydro-benzo[1,4]oxazin-4-yl)-ethyl]-piperidin-4-yl}-N-[2-(4-trifluoromethyl-phe-nyl)-ethyl]-benzamide,
2-{1-[2-(3-oxo-2,3-dihydro-benzo[1,4]oxazin-4-yl)-ethyl]-piperidin-4-yl}-N-pyridin-2-ylmethyl-benza-mide,
2-{1-[2-(3-oxo-2,3-dihydro-benzo[1,4]oxazin-4-yl)-ethyl]-piperidin-4-yl}-N-(2-pyridin-2-yl-ethyl)-benza-mide,
2-{1-[2-(3-oxo-2,3-dihydro-benzo[1,4]oxazin-4-yl)-ethyl]-piperidin-4-yl}-N-pyridin-3-ylmethyl-benza-mide,
2-{1-[2-(3-oxo-2,3-dihydro-benzo[1,4]oxazin-4-yl)-ethyl]-piperidin-4-yl}-N-pyridin-4-ylmethyl-benza-mide,
2-{1-[2-(3-oxo-2,3-dihydro-benzo[1,4]oxazin-4-yl)-ethyl]-piperidin-4-yl}-N-(2-pyridin-4-yl-ethyl)-benza-mide,
2-{1-[2-(3-oxo-2,3-dihydro-benzo[1,4]oxazin-4-yl)-ethyl]-piperidin-4-yl}-N-thiophen-2-ylmethyl-benza-mide,
2-{1-[2-(3-oxo-2,3-dihydro-benzo[1,4]oxazin-4-yl)-ethyl]-piperidin-4-yl}-N-(2-thiophen-2-yl-ethyl)-ben-zamide,
N-(3-imidazol-1-yl-propyl)-2-{1-[2-(3-oxo-2,3-dihydro-benzo[1,4]oxazin-4-yl)-ethyl]-piperidin-4-yl}-benza-mide,
N-(2-acetylamino-ethyl)-2-{1-[2-(3-oxo-2,3-dihydro-benzo[1,4]oxazin-4-yl)-ethyl]-piperidin-4-yl}-benza-mide,
4-[(2-{1-[2-(3-oxo-2,3-dihydro-benzo[1,4]oxazin-4-yl)-ethyl]-piperidin-4-yl}-benzoylamino)-methyl]-piperi-dine-1-carboxylic acid tert-butyl ester,
2-{1-[2-(3-oxo-2,3-dihydro-benzo[1,4]oxazin-4-yl)-ethyl]-piperidin-4-yl}-N-[3-(2-oxo-pyrrolidin-1-yl)-propyl]-benzamide,
2-{1-[2-(3-oxo-2,3-dihydro-benzo[1,4]oxazin-4-yl)-ethyl]-piperidin-4-yl}-N-(2-piperidin-1-yl-ethyl)-ben-zamide,
4-(2-{4-[2-(3,4-dihydro-1H-isoquinoline-2-carbonyl)-phenyl]-piperidin-1-yl}-ethyl)-4H-benzo[1,4]oxazin-3-one, N-[2-(3-naphthalen-2-yl-ureido)-ethyl]-2-{1-[2-(3-oxo-2,3-dihydro-benzo[1,4]oxazin-4-yl)-ethyl]-piperidin-4-yl}-benzamide, N-[2-(3-naphthalen-1-yl-ureido)-ethyl]-2-{1-[2-(3-oxo-2,3-dihydro-benzo[1,4]oxazin-4-yl)-ethyl]-piperidin-4-yl}-benzamide, 5-chloro-2-{1-[2-(3-oxo-2,3-dihydro-benzo[1,4]oxazin-4-yl)-ethyl]-piperidin-4-yl}-benzoic acid methyl ester, 5-chloro-2-{1-[2-(3-oxo-2,3-dihydro-benzo[1,4]oxazin-4-yl)-ethyl]-piperidin-4-yl}-N-phenethyl-benzamide, 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester, 5-chloro-N,N-dimethyl-2-{1-[2-(3-oxo-2,3-dihydro-benzo[1,4]oxazin-4-yl)-ethyl]-piperidin-4-yl}-benzamide,

[4-(5-chloro-2-{1-[2-(3-oxo-2,3-dihydro-benzo[1,4]oxazin-4-yl)-ethyl]-piperidin-4-yl}-benzoylamino)-butyl]-carbamic acid tert-butyl ester, 5-chloro-N-(2-naphthalen-2-yl-ethyl)-2-{1-[2-(3-oxo-2,3-dihydro-benzo[1,4]oxazin-4-yl)-ethyl]-piperidin-4-yl}-benzamide, 5-chloro-N-[2-(1H-indol-3-yl)-ethyl]-2-{1-[2-(3-oxo-2,3-dihydro-benzo[1,4]oxazin-4-yl)-ethyl]-piperidin-4-yl}-benzamide, 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzyl ester, N-(1-benzoyl-piperidin-4-ylmethyl)-5-chloro-2-{1-[2-(3-oxo-2,3-dihydro-benzo[1,4]oxazin-4-yl)-ethyl]-piperidin-4-yl}-benzamide, 5-chloro-N-[1-(3,3-dimethyl-butyryl)-piperidin-4-ylmethyl]-2-{1-[2-(3-oxo-2,3-dihydro-benzo[1,4]oxazin-4-yl)-ethyl]-piperidin-4-yl}-benzamide, 4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester, 4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzylamide, 4-[2-(5-chloro-2-{1-[2-(3-oxo-2,3-dihydro-benzo[1,4]oxazin-4-yl)-ethyl]-piperidin-4-yl}-benzoylamino)-ethyl]-piperidine-1-carboxylic acid tert-butyl ester,

[4-(5-chloro-2-{1-[2-(3-oxo-2,3-dihydro-benzo[1,4]oxazin-4-yl)-ethyl]-piperidin-4-yl}-benzoylamino)-butyl]-carbamic acid benzyl ester,

[5-(5-chloro-2-{1-[2-(3-oxo-2,3-dihydro-benzo[1,4]oxazin-4-yl)-ethyl]-piperidin-4-yl}-benzoylamino)-pentyl]-carbamic acid tert-butyl ester, 5-chloro-2-{1-[2-(3-oxo-2,3-dihydro-benzo[1,4]oxazin-4-yl)-ethyl]-piperidin-4-yl}-N-(2-piperidin-1-yl-ethyl)-benzamide, 5-chloro-2-{1-[2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide, 5-chloro-2-{1-[2-(3-oxo-2,3-dihydro-benzo[1,4]oxazin-4-yl)-ethyl]-piperidin-4-yl}-N-(2-piperazin-1-yl-ethyl)-benzamide,

[6-(5-chloro-2-{1-[2-(3-oxo-2,3-dihydro-benzo[1,4]oxazin-4-yl)-ethyl]-piperidin-4-yl}-benzoylamino)-hexyl]-carbamic acid tert-butyl ester,

[5-(5-chloro-2-{1-[2-(3-oxo-2,3-dihydro-benzo[1,4]oxazin-4-yl)-ethyl]-piperidin-4-yl}-benzoylamino)-pentyl]-carbamic acid benzyl ester, 5-chloro-N-[5-(3,3-dimethyl-butyrylamino)-pentyl]-2-{1-[2-(3-oxo-2,3-dihydro-benzo[1,4]oxazin-4-yl)-ethyl]-piperidin-4-yl}-benzamide, N-[5-(3-benzyl-ureido)-pentyl]-5-chloro-2-{1-[2-(3-oxo-2,3-dihydro-benzo[1,4]oxazin-4-yl)-ethyl]-piperidin-4-yl}-benzamide, 5-chloro-2-{1-[2-(3-oxo-2,3-dihydro-benzo[1,4]oxazin-4-yl)-ethyl]-piperidin-4-yl}-N-(5-phenylmethanesulfonylamino-pentyl)-benzamide, {2-[2-(5-chloro-2-{1-[2-(3-oxo-2,3-dihydro-benzo[1,4]oxazin-4-yl)-ethyl]-piperidin-4-yl}-benzoylamino)-ethoxy]-ethyl}-carbamic acid tert-butyl ester, 5-chloro-N-[5-(3-isopropyl-ureido)-pentyl]-2-{1-[2-(3-oxo-2,3-dihydro-benzo[1,4]oxazin-4-yl)-ethyl]-piperidin-4-yl}-benzamide, 5-chloro-2-{1-[2-(3-oxo-2,3-dihydro-benzo[1,4]oxazin-4-yl)-ethyl]-piperidin-4-yl}-N-[5-(3-phenyl-ureido)-pentyl]-benzamide, 5-chloro-2-{1-[2-(3-oxo-2,3-dihydro-benzo[1,4]oxazin-4-yl)-ethyl]-piperidin-4-yl}-N-[5-(3-phenethyl-ureido)-pentyl]-benzamide,

[5-(5-chloro-2-{1-[2-(2-oxo-3,4-dihydro-2H-quinolin-1-yl)-ethyl]-piperidin-4-yl}-benzoylamino)-pentyl]-carbamic acid tert-butyl ester, 5-chloro-2-{1-[1-methyl-2-(3-oxo-2,3-dihydro-benzo[1,4]oxazin-4-yl)-ethyl]-piperidin-4-yl}-N-(1-phenyl-methanesulfonyl-piperidin-4-ylmethyl)-benzamide, 4-{2-[4-(4-chloro-phenyl)-piperidin-1-yl]-ethyl}-4H-benzo[1,4]oxazin-3-one, 4-[2-(4-phenyl-piperidin-1-yl)-ethyl]-4H-benzo[1,4]oxazin-3-one, 4-{2-[4-(4-methoxy-phenyl)-piperidin-1-yl]-ethyl}-4H-benzo[1,4]oxazin-3-one, 4-{2-[4-(3-fluoro-phenyl)-piperidin-1-yl]-ethyl}-4H-benzo[1,4]oxazin-3-one, 4-{2-[4-(2-fluoro-phenyl)-piperidin-1-yl]-ethyl}-4H-benzo[1,4]oxazin-3-one, 4-[2-(4-p-tolyl-piperidin-1-yl)-ethyl]-4H-benzo[1,4]oxazin-3-one, 4-[2-(4-o-tolyl-piperidin-1-yl)-ethyl]-4H-benzo[1,4]oxazin-3-one, 4-{2-[4-(3-chloro-phenyl)-piperidin-1-yl]-ethyl}-4H-benzo[1,4]oxazin-3-one, 2-{1-[2-(3-oxo-2,3-dihydro-benzol[1,4]oxain-4-yl-ethyl]-piperidine-4-yl-benzoic acid methyl ester, 4-[2-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-ethyl]-piperazine-1-carboxylic acid tert-butyl ester,

[5-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-pentyl]-carbamic acid tert-butyl ester, 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester,

[5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester,

[5-(2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester, 4-[2-(2-{8-[2-(3-oxo-2,3-dihydro-benzo[1,4]oxazin-4-yl)-ethyl]-8-aza-bicyclo[3.2.1]oct-3-yl}-benzoylamino)-ethyl]-piperazine-1-carboxylic acid tert-butyl ester,

[5-(5-chloro-2-{8-[2-(3-oxo-2,3-dihydro-benzo[1,4]oxazin-4-yl)-ethyl]-8-aza-bicyclo[3.2.1]oct-3-yl}-benzoylamino)-pentyl]-carbamic acid tert-butyl ester, 4-[2-(3-phenyl-8-aza-bicyclo[3.2.1]oct-8-yl)-ethyl]-4H-benzo[1,4]oxazin-3-one,
[5-(5-chloro-2-{2,6-dimethyl-1-[2-(3-oxo-2,3-dihydro-benzo[1,4]oxazin-4-yl)-ethyl]-1,2,3,6-tetrahydro-pyridin-4-yl}-benzoylamino)pentyl]-carbamic acid tert-butyl ester,
1-[2-(3-oxo-2,3-dihydro-benzo[1,4]oxazin-4-yl)-ethyl]-4-phenyl-piperidine-4-carboxylic acid dimethyl amide,
1-[2-(3-oxo-2,3-dihydro-benzo[1,4]oxazin-4-yl)-ethyl]-4-phenyl-piperidine-4-carboxylic acid benzylamide,
1-[2-(3-oxo-2,3-dihydro-benzo[1,4]oxazin-4-yl)-ethyl]-4-phenyl-piperidine-4-carboxylic acid phenethyl-amide,
1-[2-(3-oxo-2,3-dihydro-benzo[1,4]oxazin-4-yl)-ethyl]-4-phenyl-piperidine-4-carboxylic acid methyl-phenethyl-amide,
1-[2-(3-oxo-2,3-dihydro-benzo[1,4]oxazin-4-yl)-ethyl]-4-phenyl-piperidine-4-carboxylic acid (3-phenyl-propyl)-amide,
1-[2-(3-oxo-2,3-dihydro-benzo[1,4]oxazin-4-yl)-ethyl]-4-phenyl-piperidine-4-carboxylic acid (4-phenyl-butyl)-amide,
4-(4-chloro-phenyl)-1-[2-(3-oxo-2,3-dihydro-benzo[1,4]oxazin-4-yl)-ethyl]-piperidine-4-carboxylic acid phenethyl-amide,
1-[2-(6-chloro-3-oxo-2,3-dihydro-benzo[1,4]oxazin-4-yl)-ethyl]-4-(4-chloro-phenyl)-piperidine-4-carboxylic acid dimethylamide,
4-(4-chloro-phenyl)-1-[2-(6-methyl-3-oxo-2,3-dihydro-benzo[1,4]oxazin-4-yl)-ethyl]-piperidine-4-carboxylic acid dimethylamide,
4-(4-chloro-phenyl)-1-[2-(6-fluoro-3-oxo-2,3-dihydro-benzo[1,4]oxazin-4-yl)-ethyl]-piperidine-4-carboxylic acid dimethylamide,
4-(4-chloro-phenyl)-1-[2-(3-oxo-2,3-dihydro-benzo[1,4]oxazin-4-yl)-ethyl]-piperidine-4-carboxylic acid dimethylamide,
4-(4-chloro-phenyl)-1-[2-(3-oxo-2,3-dihydro-benzo[1,4]thiazin-4-yl)-ethyl]-piperidine-4-carboxylic acid dimethylamide,
4-(4-chloro-phenyl)-1-[2-(2-oxo-3,4-dihydro-2H-quinolin-1-yl)-ethyl]-piperidine-4-carboxylic acid dimethylamide, and
4-[2-(4-phenyl-piperidin-1-yl)-propyl]-4H-benzo[1,4]oxazin-3-one.

31. The compound of claim 30, wherein the compound is selected from the group consisting of:
2-{1-[2-(3-oxo-2,3-dihydro-benzo[1,4]oxazin-4-yl)-ethyl-piperidin-4-yl]-N-(3-phenyl-propyl)-benzamide,
N-(2-naphthalen-2-yl-ethyl)-2-{1-[2-(3-oxo-2,3-dihydro-benzo[1,4]oxazin-4-yl)-ethyl]-piperidin-4-yl}-benzamide,
N-[2-(1H-indol-3-yl)-ethyl]-2-{1-[2-(3-oxo-2,3-dihydro-benzo[1,4]oxazin-4-yl)-ethyl]-piperidin-4-yl}-benzamide,
N-[2-(4-bromo-phenyl)-ethyl]-2-{1-[2-(3-oxo-2,3-dihydro-benzo[1,4]oxazin-4-yl)-ethyl]-piperidin-4-yl}-benzamide,
[4-(2-{1-[2-(3-oxo-2,3-dihydro-benzo[1,4]oxazin-4-yl)-ethyl]-piperidin-4-yl}-benzoylamino)-butyl]-carbamic acid tert-butyl ester,
4-[(2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester,
N-[2-(3-naphthalen-1-yl-ureido)-ethyl]-2-{1-[2-(3-oxo-2,3-dihydro-benzo[1,4]oxazin-4-yl)-ethyl]-piperidin-4-yl}-benzamide,
5-chloro-2-{1-[2-(3-oxo-2,3-dihydro-benzo[1,4]oxazin-4-yl)-ethyl]-piperidin-4-yl}-N-phenethyl-benzamide,
4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid tert-butyl ester,
[4-(5-chloro-2-{1-[2-(3-oxo-2,3-dihydro-benzo[1,4]oxazin-4-yl)-ethyl]-piperidin-4-yl}-benzoylamino)-butyl]-carbamic acid tert-butyl ester,
5-chloro-N-(2-naphthalen-2-yl-ethyl)-2-{1-[2-(3-oxo-2,3-dihydro-benzo[1,4]oxazin-4-yl)-ethyl]-piperidin-4-yl}-benzamide,
5-chloro-N-[2-(1H-indol-3-yl)-ethyl]-2-{1-[2-(3-oxo-2,3-dihydro-benzo[1,4]oxazin-4-yl)-ethyl]-piperidin-4-yl}-benzamide,
4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzyl ester,
N-(1-benzoyl-piperidin-4-ylmethyl)-5-chloro-2-{1-[2-(3-oxo-2,3-dihydro-benzo[1,4]oxazin-4-yl)-ethyl]-piperidin-4-yl}-benzamide,
5-chloro-N-[1-(3,3-dimethyl-butyryl)-piperidin-4-ylmethyl]-2-{1-[2-(3-oxo-2,3-dihydro-benzo[1,4]oxazin-4-yl)-ethyl]-piperidin-4-yl}-benzamide,
4-[2-(5-chloro-2-{1-[2-(3-oxo-2,3-dihydro-benzo[1,4]oxazin-4-yl)-ethyl]-piperidin-4-yl}-benzoylamino)-ethyl]-piperazine-1-carboxylic acid tert-butyl ester,
4-[(5-chloro-2-{1-[2-(3-oxo-2,3-dihydro-benzo[1,4]oxazin-4-yl)-ethyl]-piperidin-4-yl}-benzoylamino)-methyl]-piperidine-1-carboxylic acid benzylamide,
4-[2-(5-chloro-2-{1-[2-(3-oxo-2,3-dihydro-benzo[1,4]oxazin-4-yl)-ethyl]-piperidin-4-yl}-benzoylamino)-ethyl]-piperidine-1-carboxylic acid tert-butyl ester,
[4-(5-chloro-2-{1-[2-(3-oxo-2,3-dihydro-benzo[1,4]oxazin-4-yl)-ethyl]-piperidin-4-yl}-benzoylamino)-butyl]-carbamic acid benzyl ester,
[5-(5-chloro-2-{1-[2-(3-oxo-2,3-dihydro-benzo[1,4]oxazin-4-yl)-ethyl]-piperidin-4-yl}-benzoylamino)-pentyl]-carbamic acid tert-butyl ester,
5-chloro-2-{1-[2-(3-oxo-2,3-dihydro-benzo[1,4]oxazin-4-yl)-ethyl]-piperidin-4-yl}-N-(2-piperidin-1-yl-ethyl)-benzamide,
5-chloro-2-{1-[2-(3-oxo-2,3-dihydro-benzo[1,4]oxazin-4-yl)-ethyl]-piperidin-4-yl}-N-(1-phenylmethanesulfonyl-piperidin-4-ylmethyl)-benzamide,
[6-(5-chloro-2-{1-[2-(3-oxo-2,3-dihydro-benzo[1,4]oxazin-4-yl)-ethyl]-piperidin-4-yl}-benzoylamino)-hexyl]-carbamic acid tert-butyl ester,
[5-(5-chloro-2-{1-[2-(3-oxo-2,3-dihydro-benzo[1,4]oxazin-4-yl)-ethyl]-piperidin-4-yl}-benzoylamino)-pentyl]-carbamic acid benzyl ester,
5-chloro-N-[5-(3,3-dimethyl-butyrylamino)-pentyl]-2-{1-[2-(3-oxo-2,3-dihydro-benzo[1,4]oxazin-4-yl)-ethyl]-piperidin-4-yl}-benzamide,
N-[5-(3-benzyl-ureido)-pentyl]-5-chloro-2-{1-[2-(3-oxo-2,3-dihydro-benzo[1,4]oxazin-4-yl)-ethyl]-piperidin-4-yl}-benzamide,
5-chloro-2-{1-[2-(3-oxo-2,3-dihydro-benzo[1,4]oxazin-4-yl)-ethyl]-piperidin-4-yl}-N-(5-phenylmethanesulfonylamino-pentyl)-benzamide,
{2-[2-(5-chloro-2-{1-[2-(3-oxo-2,3-dihydro-benzo[1,4]oxazin-4-yl)-ethyl]-piperidin-4-yl}-benzoylamino)-ethoxy]-ethyl}-carbamic acid tert-butyl ester,
5-chloro-N-[5-(3-isopropyl-ureido)-pentyl]-2-{1-[2-(3-oxo-2,3-dihydro-benzo[1,4]oxazin-4-yl)-ethyl]-piperidin-4-yl}-benzamide, 5-chloro-2-{1-[2-(3-oxo-2,3-dihydro-benzo[1,4]oxazin-4-yl)-ethyl]-piperidin-4-yl}-N-[5-(3-phenyl-ureido)-pentyl]-benzamide, 5-chloro-2-{1-[2-(3-oxo-2,3-dihydro-benzo[1,4]oxazin-4-yl)-ethyl]-piperidin-4-yl}-N-[5-(3-phenethyl-ureido)-pentyl]-benzamide,

[5-(5-chloro-2-{1-[2-(2-oxo-3,4-dihydro-2H-quinolin-1-yl)-ethyl]-piperidin-4-yl}-benzoylamino)-pentyl]-carbamic acid tert-butyl ester, 5-chloro-2-{1-[1-methyl-2-(3-oxo-2,3-dihydro-benzo[1,4]oxazin-4-yl)-ethyl]-piperidin-4-yl}-N-(1-phenyl-methanesulfonyl-piperidin-4-ylmethyl)-benzamide, 4-[2-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-ethyl]-piperazine-1-carboxylic acid tert-butyl ester, and

[5-(5-chloro-2-{8-[2-(3-oxo-2,3-dihydro-benzo[1,4]oxazin-4-yl)-ethyl]-8-aza-bicyclo[3.2.1]oct-2-en-3-yl}-benzoylamino)-pentyl]-carbamic acid tert-butyl ester.

32. A pharmaceutical composition comprising the compound of claim 1 and a pharmaceutically acceptable carrier, excipient or diluent.

\* \* \* \* \*